United States Patent
Kaushal

(10) Patent No.: US 12,220,432 B2
(45) Date of Patent: *Feb. 11, 2025

(54) CARDIAC STEM CELLS FOR CARDIAC REPAIR

(71) Applicant: University of Maryland, Baltimore, Baltimore, MD (US)

(72) Inventor: Sunjay Kaushal, Chicago, IL (US)

(73) Assignee: University of Maryland, Baltimore, Baltimore, MD (US)

(*) Notice: Subject to any disclaimer, the term of this patent is extended or adjusted under 35 U.S.C. 154(b) by 12 days.

This patent is subject to a terminal disclaimer.

(21) Appl. No.: 18/175,154

(22) Filed: Feb. 27, 2023

(65) Prior Publication Data

US 2023/0293597 A1 Sep. 21, 2023

Related U.S. Application Data

(60) Continuation of application No. 17/191,526, filed on Mar. 3, 2021, now Pat. No. 11,633,431, which is a continuation of application No. 15/728,061, filed on Oct. 9, 2017, now Pat. No. 10,967,007, which is a division of application No. 14/712,793, filed on May 14, 2015, now abandoned.

(60) Provisional application No. 62/010,742, filed on Jun. 11, 2014, provisional application No. 61/993,055, filed on May 14, 2014.

(51) Int. Cl.
| A61K 35/34 | (2015.01) |
| A61K 38/18 | (2006.01) |
| A61K 38/19 | (2006.01) |
| A61P 9/10 | (2006.01) |

(52) U.S. Cl.
CPC .......... *A61K 35/34* (2013.01); *A61K 38/1833* (2013.01); *A61K 38/1866* (2013.01); *A61K 38/1891* (2013.01); *A61K 38/19* (2013.01); *A61K 38/195* (2013.01); *A61P 9/10* (2018.01)

(58) Field of Classification Search
CPC .............................. A61K 35/34; A61K 38/1866
See application file for complete search history.

(56) References Cited

U.S. PATENT DOCUMENTS

| 6,372,494 B1 | 4/2002 | Naughton et al. |
| 10,967,007 B2 | 4/2021 | Kaushal |
| 11,633,431 B2 | 4/2023 | Kaushal |
| 12,064,454 B2 | 8/2024 | Kaushal |
| 2006/0239983 A1 | 10/2006 | Anversa |
| 2011/0014161 A1 | 1/2011 | Wang et al. |
| 2015/0203844 A1 | 7/2015 | Marban et al. |
| 2015/0216905 A1 | 8/2015 | Kreke et al. |
| 2015/0328263 A1 | 11/2015 | Kaushal |
| 2022/0387518 A1 | 12/2022 | Mishra et al. |
| 2024/0000851 A1 | 1/2024 | Kaushal |
| 2024/0033298 A1 | 2/2024 | Kaushal |

FOREIGN PATENT DOCUMENTS

| CN | 101820890 A | 9/2010 |
| CN | 103347526 A | 10/2013 |
| CN | 103687626 A | 3/2014 |
| CN | 108379662 A | 8/2018 |
| EP | 2184068 A1 | 5/2010 |
| EP | 4058036 A1 | 9/2022 |
| EP | 4180050 A1 | 5/2023 |
| WO | WO-2006121532 A2 | 11/2006 |
| WO | WO-2007100530 A2 | 9/2007 |
| WO | WO-2008081457 A2 | 7/2008 |
| WO | WO-2012061491 A1 | 5/2012 |
| WO | WO-2012158910 A2 | 11/2012 |
| WO | WO-2014114465 A1 | 7/2014 |
| WO | WO-2014164680 A1 | 10/2014 |
| WO | WO-2021097329 A1 | 5/2021 |

OTHER PUBLICATIONS

Simpson et al. A Strong Regenerative Ability of Cardiac Stem Cells Derived From Neonatal Hearts. Circulation. 2012; 126; S46-S53. (including supplemental materials) (Year: 2012).*
Sano et al. Cardiac stem cell therapy: Does a newborn infant's heart have infinite potential for stem cell therapy? The Journal of Thoracic and Cardiovascular Surgery. 2022; 163:242-7 (Year: 2022).*
Bao et al. C-Kit Positive Cardiac Stem Cells and Bone Marrow-Derived Mesenchymal Stem Cells Synergistically Enhance Angiogenesis and Improve Cardiac Function After Myocardial Infarction in a Paracrine Manner. J Card Fail 23(5):403-415 (2017).
British Heart Foundation—Conditions. https://www.bhf.org.uk/informationsupport/conditions (No date given).
Dainichi et al. Classification of inflammatory skin diseases: A proposal based on the disorders of the three-layered defense systems, barrier, innate immunity and acquired immunity. J Dermatol Sci 76(2):81-9 (2014).
Inflammatory Arthritis. Available at https://www.hss.edu/condition-list_inflammatory-arthritis.asp (2022).
Inflammatory Arthritis Center. Available at https://www.hss.edu/inflammatory-arthritis-center.asp (2023).
U.S. Appl. No. 18/459,692 Office Action dated Oct. 19, 2023.
Cheng, K et al.: Human Cardiosphere-derived Cells from Advanced Heart Failure Patients Exhibit Augmented Functional Potency in Myocardial Repair. JACC. Heart Failure 2(1):49-61 (2014).

(Continued)

*Primary Examiner* — Taeyoon Kim
(74) *Attorney, Agent, or Firm* — Wilson Sonsini Goodrich & Rosati

(57) ABSTRACT

Embodiments of the disclosure concern compositions and methods of use related to particular c-kit+ mesenchymal cells, including cardiac stem cells, obtained from a pediatric or neonatal individual. In specific embodiments, the cells, or conditioned medium or partial or total secretomes thereof, are provided in an effective amount to an individual in need thereof.

9 Claims, 74 Drawing Sheets

(56) References Cited

OTHER PUBLICATIONS

D'Amario, D et al.: Functionally competent cardiac stem cells can be isolated from endomyocardial biopsies of patients with advanced cardiomyopathies. Circulation Research 108:857-861, (Year: 2011).
Database WPI Week 201865, Thomson Scientific, London, GB; AN 2018-64351A (2017), XP002808486.
Dorko, E et al.: Detection of anti-Candida antibodies in neonates from a neonatal intensive care unit. Folia Microbiol 47:297-301, (Year: 2002).
EP20829738.2 European Examination Report dated Dec. 12, 2023.
EP22215642.4 European Search Report dated Jan. 31, 2023.
Escudier, M et al.: Clinical Features, Management, and Outcomes of Immune Checkpoint Inhibitor-Related Cardiotoxicity. Circulation 136(21):2085-2087. https://doi.org/10.1161/CIRCULATIONAHA.117.030571.
Gallo, RL et al.: Biology and clinical relevance of naturally occurring antimicrobial peptides. J Allergy Clin Immunol 110:823-831, (Year: 2002).
Pawan, KC et al.: Cardiac tissue-derived extracellular matrix scaffolds for myocardial repair: advantages and challenges. Regen Biomater 6(4):185-199 (2019).
Simpson, DL et al.: A strong regenerative ability of cardiac stem cells derived from neonatal hearts. Circulation 126:S46-53 (2012).
U.S. Appl. No. 18/459,685 Office Action dated Mar. 21, 2024.
U.S. Appl. No. 18/459,685 Office Action dated Jun. 27, 2024.
U.S. Appl. No. 18/459,692 Notice of Allowance dated May 13, 2024.
U.S. Appl. No. 18/459,692 Office Action dated Dec. 13, 2023.
Zhuang, Y et al.: Establishment and characterization of immortalized human breast cancer cell lines from breast cancer patient-derived xenografts (PDX). Nature Partner Journals, Breast Cancer 7:79 (2021).
Angelini et al. Stem-cell therapy in an experimental model of pulmonary hypertension and right heart failure: Role of paracrine and neurohormonal milieu in the remodeling process. J Heart Lung Transplant 30:1281-1293 (2011).
Anversa et al. Ventricular myocytes are not terminally differentiated in the adult mammalian heart. Circulation Res. 83:1-14 (1998).
Bu et al. Human isl1 heart progenitors generate diverse multipotent cardiovascular cell lineages. Nature 460:113-117 (2009).
Cesselli et al. Effects of age and heart failure on human cardiac stem cell function. The Am J Pathol 179:349-366 (2011).
Chimenti et al. Relative roles of direct regeneration versus paracrine effects of human cardiosphere-derived cells transplanted into infarcted mice. Circ Res. 106:971-980 (2010).
EP22215642.4 European Examination Report dated Mar. 21, 2024.
Genth-Zotz et al. Heat shock protein 70 in patients with chronic heart failure: Relation to disease severity and survival. Int J Cardiol 96:397-401 (2004).
He et al. Human cardiac stem cells isolated from atrial appendages stably express c-kit. PloS One 6:e27719 (2011).
Huoshenshan Hospital, Maternal and Child Health Hospital of Hubei Province, The General Hospital of Central Theater Command, VCANBIO Cell & Gene Engineering Corporation, Ltd. Treatment With Mesenchymal Stem Cells for Severe Corona Virus Disease 2019(COVID-19). https://ClinicalTrials.gov/show/NCT04288102 (2020).
Innovative Precision Medicine Group (IPM) Hangzhou, China, Huoshenshan Hospital, Tianjin Haihe Hospital, VCANBIO Cell & Gene Engineering Corporation, Ltd., Shenzhen third People's Hospital, Fifth Affiliated Hospital, Sun Yat-Sen University. Mesenchymal Stem Cell Treatment for Pneumonia Patients Infected With 2019 Novel Coronavirus. https://ClinicalTrials.gov/show/NCT04252118 (2020).
Kajstura et al., Myocyte proliferation in end-stage cardiac failure in humans. PNAS USA 95(15):8801-8805 (1998).
Kannaiyan et al. Molecular targets of celastrol derived from thunder of god vine: Potential role in the treatment of inflammatory disorders and cancer. Cancer Letters 303:9-20 (2011).
Laflamme et al. Cardiomyocytes derived from human embryonic stem cells in pro-survival factors enhance function of infarcted rat hearts. Nat Biotechnol 25:1015-1024 (2007).
Makkar et al., Intracoronary cardiosphere-derived cells for heart regeneration after myocardial infarction (CADUCEUS): a prospective, randomised phase 1 trial. Lancet 379:895-904 (2012).
Malliaras et al., Intracoronary cardiosphere-derived cells after myocardial infarction: evidence for therapeutic regeneration in the final 1-year results of the CADUCEUS trial. J. Am. Coll. Cardiol. 63(2):110-122 (2014).
Matsuura et al. Adult cardiac sca-I-positive cells differentiate into beating cardiomyocytes. J Biol Chem 279:11384-11391 (2004).
McGinley et al. Mesenchymal stem cell survival in the infarcted heart is enhanced by lentivirus vector-mediated heat shock protein 27 expression. Human Gene Therapy 24:840-851 (2013).
Messina et al. Isolation and expansion of adult cardiac stem cells from human and murine heart. Circulation Res 95:911-921 (2004).
Mirotsou et al. Paracrine mechanisms of stem cell reparative and regenerative actions in the heart. J Mol Cell Cardiol 50:280-289 (2011).
Miyata et al. Myosin heavy chain isoform expression in the failing and nonfailing human heart. Circ Res. 86:386-390 (2000).
Porrello et al. Transient regenerative potential of the neonatal mouse heart. Science 331:1078-1080 (2011).
Rajabi et al. Return to the fetal gene program protects the stressed heart: A strong hypothesis. Heart Fail Rev 12:331-343 (2007).
Razeghi et al. Metabolic gene expression in fetal and failing human heart. Circulation 104:2923-2931 (2001).
Reynolds et al. Generation of neurons and astrocytes from isolated cells of the adult mammalian central nervous system. Science 255:1707-1710 (1992).
Rietze et al. Neural stem cell isolation and characterization. Methods Enzymol 419:3-23 (2006).
Roger. Epidemiology of heart failure. Circ Res. 113:646-659 (2013).
Rossano et al. Prevalence, morbidity, and mortality of heart failure-related hospitalizations in children in the United States: A population-based study. J Card Fail 18:459-470 (2012).
Saha, P et al.: Circulating exosomes derived from transplanted progenitor cells aid the functional recovery of ischemic myocardium. Sci. Transl. Med. 11(493):eaau1168 (2019). doi: 10.1126/scitranslmed.aau1168.
Salminen et al. Celastrol: Molecular targets of thunder god vine. Biochemical Biophys Res Commun 394:439-442 (2010).
Simpson et al. A tissue engineering approach to progenitor cell delivery results in significant cell engraftment and improved myocardial remodeling. Stem Cells 25:2350-2357 (2007).
Smith et al. Regenerative potential of cardiosphere-derived cells expanded from percutaneous endomyocardial biopsy specimens. Circulation 115:896-908 (2007).
Stolzing et al. Stressed stem cells: Temperature response in aged mesenchymal stem cells. Stem Cells Dev 15:478-487 (2006).
Wang et al. Regulation of heat shock protein 60 and 72 expression in the failing heart. J Mol Cell Cardiol 48:360-366 (2010).
Zaruba et al. Cardiomyogenic potential of c-kit(+)-expressing cells derived from neonatal and adult mouse hearts. Circulation 121:1992-2000 (2010).
Zhang et al. Hsp20 functions as a novel cardiokine in promoting angiogenesis via activation of vegfr2. PloS One 7:e32765 (2012).
Abdullah et al., Stem Cell Therapy in Single-Ventricle Physiology: Recent Progress and Future Directions. Semin Thorac Cardiovasc Surg Pediatr Card Surg Annu 24:67-76 (2021).
Afanasiev et al. Effect of stress-proteins on survival of bone marrow mesenchymal stem cells after intramyocardial transplantation against the background of postinfarction heart remodeling. Bull Exp Biol Med 146:111-115 (2008).
Affiliated Hospital to Academy of Military Medical Sciences, Ivy Institute of Stem Cells Co. Ltd. Human Umbilical-Cord-Derived Mesenchymal Stem Cell Therapy in Acute Lung Injury. https://ClinicalTrials.gov/show/NCT02444455 (2015).
Affiliated Hospital to Academy of Military Medical Sciences, Ivy Institute of Stem Cells Co. Ltd.. Human Umbilical-Cord-Derived Mesenchymal Stem Cell Therapy in Paraquat Poisoning Induced Lung Injury. https://ClinicalTrials.gov/show/NCT02444858 (2015).

(56) References Cited

OTHER PUBLICATIONS

Afzal et al., Adult Bone Marrow Cell Therapy for Ischemic Heart Disease: Evidence and Insights from Randomized Controlled Trials. Circ Res. 117(6):558-575 (2015).
Al Khaldi et al., Postnatal bone marrow stromal cells elicit a potent VEGF-dependent neoangiogenic response in vivo. Gene Ther. 10(8):621-629 (2003).
Alvey et al., Engineering macrophages to eat Cancer: from "marker of self" CD47 and phagocytosis to differentiation. Journal of Leukocyte Biology 102:31-40 (2017).
Ambastha et al., Regenerative medicine therapy for single ventricle congenital heart disease. Transl Pediatr 7(2):176-187 (2018).
Amicone et al., Transgenic expression in the liver of truncated Met blocks apoptosis and permits immortalization of hepatocytes. EMBO J. 16 (3):495-503 (1997).
Anzai et al., C-kit associated with the transmembrane 4 superfamily proteins constitutes a functionally distinct subunit in human hematopoietic progenitors. Blood 99(12):4413-4421 (2002).
Askari et al., Effect of stromal-cell-derived factor 1 on stem-cell homing and tissue regeneration in ischaemic cardiomyopathy. Lancet 362(9385):697-703 (2003).
Assmus et al., Transcoronary transplantation of progenitor cells after myocardial infarction. New England Journal of Medicine 355(12):1222-12232 (2006).
Assmus et al., Transplantation of progenitor cells and regeneration enhancement in acute myocardial infarction (TOPCARE-AMI). Circulation 106(24):3009-3017 (Nov. 2002).
Bagno et al., Mesenchymal Stem Cell-Based Therapy for Cardiovascular Disease: Progress and Challenges. Mol Ther. 26(7):1610-1623 (2018).
Barile et al., Beneficial effects of exosomes secreted by cardiac-derived progenitor cells and other cell types in myocardial ischemia. Stem Cell Investig. 4:93 (2017).
Barile et al., Cardioprotection by cardiac progenitor cell-secreted exosomes: role of pregnancy-associated plasma protein-A. Cardiovasc Res. 114(7):992-1005 (2018).
Bartolucci et al., Safety and Efficacy of the Intravenous Infusion of Umbilical Cord Mesenchymal Stem Cells in Patients with Heart Failure: A Phase 1/2 Randomized Controlled Trial (RIMECARD Trial [Randomized Clinical Trial of Intravenous Infusion Umbilical Cord Mesenchymal Stem Cells on Cardiopathy]). Circ Res. 121(10):1192-1204 (2017).
Baxter et al., Study of telomere length reveals rapid aging of human marrow stromal cells following in vitro expansion. Stem Cells 22(5):675-82 (2004).
Bearzi et al., Human cardiac stem cells. PNAS USA 104(35):14068-14073 (2007).
Beeres et al., Effect of intramyocardial injection of autologous bone marrow-derived mononuclear cells on perfusion, function, and viability in patients with drug-refractory chronic ischemia. J Nucl Med. 47(4):574-580 (2006).
Beltrami et al., Adult cardiac stem cells are multipotent and support myocardial regeneration. Cell 114(6):763-76 (2003).
Beltrami et al., Pluripotency rush! Molecular cues for pluripotency, genetic reprogramming of adult stem cells, and widely multipotent adult cells. Pharmacology & Therapeutics 124(1):23-30 (2009).
Benjamin et al., Stress (Heat Shock) Proteins Molecular Chaperones in Cardiovascular Biology and Disease. Circ Res. 83:117-132 (1998).
Bergmann et al., Evidence for cardiomyocyte renewal in humans. Science 324(5923):98-102 (2009).
Bittle et al., Clinical Progress in Cell Therapy for Single Ventricle Congenital Heart Disease. Circ Res 120(7):1060-1062 (2017).
Bittle et al., Stem Cell Therapy for Hypoplastic Left Heard Syndrome: Mechanism, Clinical Application, and Future Directions. Cir Res 123(2):288-300 (2018).
Boerma et al., Radiation Biology: Targeting CD47 in Cancer Growth Inhibition and Normal Tissue Protection. Int J Radiat Oncol Biol Phys. 96(2):245-247 (2016).
Bolli et al., Abstract 14080: A phase II randomized, double-blind, controlled trial of combined mesenchymal stromal cells and c-kit+ cardiac progenitor cells in ischemic heart failure: the CCTRN Concert-HF Trial. Circulation 142:A14080 (2020).
Bolli et al., Cardiac stem cells in patients with ischaemic cardiomyopathy (SCIPIO): initial results of a randomised phase 1 trial. Lancet 378:1847-1857 (2011) (Article Retracted).
Bolli et al., Intracoronary delivery of autologous cardiac stem cells improves cardiac function in a porcine model of chronic ischemic cardiomyopathy. Circulation. 128(2):122-31 (2013).
Bonab et al., Aging of mesenchymal stem cell in vitro. BMC Cell Biol. 7:14 (2006).
Brigouri et al., Direct intramyocardial percutaneous delivery of autologous bone marrow in patients with refractory myocardial angina. Am Heart J. 151(3):674-680 (2006).
Buja. Cardiac repair and the putative role of stem cells. J Mol Cell Cardiol 128:96-104 (2019).
Burke et al., Exosomes from myeloid-derived suppressor cells carry biologically active proteins. J Proteome Res. 13(2):836-843 (2014).
Butler et al., Intravenous Allogeneic Mesenchymal Stem Cells for Nonischemic Cardiomyopathy: Safety and Efficacy Results of a Phase II-A Randomized Trial. Circ Res. 120(2):332-340 (2017).
Caplan et al., Mesenchymal stem cells as trophic mediators. Journal of Cellular Biochemistry 98(5):1076-1084 (2006).
Capogrossi, Cardiac stem cells fail with aging: a new mechanism for the age-dependent decline in cardiac function. Circ Res 94(4):411-413 (2004).
CAR-T (Shanghai ) Biotechnology Co. L. Novel Coronavirus Induced Severe Pneumonia Treated by Dental Pulp Mesenchymal Stem Cells. https://ClinicalTrials.gov/show/NCT04302519 (2020).
Carter et al., Characterizing the impact of 2D and 3D culture conditions on the therapeutic effects of human mesenchymal stem cell secretome on corneal wound healing in vitro and ex vivo. Acta Biomater 99:247-257 (2019).
Case Western Reserve University, Cystic Foundation. Safety and Tolerability Study of Allogeneic Mesenchymal Stem Cell Infusion in Adults with Cystic Fibrosis. https://ClinicalTrials.gov/show/NCT02866721 (2016).
Casiraghi et al., Multipotent mesenchymal stromal cell therapy and risk of malignancies. Stem Cell Rev. 9(1):65-79 (2013).
Castro-Manrereza et al., Human mesenchymal stromal cells from adult and neonatal sources: a comparative in vitro analysis of their immunosuppressive properties against T cells. Stem Cells Dev. 23(11):1217-1232 (2014).
Cellavita Pesquisa Cientifica Ltda, Hospital Vera Cruze. Mesenchymal Stem Cell NestCell® to Treat Patients with Severe COVID-19 Pneumonia. https://ClinicalTrials.gov/show/NCT04315987 (2020).
Chambers et al., A phase 1b study of placenta-derived mesenchymal stromal cells in patients with idiopathic pulmonary fibrosis. Respirology 19(7):1013-1018 (2014).
Chao et al., The CD47-SIRPα pathway in cancer immune evasion and potential therapeutic implications. Curr Opin Immunol 24:225-32 (2012).
Chen et al., Effect on left ventricular function of intracoronary transplantation of autologous bone marrow mesenchymal stem cell in patients with acute myocardial infarction. Am J Cardiol. 94(1):92-5 (2004).
Chen et al., Loss of proliferative capacity and induction of senescence in oxidatively stressed human fibroblasts. The Journal of Biological Chemistry 279(47):49439-494346 (2004).
Chen et al., Mesenchymal stem cells upregulate Treg cells via sHLA-G in SLE patients. Int Immunopharmacol. 44:234-241 (2017).
Children's Hospital of Chongqing Medical University.. Follow-Up Study of Mesenchymal Stem Cells for Bronchopulmonary Dysplasia. https://ClinicalTrials.gov/show/NCT03873506 (2018).
Children's Hospital of Chongqing Medical University. Human Mesenchymal Stem Cells For Infants at High Risk for Bronchopulmonary Dysplasia. https://ClinicalTrials.gov/show/NCT03774537 (2019).
China Medial University Hospital. Intratracheal Umbilical Cord-derived Mesenchymal Stem Cells for Severe Bronchopulmonary Dysplasia. https://ClinicalTrials.gov/show/NCT01207869 (2010).

(56) References Cited

OTHER PUBLICATIONS

Chowdhury et al., Changes in speckle tracking echocardiography measures of ventricular function after percutaneous implantation of the Edwards SAPIEN transcatheter heart valve in the pulmonary position. Echocardiography 32(3):461-469 (2015).
Chugh et al., Administration of cardiac stem cells in patients with ischemic cardiomyopathy: the SCIPIO trial: surgical aspects and interim analysis of myocardial function and viability by magnetic resonance. Circulation 126(11 Suppl 1):S54-64 (2012).
Cle et al., Intravenous infusion of allogeneic mesenchymal stromal cells in refractory or relapsed aplastic anemia. Cytotherapy 17(12):1696-1705 (2015).
Clinica Universidad de Navarra, Universidad de Navarra. Study of Autologous Mesenchymal Stem Cells to Treat Idiopathic Pulmonary Fibrosis. https://ClinicalTrials.gov/show/NCT01919827 (2013).
Daping Hospital and the Research Institute of Surgery of the Third Military Medical University, Children's Hospital of Chongqing Medical University, Chongqing Maternal and Child Health Hospital. Stem Cells for Bronchopulmonary Dysplasia. https://ClinicalTrials.gov/show/NCT03378063 (2017).
Davani et al., Mesenchymal progenitor cells differentiate into an endothelial phenotype, enhance vascular density, and improve heart function in a rat cellular cardiomyoplasty model. Circulation 108:II-253 to II-258 (2003).
De La Fuente, et al., Transendocardial autologous bone marrow in chronic myocardial infarction using a helical needle catheter: 1-year follow-up in an open-label, nonrandomized, single-center pilot study (The TABMMI Study). Am Heart J. 154(1):79.e1-7 (Jul. 2007).
De Witte et al., Aging of bone marrow—and umbilical cord-derived mesenchymal stromal cells during expansion. Cytotherapy 19(7):798-807 (2017).
De Witte et al., Immunomodulation by Therapeutic Mesenchymal Stromal Cells (MSC) Is Triggered Through Phagocytosis of MSC By Monocytic Cells. Stem Cells 36(4):602-615 (2018).
Deng et al., Umbilical Cord-derived Mesenchymal Stem Cells Instruct Monocytes Towards an IL10-producing Phenotype by Secreting IL6 and HGF. Sci Rep. 6:37566 (2016).
Elahi et al., Human Mesenchymal Stromal Cells from Different Sources Diverge in Their Expression of Cell Surface Proteins and Display Distinct Differentiation Patterns. Stem Cells Int. 2016:5646384 (2016).
Ellison et al., Endogenous cardiac stem cell activation by insulin-like growth factor-1/hepatocyte growth factor intracoronary injection fosters survival and regeneration of the infarcted pig heart. J Am. Coll. Cardiol. 58(9):977-986 (2011).
Eulalio et al., Functional screening identifies miRNAs inducing cardiac regeneration. Nature 492(7429):376-381 (2012).
Fazzina et al., A new standardized clinical-grade protocol for banking human umbilical cord tissue cells. Transfusion 55(12):2864-2873 (2015).
Federal Research Clinical Center of Federal Medical & Biological Agency, Russia. Safety and Efficacy of Allogeneic Mesenchymal Stem Cells in Patients with Rapidly Progressive Interstitial Lung Disease. https://ClinicalTrials.gov/show/NCT02594839 (2013).
Fekete et al., GMP-compliant isolation and large-scale expansion of bone marrow-derived MSC. PLoS One 7(8):e43255 (2012).
Feng et al., Heat shock improves sca-1+ stem cell survival and directs ischemic cardiomyocytes toward a prosurvival phenotype via exosomal transfer: A critical role for hsfl/mir-34a/hsp70 pathway. Stem Cells 32:462-472 (2014).
Feng et al., Phagocytosis checkpoints as new targets for cancer immunotherapy. Nat Rev Cancer 19(10):568-586 (2019).
Fernandez-Aviles et al., Safety and Efficacy of Intracoronary Infusion of Allogeneic Human Cardiac Stem Cells in Patients with ST-segment Elevation Myocardial Infarction and Left Ventricular Dysfunction. Circ Res. 123(5):579-589 (2018).
First Affiliated Hospital of Xinjian Medical University. NK Cells Treatment for Novel Coronavirus Pneumonia. https://ClinicalTrials.gov/show/NCT04280224 (2020).
Fontaine et al., Unraveling the Mesenchymal Stromal Cells' Paracrine Immunomodulatory Effects. Transfus Med Rev. 30(1):37-43 (2016).
Fu et al., High expression of CD47 predicts adverse prognosis in Chinese patients and suppresses immune response in melanoma. Biomed Pharmacother. 93:1190-1196 (2017).
Fuchs et al., Catheter-based autologous bone marrow myocardial injection in no-option patients with advanced coronary artery disease: a feasibility study. J Am Coll Cardiol. 41(10):1721-1724 (2003).
Fuentes et al., Human Neonatal Cardiovascular Progenitors: Unlocking the Secret to Regenerative Ability. PLoS One 8(10):e77464 (2013).
Galinanes et al., Autotransplantation of unmanipulated bone marrow into scarred myocardium is safe and enhances cardiac function in humans. Cell Transplant 13(1):7-13 (2004).
Gambini et al., C-kit+ cardiac progenitors exhibit mesenchymal markers and preferential cardiovascular commitment. Cardiovascular Research 89:362-373 (2011).
Garbern et al., Cardiac stem cell therapy and the promise of heart regeneration. Cell Stem Cell 12(6):689-98 (2013).
Garg et al., Human Induced Pluripotent Stem Cell-Derived Cardiomyocytes as Models for Cardiac Channelopathies: A Primer for Non-Electrophysiologists. Circulation research. 123(2):224-243 (2018).
Ghanei. Baqiyatallah Medical Sciences University. Mesenchymal Stem Cells Therapy for Treatment of Airway Remodeling in Mustard Patients. https://ClinicalTrials.gov/show/NCT02749448 (2015).
Glassberg et al., Allogeneic Human Mesenchymal Stem Cells in Patients with Idiopathic Pulmonary Fibrosis via Intravenous Delivery (AETHER): A Phase I Safety Clinical Trial. Chest. 151(5):971-981 (2017).
Glassberg. Miami University of Miami. Safety and Potential Efficacy of Human Mesenchymal Stem Cells in Non-Cystic Fibrosis Bronchiectasis. https://ClinicalTrials.gov/show/NCT02625246 (2016).
Glassberg. Miami University of Miami. Allogeneic Human Cells (hMSC) Via Intravenous Delivery in Patients with Mild Asthma. https://ClinicalTrials.gov/show/NCT03137199 (2017).
Gnecchi et al., Paracrine mechanisms in adult stem cell signaling and therapy. Circulation Research 103(11):1204-1219 (2008).
Gnecchi et al., Evidence supporting paracrine hypothesis for Akt-modified mesenchymal stem cell-mediated cardiac protection and functional improvement. FASEB Journal : official publication of the Federation of American Societies for Experimental Biology 20(6):661-669 (2006).
Go et al., Executive summary: heart disease and stroke statistics—2014 update: a report from the American Heart Association. Circulation 129(3):399-410 (2014).
Go et al., Heart disease and stroke statistics—2014 update: a report from the American Heart Association. Circulation 129(3):e28-e292 (2014).
Goto et al., Efficacy of anti-CD47 antibody-mediated phagocytosis with macrophages against primary effusion lymphoma. Eur J Cancer. 50(10):1836-1846 (2014).
Greider et al., Identification of a specific telomere terminal transferase activity in Tetrahymena extracts. Cell 43(2 Pt 1):405-13 (1985).
Gunasekaran et al., Comparative efficacy and mechanism of action of cardiac progenitor cells after cardiac injury. iScience 25(8):104656 (2022).
Hamano et al., Local implantation of autologous bone marrow cells for therapeutic angiogenesis in patients with ischemic heart disease: clinical trial and preliminary results. Jpn Circ J. 65(9):845-847 (2001).
Han et al., E-Prostanoid 2 Receptor Overexpression Promotes Mesenchymal Stem Cell Attenuated Lung Injury. Hum Gene Ther. 27(8):621-630 (2016).
Hare et al., A randomized, double-blind, placebo-controlled, dose-escalation study of intravenous adult human mesenchymal stem cells (prochymal) after acute myocardial infarction. J Am Coll Cardiol. 54(24):2277-2286 (2009).
Hare et al., Allogeneic Human Cells (hMSC)in Patients with Idiopathic Pulmonary Fibrosis Via Intravenous Delivery (AETHER). https://ClinicalTrials.gov/show/NCT02013700 (2013).

(56) References Cited

OTHER PUBLICATIONS

Hare et al., Comparison of allogeneic vs autologous bone marrow-derived mesenchymal stem cells delivered by transendocardial injection in patients with ischemic cardiomyopathy: the POSEIDON randomized trial. JAMA 308(22):2369-2379 (2012).
Hare et al., Human Mesenchymal Stem Cells Infusion in Patients with Cystic Fibrosis. https://ClinicalTrials.gov/show/NCT03058068 (2020).
Hass et al., Different populations and sources of human mesenchymal stem cells (MSC): A comparison of adult and neonatal tissue-derived MSC. Cell Commun Signal. 9:12 (2011).
Hatzistergos et al., Stimulatory Effects of Mesenchymal Stem Cells on cKit+ Cardiac Stem Cells Are Mediated by SDF1/CXCR4 and SCF/cKit Signaling Pathways. Circ Res. 119(8):921-930 (2016).
Haubner et al., Functional Recovery of a Human Neonatal Heart After Severe Myocardial Infarction. Circ Res. 118(2):216-221 (2016).
Hayflick et al., The serial cultivation of human diploid cell strains. Exp. Cell Res. 25:585-621 (1961).
Hayflick. The biology of human aging. The American Journal of the Medical Sciences 265(6):432-446 (1973).
Hendrikx et al., Recovery of regional but not global contractile function by the direct intramyocardial autologous bone marrow transplantation: results from a randomized controlled clinical trial. Circulation 114(1 Suppl.):I101-I107 (2006).
Hierlihy et al., The post-natal heart contains a myocardial stem cell population. FEBS Letters 530(1-3):239-243 (2002).
Hiyama et al., Telomere and telomerase in stem cells. British Journal of Cancer 96(7):1020-1024 (2007).
Hodonsky et al., Effects of Scaffold Material Used in Cardiovascular Surgery on Mesenchymal Stem Cells and Cardiac Progenitor Cells. Ann Thorac Surg. 99(2):605-611 (2015).
Hong et al., A highly sensitive and accurate method to quantify absolute numbers of c-kit+ cardiac stem cells following transplantation in mice. Basic Res Cardiol. 108(3):346 (2013).
Hong et al., c-kit+ Cardiac stem cells alleviate post-myocardial infarction left ventricular dysfunction despite poor engraftment and negligible retention in the recipient heart. PLoS One 9(5):e96725 (2014).
Horie et al., Cell therapy in acute respiratory distress syndrome. J Thorac Dis. 10(9):5607-5620 (2018).
Hu et al., CRISPR/Cas9-mediated reversibly immortalized mouse bone marrow stromal stem cells (BMSCs) retain multipotent features of mesenchymal stem cells (MSCs). Oncotarget 8(67):111847-111865 (2017).
Huang et al., An off-the-shelf artificial cardiac patch improves cardiac repair after myocardial infarction in rats and pigs. Sci Transl Med. 12(538):eaat9683 (2020).
Huang et al., Clinical features of patients infected with 2019 novel coronavirus in Wuhan, China. The Lancet, 395, 497-506 (2020).
Hultdin, et al., Telomere analysis by fluorescence in situ hybridization and flow cytometry. Nucleic Acids Res. 26(16):3651-6 (1998).
Hunsberger et al., Improving patient outcomes with regenerative medicine: How Regenerative Medicine Manufacturing Society plans to move the needle forward in cell manufacturing, standards, 3D bioprinting, artificial intelligence—enabled automation, education, and training. Stem Cells Transl Med. 9(7):728-733 (2020).
Instituto de Salud Carlos III. Mesenchymal Stem Cell Therapy for Bronchopulmonary Dysplasia in Preterm Babies. https://ClinicalTrials.gov/show/NCT02443961 (2019).
Introna et al., Treatment of graft versus host disease with mesenchymal stromal cells: a phase I study on 40 adult and pediatric patients. Biol Blood Marrow Transplant. 20(3):375-381 (2014).
Ionescu et al., Stem cell conditioned medium improves acute lung injury in mice: in vivo evidence for stem cell paracrine action. Am J Physiol Lung Cell Mol Physiol. 303(11):L967-L977 (2012).
Itzhaki-Alfia et al., Patient Characteristics and Cell Source Determine the Number of Isolated Human Cardiac Progenitor Cells. Circulation 120:2559-2566 (2009).
Jahn et al., Regulatory T Cells Know What Is Needed to Regenerate. Developmental Cell 43(6):651-652 (2017).

Jaiswal et al., CD47 is upregulated on circulating hematopoietic stem cells and leukemia cells to avoid phagocytosis. Cell 138:271-285 (2009).
Jansen of Lorkeers et al., Cyclosporin in cell therapy for cardiac regeneration. J Cardiovasc Transl Res. 7(5):475-482 (2014).
Janssens et al., Autologous bone marrow-derived stem-cell transfer in patients with ST-segment elevation myocardial infarction: double-blind, randomized controlled trial. Lancet 367(9505):113-121 (2006).
Jiang et al., Transplantation of placenta-derived mesenchymal stem cells in type 2 diabetes: a pilot study. Front Med. 5(1):94-100 (2011).
Jun et al., The pathology of bleomycin-induced fibrosis is associated with loss of resident lung mesenchymal stem cells that regulate effector T-cell proliferation. Stem Cells. 29(4):725-735 (2011).
Junker et al., MicroRNA profiling of multiple sclerosis lesions identifies modulators of the regulatory protein CD47. Brain 132(Pt 12):3342-3352 (2009).
Kaeberlein. Lessons on longevity from budding yeast. Nature 464(7288):513-519 (2010).
Kajstura et al., Cardiomyogenesis in the aging and failing human heart. Circulation 126(15):1869-81 (2012) [Article retracted].
Kamerkar et al., Exosomes facilitate therapeutic targeting of oncogenic KRAS in pancreatic cancer. Nature 546: 498-503 (2017).
Karantalis et al., Allogeneic cell therapy: a new paradigm in therapeutics. Circ Res. 116(1):12-15 (2015).
Kasiak Research Pvt. Ltd. Evaluate Safety and Efficacy of Intravenous Autologous ADMSc for Treatment of Idiopathic Pulmonary Fibrosis. https://ClinicalTrials.gov/show/NCT02135380 (2014).
Katritsis et al., Transcoronary transplantation of autologous mesenchymal stem cells and endothelial progenitors into infarcted human myocardium. Catheter Cardiovasc Interv. 65(3):321-329 (2005).
Kaushal et al., Autologous Cardiac Stem Cell Injection in Patients with Hypoplastic Left Heart Syndrome (Child Study). Pediatr Cardiol 43(7):1481-1493 (2022).
Kaushal et al., Stem cells on a new stage: Treatment of hypoplastic left heart syndrome. J Thorac Cardiovasc Surg. 150(5):1209-1211 (2015).
Kaushal et al., Study design and rationale for ELPIS: A phase I/IIb randomized pilot study of allogeneic human mesenchymal stem cell injection in patients with hypoplastic left heart syndrome. Am Heart J 192:48-56 (2017).
Kiani., Institute R, Hospital MD. Safety Study of Endobronchial Transplantation of Autologous Mesenchymal Stem Cells (MSCs) in Emphysema Patients. https://ClinicalTrials.gov/show/NCT01758055 (2012).
Kim et al., Proteomic analysis of microvesicles derived from human mesenchymal stem cells. J Proteome Res. 11(2):839-49 (2012).
Kinnaird et al., Local delivery of marrow-derived stromal cells augments collateral perfusion through paracrine mechanisms. Circulation 109(12):1543-1549 (2004).
Kinnaird et al., Marrow-derived stromal cells express genes encoding a broad spectrum of arteriogenic cytokines and promote in vitro and in vivo arteriogenesis through paracrine mechanisms. Circulation Research 94(5):678-685 (2004).
Ko et al., Mesenchymal stem/stromal cells precondition lung monocytes/macrophages to produce tolerance against allo- and autoimmunity in the eye. PNAS USA 113(1):158-163 (2016).
Kobayashi et al., Prevention of acute liver failure in rats with reversibly immortalized human hepatocytes. Science 287:1258-62 (2000).
Koh et al., Exosome-SIRPalpha, a CD47 blockade increases cancer cell phagocytosis. Biomaterials 121:121-129 (2017).
Kong et al., CD47: a potential immunotherapy target for eliminating cancer cells. Clin Transl Oncol. 18(11):1051-1055 (2016).
Krasnodembskaya et al., Human mesenchymal stem cells reduce mortality and bacteremia in gram-negative sepsis in mice in part by enhancing the phagocytic activity of blood monocytes. Am J Physiol Lung Cell Mol Physiol. 302(10):L1003-L1013 (2012).
Kudo et al., Implantation of bone marrow stem cells reduces the infarction and fibrosis in ischemic mouse heart. J Mol Cell Cardiol. 35(9):1113-1119 (2003).
Lafferty et al., CCR6 ligands inhibit HIV by inducing APOBEC3G. 115(8):1564-1571 (2010).

(56) References Cited

OTHER PUBLICATIONS

Lee et al., A novel population of extracellular vesicles smaller than exosomes promotes cell proliferation. Cell Commun Signal 17(1):95 (2019).

Leri et al., Ablation of telomerase and telomere loss leads to cardiac dilatation and heart failure associated with p53 upregulation. The EMBO Journal 22(1):131-139 (2003).

Levesque et al., Disruption of the CXCR4/CXCL12 chemotactic interaction during hematopoietic stem cell mobilization induced by GCSF or cyclophosphamide. J Clin Invest. 111(2):187-196 (2003).

Lewis-McDougall et al., Aged-senescent cells contribute to impaired heart regeneration. Aging Cell. 18(3):e12931 (2019).

Lewis-McDougall et al., Senescent, dysfunctional human cardiac progenitor cells (CPCs) accumulate in the aged heart and elimination of senescent cells enhances CPC activation and cardiomyocyte proliferation in aged mice. bioRxiv. https://doi.org/10.1101/397216 (2018).

Li et al., Mesenchymal stem cells in idiopathic pulmonary fibrosis. Oncotarget. 8(60):102600-102616 (2017).

Li et al., MicroRNA-133a suppresses the proliferation, migration, and invasion of laryngeal carcinoma cells by targeting CD47. Tumour Biol. 37:16103-16113 (2016).

Li et al., New Insights into the Role of Exosomes in the Heart After Myocardial Infarction. J Cardiovasc Transl Res. 12(1):18-27 (2019).

Li et al., The safety and feasibility of the local implantation of autologous bone marrow cells for ischemic heart disease. J Card Surg. 18 Suppl 2:S69-75 (2003).

Liang et al., Paracrine mechanisms of mesenchymal stem cell-based therapy: current status and perspectives. Cell Transplant. 23(9):1045-1059 (2014).

Liaocheng People's Hospital. Clinical Study of Adipose Derived Mesenchymal Stem Cells for Treatment of Pulmonary Arterial Hypertension. https://ClinicalTrials.gov/show/NCT04055415 (2019).

Liechty et al., Human mesenchymal stem cells engraft and demonstrate site-specific differentiation after in utero transplantation in sheep. Nat Med. 6(11):1282-1286 (2000).

Lim et al., Intravenous injection of allogeneic umbilical cord-derived multipotent mesenchymal stromal cells reduces the infarct area and ameliorates cardiac function in a porcine model of acute myocardial infarction. Stem Cell Res Ther 9(1):129 (2018).

Ling et al., Wnt signaling controls the fate of mesenchymal stem cells. Gene 433(1-2):1-7 (2009).

Liu et al., Immunomodulation by mesenchymal stem cells in treating human autoimmune disease-associated lung fibrosis. Stem Cell Res Ther. 7(1):63 (2016).

Liu et al., Therapeutic Effects of Bone Marrow-Derived Mesenchymal Stem Cells in Models of Pulmonary and Extrapulmonary Acute Lung Injury. Cell Transplant. 24(12):2629-2642 (2015).

Loh et al., The Oct4 and Nanog transcription network regulates pluripotency in mouse embryonic stem cells. Nat Genet. 38(4):431-440 (2006).

Lopes Olivares et al., Bone marrow stromal cells improve cardiac performance in healed infarcted rat hearts. Am J Physiol Heart Circ Physiol. 287(2):H464-H470 (2004).

Lopez et al., The Intrapericardial Delivery of Extracellular Vesicles from Cardiosphere-Derived Cells Stimulates M2 Polarization during the Acute Phase of Porcine Myocardial Infarction. Stem Cell Rev Rep. 16(3):612-625 (2020).

Luger et al., Intravenously Delivered Mesenchymal Stem Cells: Systemic Anti-Inflammatory Effects Improve Left Ventricular Dysfunction in Acute Myocardial Infarction and Ischemic Cardiomyopathy. Circ Res. 120(10):1598-1613 (2017).

Luk et al., Inflammatory Conditions Dictate the Effect of Mesenchymal Stem or Stromal Cells on B Cell Function. Front Immunol. 8:1042 (2017).

Luo et al., CD81 Protein is Expressed at High Levels in Normal Germinal Center B cells and in Subtypes of Human Lymphomas. Hum Pathol 41(2):271-280 (2010).

Majeti et al., CD47 is an adverse prognostic factor and therapeutic antibody target on human acute myeloid leukemia stem cells. Cell 138:286-299 (2009).

Maleki et al., Comparison of Mesenchymal Stem Cell Markers in Multiple Human Adult Stem Cells. Int J Stem Cells 7(2):118-126 (2014).

Mangi et al., Mesenchymal stem cells modified with Akt prevent remodeling and restore performance of infarcted hearts. Nat. Med. 9(9):1195-1201 (2003).

Matlung et al., The CD47-SIRPα signaling axis as an innate immune checkpoint in cancer. Immunol Rev 276:145-164 (2017).

Matthay et al., Treatment with allogeneic mesenchymal stromal cells for moderate to severe acute respiratory distress syndrome (START study): a randomised phase 2a safety trial. Lancet Respir Med. 7(2):154-162 (2019).

Mayo Clinic. Allogeneic Bone Marrow Mesenchymal Stem Cells for Patients with Interstitial Lung Disease (ILD) & Connective Tissue Disorders (CTD). https://ClinicalTrials.gov/show/NCT03929120 (2019).

Mayo Clinic. Mesenchymal Stem Cell Therapy for Lung Rejection. https://ClinicalTrials.gov/show/NCT02181712 (2014).

Mayo Clinic. Mesenchymal Stem Cells in the Treatment of Subjects with Advance Chronic Obstructive Pulmonary Disease (COPD). https://ClinicalTrials.gov/show/NCT04047810 (2020).

McHugh et al., Senescence and aging: Causes, consequences, and therapeutic avenues. J. Cell Biol. 217:65-77 (2018).

McIntyre et al., Canadian Critical Care Trials G, Canadian Critical Care Translational Biology G. Cellular Immunotherapy for Septic Shock. A Phase I Clinical Trial. Am J Respir Crit Care Med. 197(3):337-347 (2018).

M.D. Anderson Cancer, Katz Foundation. Mesenchymal Stem Cells (MSCs) for Treatment of Acute Respiratory Distress Syndrome (ARD) in Patients with Malignancies. https://ClinicalTrials.gov/show/NCT02804945 (2017).

Medipost Co., Ltd. PNEUMOSTEM for the Prevention and Treatment of Severe BPD in Premature Infants. https://ClinicalTrials.gov/show/NCT03392467 (2018).

Melichar et al., Comparative Study of Hematopoietic Differentiation between Human Embryonic Stem Cell Lines. PLoS One 6(5): e19854 (2011).

Melief et al., Multipotent stromal cells induce human regulatory T cells through a novel pathway involving skewing of monocytes toward anti-inflammatory macrophages. Stem Cells 31(9):1980-1991 (2013).

Merck KGaA Darmstadt, Germany. Tepotinib with Gefitinib in Subjects with Locally Advanced or Metastatic Non-small Cell Lung Cancer (NSCLC). https://ClinicalTrials.gov/show/NCT01982955 (2013).

Mesoblast, Ltd., Mesoblast Inc. PROCHYMAL™ (Human Adult Stem Cells) for the Treatment of Moderate to Severe Chronic Obstructive Pulmonary Disease (COPD). https://ClinicalTrials.gov/show/NCT00683722 (2008).

Meyer et al., Intracoronary bone marrow cell transfer after myocardial infarction—Eighteen months' follow-up data from the randomized, controlled BOOST (Bone marrow transfer to enhance ST-elevation infarct regeneration) trial. Circulation 113(10):1287-1294 (2006).

Michaels et al., CD47 Blockade as an Adjuvant Immunotherapy for Resectable Pancreatic Cancer. Clin Cancer Res. 24(6):1415-1425 (2018).

Min et al., Long-term improvement of cardiac function in rats after infarction by transplantation of embryonic stem cells. J Thorac Cardiovasc Surg. 125(2):361-369 (2003).

Min et al., Transplantation of embryonic stem cells improves cardiac function in postinfarcted rats. J Appl Physiol. 92(1):288-296 (2002).

Mishra et al., Characterization and functionality of cardiac progenitor cells in congenital heart patients. Circulation 123:364-373 (2011).

Mocini et al., Autologous bone marrow mononuclear cell transplantation in patients undergoing coronary artery bypass grafting. Am. Heart. J. 151(1):192-197 (2006).

(56) References Cited

OTHER PUBLICATIONS

Munoz-Fernandez et al., Human decidual stromal cells secrete C-X-C motif chemokine 13, express B cell-activating factor and rescue B lymphocytes from apoptosis: distinctive characteristics of follicular dendritic cells. Hum Reprod. 27(9):2775-2784 (2012).
Murphy et al., CD4+CD25+ regulatory T cells control innate immune reactivity after injury. J Immunol. 174(5):2957-2963 (2005).
Nair et al., A simple practice guide for dose conversion between animals and human. Journal of Basic and Clinical Pharmacy 7(2):27-31 (2016).
Najar et al., Insights into inflammatory priming of mesenchymal stromal cells: functional biological impacts. Inflamm Res. 67(6):467-477 (2018).
Nakamura et al., Treatment of surgically induced acute liver failure by transplantation of conditionally immortalized hepatocytes. Transplantation 63(11):1541-47 (1997).
Nanfang Hospital of Southern Medical University, Sun Yat-sen University. MSC for Treatment of Interstitial Lung Disease After Allo-HSCT. https://ClinicalTrials.gov/show/NCT02543073 (2014).
Nasef et al., Immunosuppressive effects of mesenchymal stem cells: involvement of HLA-G. Transplantation 84(2):231-237 (2007).
Ng et al., Bioprocess decision support tool for scalable manufacture of extracellular vesicles. Biotechnol Bioeng. 116(2):307-319 (2019).
Oh et al., Cardiac progenitor cells from adult myocardium: homing, differentiation, and fusion after infarction. PNAS USA 100:12313-12318 (2003).
Oldenborg et al., CD47-signal regulatory protein alpha (SIRPalpha) regulates Fcgamma and complement receptor-mediated phagocytosis. J Exp Med. 193(7):855-862 (2001).
Olsen et al., Corporate profile: RoosterBio, Inc. Regen Med. 13(7):753-757 (2018).
Ongstad et al., Immortalization of Human Neonatal C-kit+ Cardiac Progenitor Cells Preserves Their Phenotype and Function at High Passage. Circulation 140(Supp 1):A13869 (2019).
Ortiz et al., Interleukin 1 receptor antagonist mediates the antiinflammatory and antifibrotic effect of mesenchymal stem cells during lung injury. PNAS USA 104(26):11002-11007 (2007).
Ott et al., The adult human heart as a source for stem cells: repair strategies with embryonic-like progenitor cells. Nature Clinical Practice Cardiovascular Medicine 4(Suppl 1):S27-S39 (2007).
Ozbaran et al., Autologous peripheral stem cell transplantation in patients with congestive heart failure due to ischemic heart disease. Eur J Cardiothorac Surg. 25(3):342-350 (2004).
Pagani et al., Autologous skeletal myoblasts transplanted to ischemia-damaged myocardium in humans. Histological analysis of cell survival and differentiation. J Am Coll Cardiol 41(5):879-88 (2003).
Park et al., Dual stem cell therapy synergistically improves cardiac function and vascular regeneration following myocardial infarction. Nat Commun. 10(1):3123 (2019).
Park et al., Stem cell-loaded adhesive immiscible liquid for regeneration of myocardial infarction. J Control Release 321:602-615 (2020).
PCT/US2020/060564 International Search Report and Written Opinion dated Mar. 3, 2021.
Peng et al., Umbilical Cord(UC)-Derived Mesenchymal Stem Cells(MSCs) Treatment for the 2019-novel Coronavirus(nCOV) Pneumonia. https://ClinicalTrials.gov/show/NCT04269525 (2020).
Perin et al., Improved exercise capacity and ischemia 6 and 12 months after transendocardial injection of autologous bone marrow mononuclear cells for ischemic cardiomyopathy. Circulation 110(11 Suppl 1):II213-II218 (2004.
Perin et al., Transendocardial, autologous bone marrow cell transplantation for severe chronic ischemic heart failure. Circulation 07(18):2294-302 (2003).
Petit et al., G-CSF induces stem cell mobilization by decreasing bone marrow SDF-1 and up-regulating CXCR4. Nat Immunol. 3(7):687-694 (2002).
Pompilio et al., Bone Marrow Cell Therapy for Ischemic Heart Disease: The Never Ending Story. Circ Res 117(6):490-493 (2015).
Pourgholaminejad et al., The effect of pro-inflammatory cytokines on immunophenotype, differentiation capacity and immunomodulatory functions of human mesenchymal stem cells. Cytokine 85:51-60 (2016).
Prockop et al., Mesenchymal stem/stromal cells (MSCs): role as guardians of inflammation. Mol Ther. 20(1):14-20 (2012).
Queen's University, Belfast, Norther Ireland Clinical trials Unit, NHS Blood and Transplant. Repair of Acute Respiratory Distress Syndrome by Stromal Cell Administration (REALIST). https://ClinicalTrials.gov/show/NCT03042143 (2019).
Ratajczak et al., Pivotal role of paracrine effects in stem cell therapies in regenerative medicine: can we translate stem cell-secreted paracrine factors and microvesicles into better therapeutic strategies? Leukemia 26(6):1166-1173 (2012).
Ratajczak et al., Stem cell plasticity revisited: CXCR4-positive cells expressing mRNA for early muscle, liver and neural cells 'hide out' in the bone marrow. Leukemia 18(1):29-40 (2004).
Ray et al., Hepatitis C virus core protein promotes immortalization of primary human hepatocytes. Virology 271:197-204 (2000).
Reffelmann et al., Cardiomyocyte transplantation into the failing heart-new therapeutic approach for heart failure? Heart Fail Rev. 8(3):201-211 (2003).
Rokosh et al., Cardiac stem cells in patients with ischaemic cardiomyopathy (SCIPIO): Initial results of a randomised phase 1 trial. Lancet 378:1847-1857 (2011) (Article Retracted).
Rosen et al., Translating stem cell research to cardiac disease therapies: pitfalls and prospects for improvement. Journal of the American College of Cardiology 64(9):922-937 (2014).
Rota et al., Local activation or implantation of cardiac progenitor cells rescues scarred infarcted myocardium improving cardiac function. Circ Res. 103(1):107-116 (2008).
Rubtsov et al., TGFbeta signaling in control of T-cell-mediated self-reactivity. Nat Rev Immunol. 7(6):443-453 (2007).
Rudski et al., Guidelines for the echocardiographic assessment of the right heart in adults: a report from the American Society of Echocardiography endorsed by the European Association of Echocardiography, a registered branch of the European Society of Cardiology, and the Canadian Society of Echocardiography. J Am Soc Echocardiogr. 23(7):685-713 (2010).
Saha et al., Circulating exosomes derived from transplanted progenitor cells aid the functional recovery of ischemic myocardium. Sci Transl Med 11(493):eaau1168 (2019).
Saha et al., Hypoxia-inducible factor 1-alpha enhances the secretome to rejuvenate adult cardiosphere-derived cells. J Thorac Cardiovasc Surg S0022-5223(21):01046-1 (2021).
Sakaguchi et al., Regulatory T Cells and Immune Tolerance. Cell 133:775-787 (2008).
Samsonraj et al., Concise Review: Multifaceted Characterization of Human Mesenchymal Stem Cells for Use in Regenerative Medicine. 6(12):2173-2185 (2017).
Sanganalmath et al., Cell therapy for heart failure: A comprehensive overview of experimental and clinical studies. current challenges, and future directions. Circ. Res. 113(6):810-834 (2013).
Santini et al., Developmental origin and lineage plasticity of endogenous cardiac stem cells. Development 143(8):1242-1258 (2016).
Sanz-Ruiz et al., Rationale and Design of a Clinical Trial to Evaluate the Safety and Efficacy of Intracoronary Infusion of Allogeneic Human Cardiac Stem Cells in Patients with Acute Myocardial Infarction and Left Ventricular Dysfunction: The Randomized Multicenter Double-Blind Controlled CAREMI Trial (Cardiac Stem Cells in Patients with Acute Myocardial Infarction). Circulation Research 121(1):71-80 (2017).
Saxena et al., Stromal cell-derived factor-1 alpha is cardioprotective after myocardial infarction. Circulation 117(17):2224-2231 (2008).
Schachinger et al., Intracoronary bone marrow-derived progenitor cells in acute myocardial infarction. N Engl J Med. 355(12):1210-1221 (2006).
Schmidt et al., Human macrophages induce CD4(+)Foxp3(+) regulatory T cells via binding and re-release of TGF-beta. Immunol Cell Biol. 94(8):747-762 (2016).
Schulman et al., Clinical research skills development program in cell-based regenerative medicine. Stem Cells Translational medicine 4(2):118-122 (2015).

(56) References Cited

OTHER PUBLICATIONS

Selem et al., Stem Cell Therapy for Pediatric Dilated Cardiomyopthay. Curr Cardiol Rep. 15(6):369 (2013).
Shaoxing Second Hospital. Adipose-derived Mesenchymal Stem Cells in Acute Respiratory Distress Syndrome. https://ClinicalTrials.gov/show/NCT01902082 (2012).
Sharma et al., A Deep Proteome Analysis Identifies the Complete Secretome as the Functional Unit of Human Cardiac Progenitor Cells. Circ Res 120(5):816-834 (2017).
Sharma et al., Cardiosphere Derived Cells from Pediatric End-Stage Heart Failure Patients Have Enhanced Functional Activity Due to the Heat Shock Response Regulating the Secretome. Stem Cells 33(4):1213-1229 (2015).
Sharpless et al., How stem cells age and why this makes us grow old. Nat Rev Mol Cell Biol 8(9):703-713 (2007).
Shen et al., Design and Conduct Considerations for First-in-Human Trials. Clin Transl Sci. 12(1):6-19 (2019).
Shenzhen Hornetcorn Bio-technology Company, Ltd., The Second Affiliated Hospital of University of South China. Human Umbilical Cord-Mesenchymal Stem Cells for Pneumoconiosis. https://ClinicalTrials.gov/show/NCT02790762 (2016)).
Shi et al., Immunoregulatory mechanisms of mesenchymal stem and stromal cells in inflammatory diseases. Nat Rev Nephrol. 14(8):493-507 (2018).
Simonson et al., In Vivo Effects of Mesenchymal Stromal Cells in Two Patients with Severe Acute Respiratory Distress Syndrome. Stem Cells Transl Med. 4(10):1199-1213 (2015) [Erratum 2016;5(6):845].
Simpson et al., Engineering Patient-Specific Valves Using Stem Cells Generated from Skin Biopsy Specimens. Ann Thorac Surg 98(3):947-54 (2014).
Simpson et al., Use of Human Embryonic Stem Cell Derived-Mesenchymal Cells for Cardiac Repair. Biotechnol Bioeng 109(1):274-283 (2012).
Smith. A glossary for stem-cell biology. Nature 7097:1059-1060 (2006).
Southwest Hospital China. A Study on Radiation-induced Pulmonary Fibrosis Treated with Clinical Grade Umbilical Cord Mesenchymal Stem Cells. https://ClinicalTrials.gov/show/NCT02277145 (2014).
Southwest Hospital China, Nanjing Chest Hospital. A Study on Pneumoconiosis Treated with Whole-lung Lavage Combined With Mesenchymal Stem Cells. https://ClinicalTrials.gov/show/NCT02668068 (2016).
Stamm et al., Autologous bone-marrow stem-cell transplantation for myocardial regeneration. Lancet 361(9351):45-46 (2003).
Stamm et al., CABG and bone marrow stem cell transplantation after myocardial infarction. Thorac Cardiovasc Surg. 52(3):152-158 (2004).
Stem Cells Arabia. Treatment of COVID-19 Patients Using Wharton's Jelly-Mesenchymal Stem Cells. https://ClinicalTrials.gov/show/NCT04313322 (2020).
Strauer et al., Repair of Infarcted Myocardium by Autologous Intracoronary Mononuclear Bone Marrow Cell Transplantation in Humans. Circulation 106(15):1913-1918 (2002).
Sultana et al., Resident c-kit(+) cells in the heart are not cardiac stem cells. Nature Communications 6:8701 (2015).
Sun Yat-sen University . Human Umbilical Cord Mesenchymal Stem Cells (MSCs) Therapy in ARDS. https://ClinicalTrials.gov/show/NCT03608592 (2018).
Suzuki et al., CD47 expression regulated by the miR-133a tumor suppressor is a novel prognostic marker in esophageal squamous cell carcinoma. Oncol Rep. 28(2):465-472 (2012).
Tang et al., Autologous mesenchymal stem cell transplantation induce VEGF and neovascularization in ischemic myocardium. Regul Pept. 117(1):3-10 (2004).
Tang et al., Intracoronary administration of cardiac progenitor cells alleviates left ventricular dysfunction in rats with a 30-day-old infarction. Circulation 121(2):293-305 (2010).
Tang et al., Long-Term Outcome of Administration of c-kit(POS) Cardiac Progenitor Cells After Acute Myocardial Infarction: Transplanted Cells Do not Become Cardiomyocytes, but Structural and Functional Improvement and Proliferation of Endogenous Cells Persist for at Least One Year. Circ Res. 118(7):1091-1105 (2016).
Tang et al., Mesenchymal stem cells over-expressing SDF-1 promote angiogenesis and improve heart function in experimental myocardial infarction in rats. Eur J Cardiothorac Surg 36:644-650 (2009).
Tateishi-Yuyama et al., Therapeutic angiogenesis for patients with limb ischaemia by autologous transplantation of bone-marrow cells: a pilot study and a randomized controlled trial. Lancet 360(9331):427-435 (2002).
Telukuntla et al., The advancing field of cell-based therapy: insights and lessons from clinical trials. Journal of the American Heart Association 2(5):e000338 (2013).
The Prince Charles Hospital, Cell and Tissue Therapies Western Australia. A Study to Evaluate the Potential of Mesenchymal Stromal Cells to Treat Obliterative Bronchiolitis After Lung Transplantation. https://ClinicalTrials.gov/show/NCT01175655 (2010).
The Prince Charles Hospital, Mater Medical Research Institute. A Study to Evaluate the Potential Role of Mesenchymal Stem Cells in the Treatment of Idiopathic Pulmonary Fibrosis. https://ClinicalTrials.gov/show/NCT01385644 (2010).
Theory et al., Exosomes: composition, biogenesis and function. Nat Rev Immunol 2:569-579 (2002).
Thompson et al., Comparison of intercardiac cell transplantation: autologous skeletal myoblasts versus bone marrow cells. Circulation 108(10)264-271 (2003).
Throne Biotechnologies Inc. Stem Cell Educator Therapy Treat the Viral Inflammation Caused by Severe Acute Respiratory Syndrome Coronavirus 2. https://ClinicalTrials.gov/show/NCT04299152 (2020).
Tomita et al., Improved heart function with myogenesis and angiogenesis after autologous porcine bone marrow stromal cell transplantation. J Thoracic Cardiovasc. Surg. 123:1132--1140 (2002).
Tothova et al., FoxOs are critical mediators of hematopoietic stem cell resistance to physiologic oxidative stress. Cell 128(2):325-339 (2007).
Traister et al., Cardiac regenerative capacity is age- and disease-dependent in childhood heart disease.PLoS One. 13(7):e0200342 (2018).
Traverse et al., Effect of intracoronary delivery of autologous bone marrow mononuclear cells 2 to 3 weeks following acute myocardial infarction on left ventricular function: the LateTIME randomized trial. Cardiovascular Cell Therapy Research Network. JAMA 306(19):2110-2119 (2011).
Traverse et al., Effect of the use and timing of bone marrow mononuclear cell delivery on left ventricular function after acute myocardial infarction. JAMA 308(22):2380-2389 (2012).
Tribouilloy et al., Quantification of tricuspid regurgitation by measuring the width of the vena contracta with Doppler color flow imaging: a clinical study. J Am Coll Cardiol. 36(2):472-478 (2000).
Tse et al., Angiogenesis in ischaemic myocardium by intramyocardial autologous bone marrow mononuclear cell implantation. Lancet 361:47-49 (2003).
U.S. Appl. No. 14/712,793 Office Action dated Jun. 9, 2017.
U.S. Appl. No. 14/712,793 Office Action dated Sep. 27, 2016.
U.S. Appl. No. 15/728,061 Office Action dated Aug. 19, 2019.
U.S. Appl. No. 15/728,061 Office Action dated Jul. 22, 2020.
U.S. Appl. No. 15/728,061 Office Action dated Mar. 23, 2020.
U.S. Appl. No. 17/191,526 Office Action dated Aug. 20, 2021.
U.S. Appl. No. 17/191,526 Office Action dated Feb. 15, 2022.
U.S. Appl. No. 17/191,526 Office Action dated May 5, 2021.
U.S. Appl. No. 17/191,526 Office Action dated Sep. 26, 2022.
Vagnozzi et al., An acute immune response underlies the benefit of cardiac stem cell therapy. Nature. 577(7790):405-409 (2020).
Viera et al., Increased Myocardial Retention of Mesenchymal Stem Cells Post-MI by Pre-Conditioning Exercise Training. Stem Cell Rev Rep. 66(4):730-741 (2020).
Vincinanza et al., Adult cardiac stem cells are multipotent and robustly myogenic: c-kit expression is necessary but not sufficient for their identification. Cell Death Differ. 24(12):2101-2116 (2017).
Vogel et al., Stem cells in the management of heart failure: what have we learned from clinical trials? Expert Review of Cardiovascular Therapy 13(1):75-83 (2015).

(56) References Cited

OTHER PUBLICATIONS

Volarevic et al., Mesenchymal stem cell-derived factors: Immunomodulatory effects and therapeutic potential. Biofactors. 43(5):633-644 (2017).
Vujic et al., Molecular mechanisms of heart regeneration. Semin Cell Dev Biol. 100:20-28 (2019).
Walter et al., Mesenchymal stem cells: mechanisms of potential therapeutic benefit in ARDS and sepsis. Lancet Respir Med. 2(12):1016-26 (2014).
Wang et al., Plasticity of mesenchymal stem cells in immunomodulation: pathological and therapeutic implications. Nature Immunology 15(11):1009 (2014).
Wang et al., Transplantation of autologous endothelial progenitor cells may be beneficial in patients with idiopathic pulmonary arterial hypertension: a pilot randomized controlled trial. J Am Coll Cardiol. 49(14):1566-1571 (2007).
Wehman et al., Cardiac Progenitor Cells Enhance Neonatal Right Ventricular Function After Pulmonary Artery Banding. Ann Thorac Surg 104(6):2045-2053 (2017).
Wehman et al., Intracoronary Stem Cell Delivery to the Right Ventricle: A Preclinical Study. Semin Thorac Cardiovasc Surg 28(4):817-824 (2016).
Wehman et al., Mesenchymal stem cells preserve neonatal right ventricular function in a porcine model of pressure overload. Am J Physiol Heart Cir Physiol 310:H1816-H1826 (2016).
Wehman et al., Pediatric End-Stage Failing Hearts Demonstrate Increased Cardiac Stem Cells. Ann Thorac Surg 100(2):615-622 (2015).
Wehman et al., Stem Cell Therapy for Congenital Heart Disease: Toward Translation. Cardiol Young 25(02):58-66 (2015).
Wehman et al., The Emergence of Stem Cell Therapy for Congenital Heart Disease Patients. Circ Res 116(4):566-569 (2015).
Weirather et al., Foxp3+ CD4+ T cells improve healing after myocardial infarction by modulating monocyte/macrophage differentiation. Circ Res. 115(1):55-67 (2014).
Weiss et al., A placebo-controlled, randomized trial of mesenchymal stem cells in COPD. Chest. 2013;143(6):1590-1598 (2013).
Weiss et al., Immunomodulation by Mesenchymal Stem Cells (MSCs): Mechanisms of Action of Living, Apoptotic, and Dead MSCs. Front Immunol. 10:1191 (2019).
Werner et al., Cultivation of immortalized human hepatocytes HepZ on macroporous CultiSpher G microcarriers. Biotechnol Bioeng 68(1):59-70 (2000).
Westerheide et al., Celastrols as inducers of the heat shock response and cytoprotection. J Biol Chem. 279(53):56053-60 (2004).
Westerheide et al., Triptolide, an Inhibitor of the Human Heat Shock Response That En-hances Stress-induced Cell Death. J Biol Chem 281(14):9616-9622 (2006).
Whitley et al., Heat shock proteins: A review of the molecular chaperones. J Vasc Surg 29:748-51 (1999).
Williams et al., Enhanced effect of combining human cardiac stem cells and bone marrow mesenchymal stem cells to reduce infarct size and to restore cardiac function after myocardial infarction. Circulation 127(2):213-223 (2013).
Williams et al., Mesenchymal stem cells: biology, pathophysiology, translational findings, and therapeutic implications for cardiac disease. Circulation Research 109(8):923-940 (2011).
Willingham et al., The CD47-signal regulatory protein alpha (SIRPa) interaction is a therapeutic target for human solid tumors. PNAS USA 109:6662-6667 (2012).
Wilson et al., Mesenchymal stem (stromal) cells for treatment of ARDS: a phase 1 clinical trial. The Lancet Respiratory Medicine 3(1):24-32 (2015).
Wollert et al., Intracoronary autologous bone-marrow cell transfer after myocardial infarction: the BOOST randomized controlled clinical trial. Lancet 364(9429):141-148 (2004).
Wu et al., Adipose Tissue-Derived Mesenchymal Stem Cells Have a Heterogenic Cytokine Secretion Profile. Stem Cells Int. 2017:4960831 (2017).
Wuhan Union Hospital China, Wuhan Hamilton Bio-technology Co. Ltd, China. Study of Human Umbilical Cord Mesenchymal Stem Cells in the Treatment of Novel Coronavirus Severe Pneumonia. https://ClinicalTrials.gov/show/NCT04273646 ; 2020.
Wynn et al., A small proportion of mesenchymal stem cells strongly express functionally active CXCR4 receptor capable of promoting migration to bone marrow. Blood 104:2643-2645 (2004).
Xijing Hospital, Changhai Hospital, Southwest Hospital, China. The Safety and Effects of Mesenchymal Stem Cell (MSCs) in the Treatment of Rheumatoid Arthritis. https://ClinicalTrials.gov/show/NCT03798028 (2017).
Xu et al., Micro-RNA-34a contributes to the impaired function of bone marrow-derived mononuclear cells from patients with cardiovascular disease. J Am Coll Cardiol. 59(23):2107-2117 (2012).
Yagi et al., Reactive bone marrow stromal cells attenuate systemic inflammation via sTNFR1. Mol Ther. 18(10):1857-1864 (2010).
Yamaguchi et al., Stromal cell-derived factor-1 effects on ex vivo expanded endothelial progenitor cell recruitment for ischemic neovascularization. Circulation 107(9):1322-1328 (2003).
Yang et al., Cell size and growth rate are major determinants of replicative lifespan. Cell Cycle 10(1):144-155 (2011).
Yin et al., Manufacturing of primed mesenchymal stromal cells for therapy. Nat Biomed Eng. 3(2):90-104 (2019).
Yuan et al., Aggregation of Culture Expanded Human Mesenchymal Stem Cells in Microcarrier-based Bioreactor. Biochem Eng J. 131:39-46 (2018).
Zacchigna et al., Paracrine effect of regulatory T cells promotes cardiomyocyte proliferation during pregnancy and after myocardial infarction. Nature Communications 9(1):2432 (2018).
Zhang et al., Disrupting CD47-SIRPalpha axis alone or combined with autophagy depletion for the therapy of glioblastoma. Carcinogenesis. 39(5):689-699 (2018).
Zhang et al., HIF-1 regulates CD47 expression in breast cancer cells to promote evasion of phagocytosis and maintenance of cancer stem cells. PNAS USA 112(45):E6215-E6123 (2015).
Zhang et al., Long-term effects of bone marrow mononuclear cell transplantation on left ventricular function and remodeling in rats. Life Sci 74(23):2853-2864 (2004).
Zheng et al., Mesenchymal stromal cell-derived extracellular vesicles: regenerative and immunomodulatory effects and potential applications in sepsis. Cell Tissue Res. 374(1):1-15 (2018).
Zheng, et al., Treatment of acute respiratory distress syndrome with allogeneic adipose-derived mesenchymal stem cells: a randomized, placebo-controlled pilot study. Respiratory research 15(1):39 (2014).
Zhong et al., The current status and future of cardiac stem/progenitor cell therapy for congenital heart defects from diabetic pregnancy. Pediatr Res 83(1-2):275-282 (2018).
Zhu et al., Human bone marrow mesenchymal stem cells express multiple hematopoietic growth factors. Zhongguo Shi Yan Xue Ye Xue Za Zhi 11(2):115-119 (2003) (English Abstract).
Zhu et al., Safety and efficacy of autologous endothelial progenitor cells transplantation in children with idiopathic pulmonary arterial hypertension: open-label pilot study. Pediatr Transplant. 12(6):650-655 (2008).
Zimmermann et al., Cardiac tissue engineering for replacement therapy. Heart Fail Rev. 8(3):259-269 (2003).
Zimmet et al., Emerging role for bone marrow derived mesenchymal stem cells in myocardial regenerative therapy. Basic Res Cardiol. 100(6):471-481 (2005).
Zwetsloot et al., Cardiac Stem Cell Treatment in Myocardial Infarction: A Systematic Review and Meta-Analysis of Preclinical Studies. Circ Res. 118(8):1223-1232 (2016).
Co-pending U.S. Appl. No. 18/734,139, inventor Kaushal; Sunjay, filed Jun. 5, 2024.
EP20829738.2 European Patent Office Summons to attend Oral Proceedings dated Aug. 29, 2024.
U.S. Appl. No. 18/459,685 Notice of Allowance dated Oct. 18, 2024.
U.S. Appl. No. 18/459,685 Office Action dated Feb. 8, 2024.

* cited by examiner

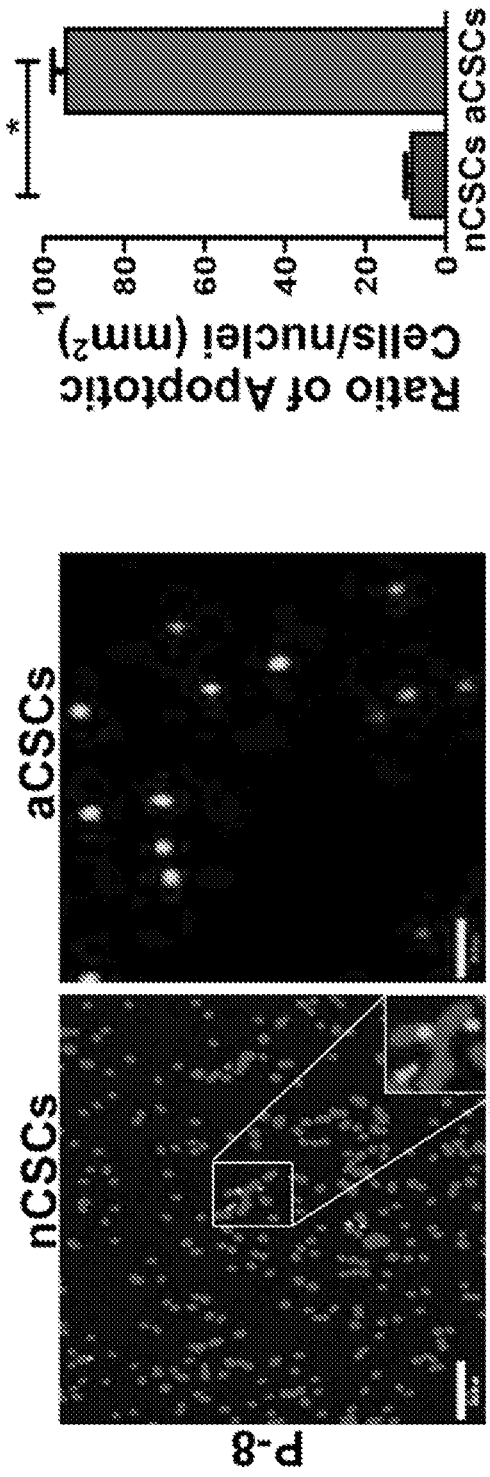

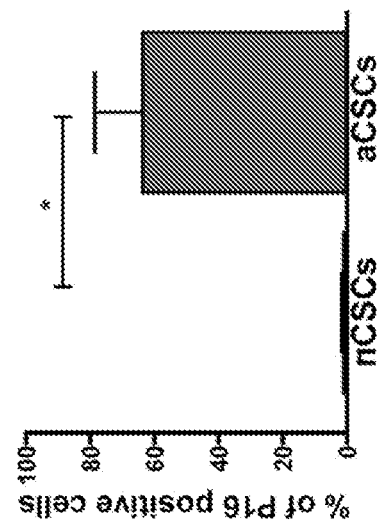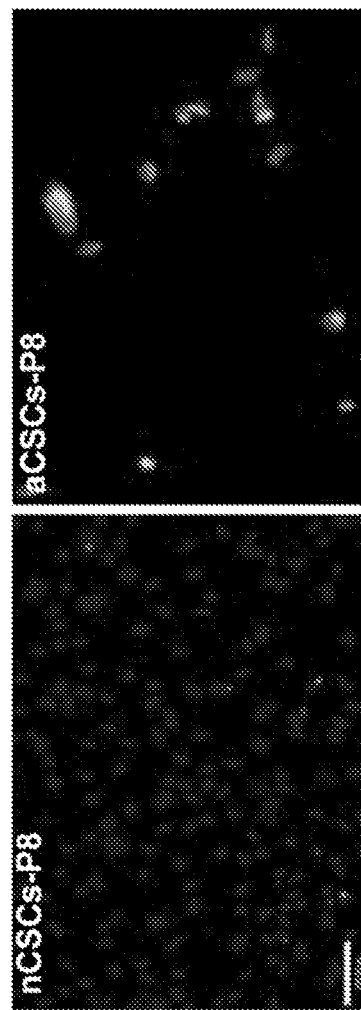
FIG. 4B

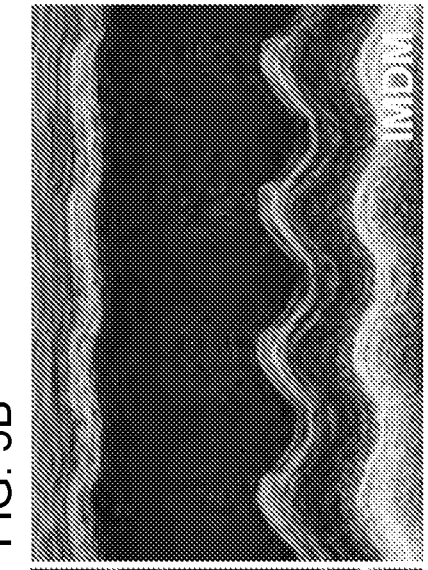
FIG. 5A / FIG. 5B
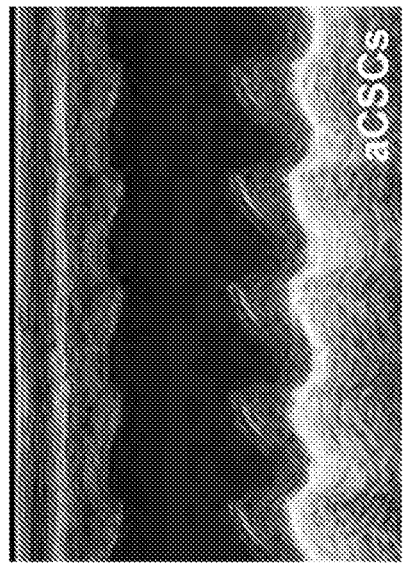
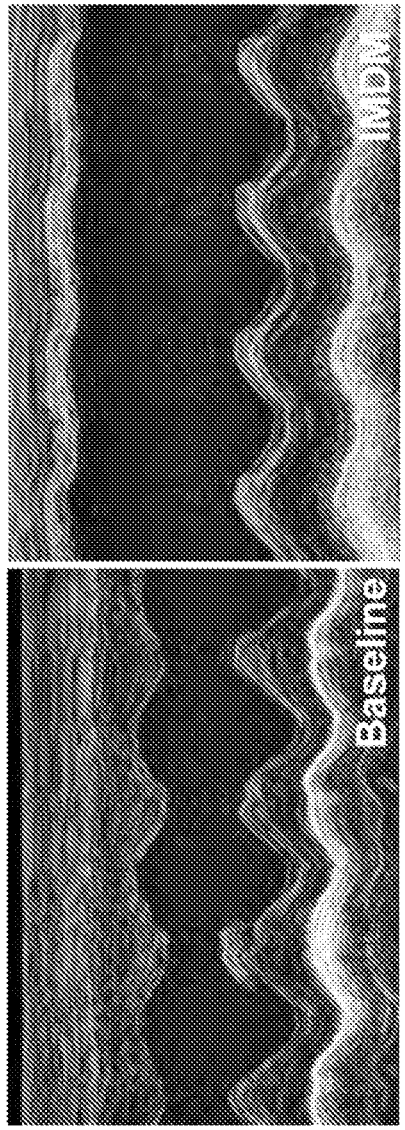
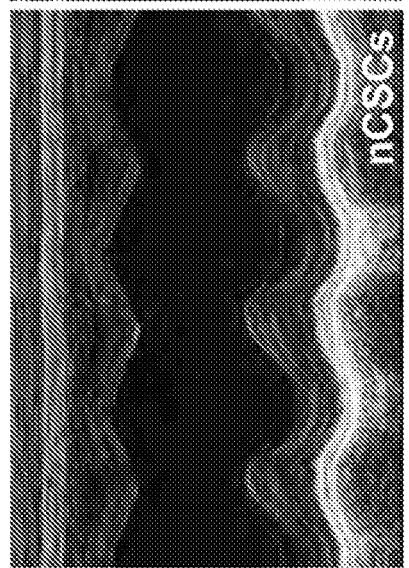
FIG. 5C / FIG. 5D

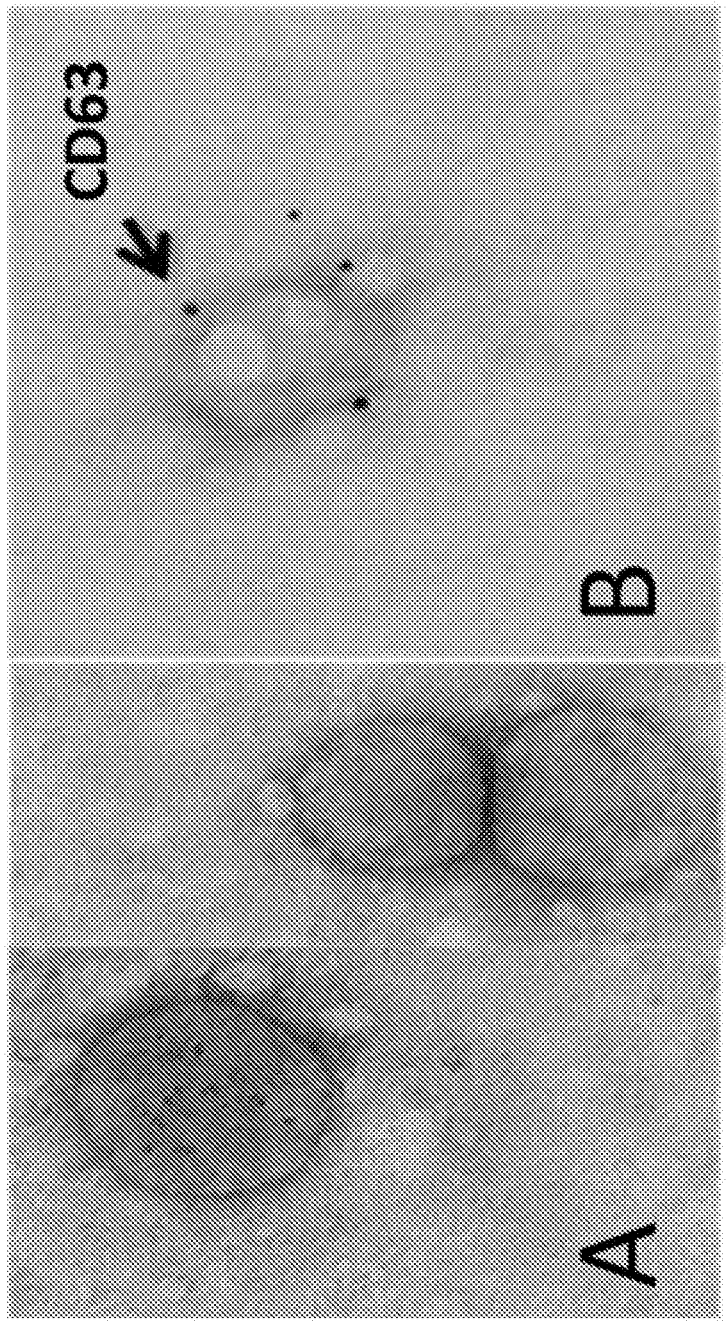

CARDIAC STEM CELLS FOR CARDIAC REPAIR

CROSS-REFERENCE TO RELATED APPLICATIONS

This application is a continuation of U.S. patent application Ser. No. 17/191,526, filed Mar. 3, 2021, now U.S. Pat. No. 11,633,431, which is a continuation of U.S. patent application Ser. No. 15/728,061, filed Oct. 9, 2017, now U.S. Pat. No. 10,967,007, which is a divisional of U.S. patent application Ser. No. 14/712,793, filed May 14, 2015, which claims priority to U.S. Provisional Patent Application Ser. No. 61/993,055, filed May 14, 2014, and to U.S. Provisional Patent Application Ser. No. 62/010,742, filed Jun. 11, 2014, all of which applications are incorporated by reference herein in their entirety.

STATEMENT REGARDING FEDERALLY SPONSORED RESEARCH OR DEVELOPMENT

This invention was made with government support under Grant Number HL097069 awarded by the National Institutes of Health. The government has certain rights in the invention.

TECHNICAL FIELD

The field of the disclosure concerns at least the fields of cell biology, molecular biology, and medicine, including cardiology.

BACKGROUND

Heart disease in adults is a leading cause of death and there is an increasing number of children with heart failure owing to advances in surgical techniques for congenital heart defects and post-operative ICU care (Go, et al., 2014; Go, et al., 2014). It has been recently shown that in clinical studies transplantation of resident cardiac stem cells can regenerate/remodel human myocardium, leading to improvements in cardiac function as indicated by improvements in ejection fraction, reduced scar size, reduced end diastolic and systolic volumes and improvements in quality of life and NYHA class (Garbern, et al., 2013). These and other preclinical in vivo data indicate that a particular population of resident human cardiac stem cells (hCSCs), distinguished by their c-kit+ phenotype, provides substantial benefit in repairing the failing heart following intracoronary infusion (Bolli, et al., 2011; Bolli, et al., 2013; Tang, et al., 2010).

It was originally thought that hCSCs differentiate into cardiomyocytes and repopulate the damaged myocardium with new cardiomyocytes able to replenish lost cells (Bolli, et al., 2011; Tang, et al., 2010; Beltrami, et al., 2003; Chugh, et al., 2012). However, it is now recognized that differentiation of the hCSCs into mature cardiac lineage cells occurs at very low frequency, which was tested in a well-established rodent myocardial infarction (MI) model in which the left anterior descending artery is permanently ligated (Pagani, et al., 2003). Therefore, other mechanisms seem responsible for the regenerative/remodeling capacity of hCSCs (Bergmann, et al., 2009; Kajstura et al., 2012).

There is need for compositions and methods for regenerating functional myocardium in adults and children with cardiac medical conditions, such as heart failure caused by damaged myocardial tissue, for example.

BRIEF SUMMARY

Embodiments of the disclosure concern methods and compositions related to particular cells for treatment of one or more cardiac medical conditions. Although any cardiac medical condition may be treated with such compositions and methods, in specific embodiments the condition is a cardiac condition that would benefit from regenerating or remodeling of the myocardium. In certain embodiments, the methods and compositions facilitate or enhance the regenerative or remodeling capacity of human cardiac stem cells (hCSCs). Embodiments of the disclosure encompass methods and compositions concerning cells that are mesenchymal cells from a myocardium of a mammal, including a human. In specific embodiments, the cells are c-kit+ mesenchymal cells and have characteristic markers.

In particular embodiments, particular c-kit+ cardiac stem cells are provided to an individual for treatment of one or more cardiac medical conditions, although in specific embodiments a conditioned medium from the cells is provided to an individual for treatment of a cardiac medical condition, and in particular embodiments, secretomes from the cells are provided to an individual for treatment of a cardiac medical condition.

In one embodiment there is, as a composition of matter, a composition comprising an isolated plurality of human cardiac cells that have two or more of the following characteristics: c-kit+, CD90+, CD105+, CD31−, CD34−, CD45−, and tryptase negative. In one embodiment there is, as a composition of matter, a pharmaceutical composition comprising an isolated plurality of human cardiac cells that have two or more of the following characteristics: c-kit+, CD90+, CD105+, CD31−, CD34−, CD45−, and tryptase negative; and a pharmaceutically acceptable carrier. In specific embodiments, the cells have one, two, three, or more of the following characteristics: GATA4+, CD44+, CD31−, CD34−, CD45−, CD140−, CD106−, tryptase-, CD80−, CD86−, HLA Class I+, and HLA Class II−.

In certain embodiments, cells of the disclosure are isolated from the heart of a neonatal individual, including a pediatric or non-pediatric individual. In specific embodiments, the individual has a cardiac medical condition. In certain embodiments, the individual has normal myocardium. The cells may be from the myocardium of a pediatric individual with end stage heart failure, in some embodiments. The myocardium may come from a neonatal individual with congenital heart disease.

In specific embodiments, the cells secrete exosomes that are CD63+. The cells may secrete one or more cytokines; one or more pro-angiogenic factors; and/or one or more VEGF-A, HGF, SCF, SDF-1α, and ANG-1. The cells may express VEGF-A and/or SDF-1α. In particular embodiments, the cells have activation of expression of one or more components of the heat shock response. The cells may have activation of expression of HSF-1, HSP60, and/or HSP70. In particular embodiments, the cells are manipulated to express Hsp70, Hsp27, ISL-1, or a combination thereof. In particular embodiments, the cells are manipulated to increase secretion of SDF-1α, VEGF-A, PGDF-A, IL-6, FGF-2, or a combination thereof. The cells may be suspended in a medium comprising one or more heat shock response inducers, including one or more heat shock response inducers are selected from the group consisting of celastrol, triptolide, and a combination thereof.

In one embodiment, there is a method of treating an individual for a cardiac medical condition, comprising the step of providing to the individual a therapeutically effective amount of a composition of the disclosure, medium conditioned by a composition of the disclosure, exosomes secreted by a composition of the disclosure, or a combination thereof. In particular embodiments, the composition, medium, exosomes, or a combination thereof are provided to an hypoxic environment in the heart of the individual. In particular embodiments, the cardiac medical condition is heart failure, cardiomyopathy, or congenital heart disease.

In one embodiment, there is conditioned medium from the cells of the disclosure, and the conditioned medium and/or components thereof may be provided in therapeutic amounts to the individual instead of the cells themselves. In another embodiment, there are exosomes from the cells of the disclosure, and therapeutic amounts of the exosomes and/or components thereof may be provided to the individual instead of the cells. A mixture of conditioned medium and exosomes may be provided in therapeutic amounts to the individual instead of the cells.

BRIEF DESCRIPTION OF THE DRAWINGS

FIGS. 3A, 3B, 3C, 3D, 3E, 3F, 3G, 3H, 3I, and 3J show a comparative analysis of growth potential of nCSCs and aCSCs at P3 and P8.

FIGS. 4A, 4B, and 4C illustrate a comparative analysis of nCSCs and aCSCs at P3 and P8.

FIGS. 5A, 5B, 5C, 5D, 5E, 5F, 5G, 5H, 5I, 5J, 5K, and 5L point out cardiac function measured by echocardiography.

FIGS. 15A and 15B depict Isolation of exosomes from c-kit+ cardiac stem cells.

DETAILED DESCRIPTION

Figure 1A:
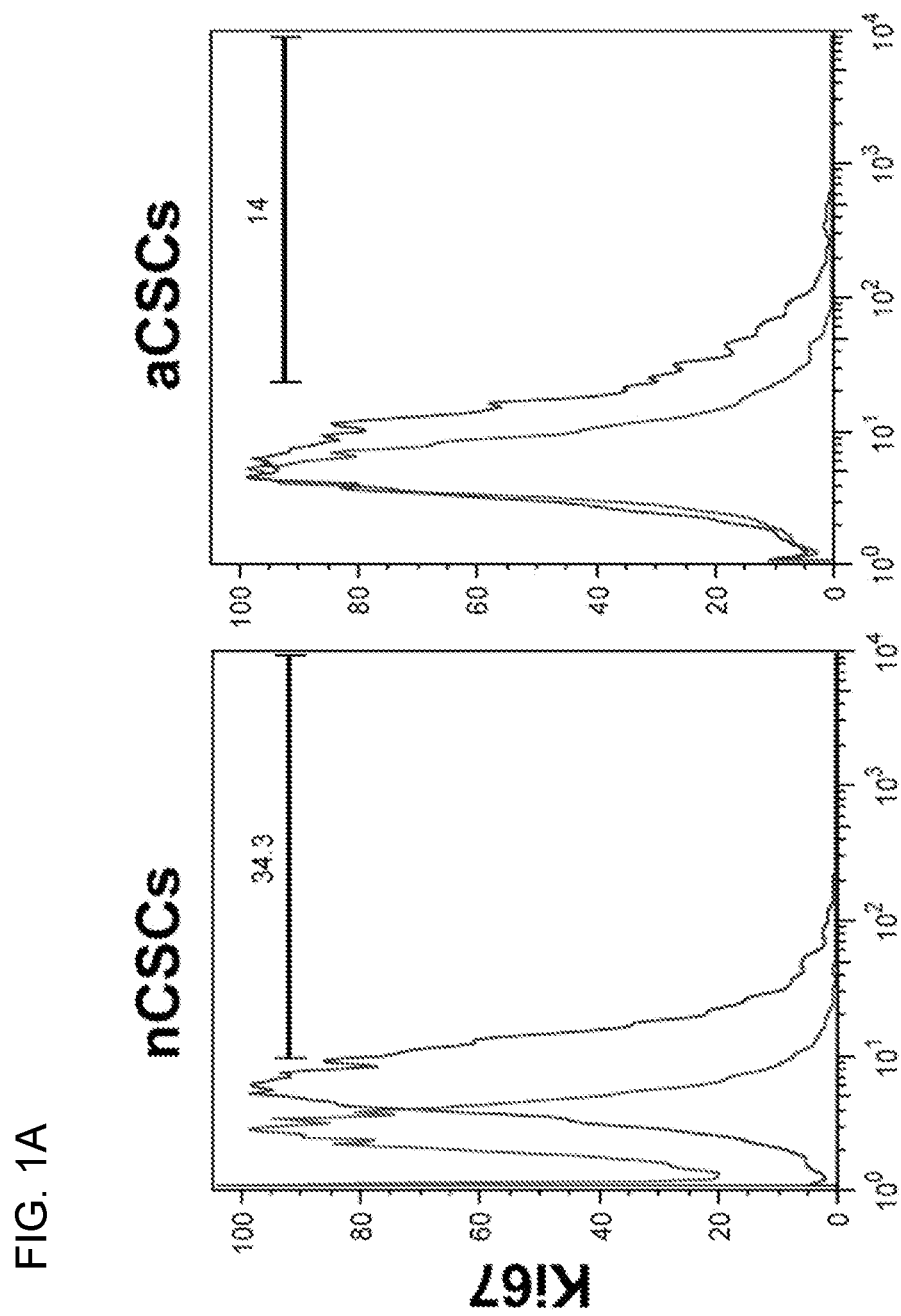
FIGS. 1A, 1B, 1C, and 1D display a comparative analysis of proliferative and clonogenic potential of neonatal cardiac stem cells (nCSCs) and adult cardiac stem cells (aCSCs).

In keeping with long-standing patent law convention, the words "a" and "an" when used in the present specification in concert with the word comprising, including the claims, denote "one or more." Some embodiments may consist of or consist essentially of one or more elements, method steps, and/or methods of the disclosure. It is contemplated that any method or composition described herein can be implemented with respect to any other method or composition described herein, and embodiments which are disclosed and still obtain a like or similar result without departing from the spirit and scope of the subject matter are encompassed in the invention.

The term "cardiac stem cells" as used herein may be defined as cells derived from cardiac tissue and are clonogenic, multipotent, and self-renewing. In specific embodiments, these cardiac stem cells express one or more of the following: c-kit+, CD90, CD105, and are negative for one or more of the following: CD31, C34, CD45, and tryptase.

I. Cells of the Disclosure and Secretomes Thereof

Embodiments of the disclosure concern mammalian cells that provide a therapeutic function for an individual in need thereof. In specific embodiments, the cells are human cardiac stem cells (hCSCs) and are useful for a therapeutic function in a mammalian heart. In specific embodiments, the cells have the activity of regenerative or remodeling capacity themselves upon administration to a heart in vivo and/or have the activity for facilitating regenerative or remodeling capacity of endogenous cells and/or tissue in a human myocardium upon administration to a heart in vivo. In specific embodiments, the cells are capable of eliciting a bystander effect, such that upon delivery of the cells to the myocardium in vivo, the cells secrete one or more proteins that enhance regeneration or remodeling of endogenous cells and/or tissues.

The cells may be from any source, including adult, child or infant, but in specific embodiments the source of the cardiac stem cells are from a neonatal or pediatric individual or from an individual in utero. In particular embodiments, the cells are not adult cardiac stem cells. The cells may be obtained from an individual in need of therapeutic use using progeny of the same cells or the cells may be obtained from another individual. The cells may originate from a donated heart of a neonatal or pediatric individual or from the heart of a living neonatal or pediatric individual. The cells may be provided commercially to the individual in need or may be provided to a medical facility or practitioner overseeing medical care of the individual in need.

Embodiments of the disclosure encompass cells that are mesenchymal cells from a myocardium of a mammal, including a human. In particular embodiments, the cardiac stem cells may have a specific genotype and/or phenotype. The cells may be provided to an individual in need thereof following determination of a certain genotype or phenotype of the cells that is suitable for the intended function of the cells upon therapeutic use, in certain embodiments. In specific embodiments, the cells are c-kit+ mesenchymal cells, and in particular embodiments the cells are c-kit+, CD90+, CD105+, and CD34−. In other embodiments, the cells also have one, two, three, or more of the following characteristics: GATA4+, CD44+, CD31−, CD140−, CD106−, tryptase−, CD80−, CD45−, CD86−, HLA Class I+, and HLA Class II−.

In some embodiments, the cells naturally secrete one or more proteins or factors that are beneficial for regeneration or remodeling of localized cells or tissue. Such proteins or factors may be of any kind, but in specific embodiments they are cytokines, pro-angiogenic factors, growth factors, transcription factors, miRNAs and so forth. In some embodiments, the cells secrete one or more of VEGF-A, HGF, SCF, SDF-1α, and ANG-1. In certain embodiments, the cells are manipulated to increase secretion of SDF-1α, VEGF-A, PGDF-A, IL-6, FGF-2, or a combination thereof such manipulation may be by any manner, but in specific embodiments the manipulation encompasses recombinant technology for increase in expression of one of these factors. Another manipulation is with exposure of the cells to heat shock factor that have been shown to increase the secretion of the cytokines.

In some embodiments, the cells naturally express one or more proteins or factors that are beneficial for regeneration or remodeling of localized cells or tissue, either directly or indirectly. For example, the cells may express VEGF-A and/or SDF-1α. The cells may have activation of expression of HSF-1, HSP60, and/or HSP70, either naturally or by manipulation of the cells to increase expression of HSF-1, HSP60, and/or HSP70. In specific embodiments, the cells are manipulated to express Hsp70, Hsp27, ISL-1, or a combination thereof The cells may be present as a plurality of cells, and the plurality may be 100% homogeneous with respect to the desired cardiac stem cells, or the plurality may have less than 100% homogeneity, such as having 99, 98, 97, 96, 95, 94, 93, 92, 91, 90, 85, 80, 75, 70, 65, 60, 55, 50, 45, 40, 35, 30, or 25% homogeneity, or having at least that percentage of homogeneity, with respect to the desired cardiac stem cells. Cells may be utilized in methods when they are present in a plurality have 100% homogeneity or having less than 100% homogeneity, such as having 99, 98, 97, 96, 95, 94, 93, 92, 91, 90, 85, 80, 75, 70, 65, 60, 55, 50, 45, 40, 35, 30, or 25% homogeneity.

The cells may be stored for a period of time before their use, including under suitable medium, temperature, and oxygen level conditions, or they may be used without significant storage time. In specific embodiments, the storage cell medium comprises one or more heat shock response inducers.

The cells may have allogeneic properties, such as defined by having low levels of MHC Class II, or co-stimulator proteins CD88 and CD80. These cells do not initiate an immune response when transplanted into another patient's immune system. In such a case, the cells may be used as an off the shelf product for clinical applications.

In particular embodiments, cells from a young individual have demonstrated strong regenerative abilities when compared to adult derived cells. This increased regenerative ability is due to a stronger secretome by the young cells, in specific embodiments. This implies that the young cells may be a preferable allogenic product, in at least specific embodiments.

II. Methods of Isolation of the Cells

One of skill in the art recognizes that there are routine methods to obtain cells from a human myocardium and further process the cells thereafter. In particular embodiments, there are methods of isolating the desired hCSCs by obtaining tissue from a human myocardium (such as obtained from the right atrial appendage of the heart), including from a neonatal or pediatric myocardium, such as by biopsy. The myocardium may be from an individual with end stage heart failure or from an individual with congenital heart disease, and in these cases the myocardium may or may not be normal. The extracted tissue may be exposed to particular medium while separating singular cells from their tissue, including by cutting the tissue, such as in the presence of collagenase. In specific embodiments, the tissue and tissue fragments are allowed to sediment while in a medium, and the supernatant is obtained. Cells may be collected from the supernatant and suspended in culture medium for a suitable period of time. Following this, the desired c-kit+ hCSCs are isolated therefrom. The isolation of the desired c-kit+ hCSCs may occur by any means, but in specific embodiments the c-kit+ cells are obtained by exposing the collected cells to a substrate comprising a surface with a moiety that binds c-kit, such as a c-kit antibody. The substrate may be a plate, bead, or column, for example. In certain embodiments, once the desired c-kit+ hCSCs are isolated, they may be cultured under standard conditions, including suitable passaging. The medium for culture of the cells may or may not be substantially identical to the medium employed when the cells are delivered to an individual.

The medium may or may not comprise one or more heat shock response inducers.

III. Methods of Use of Cells of the Disclosure and Secretomes Thereof

Methods of the disclosure include use of certain c-kit+ cells (and, in some embodiments, c-kit+ mesenchymal cells) for therapy for at least one cardiac medical condition in an individual in need thereof. In specific embodiments, the cells are useful for cardiac medical conditions wherein tissue repair, regeneration, and/or replacement would be therapeutically useful. In specific embodiments, a therapeutically effective amount of the cells as described herein are provided to the individual, and in particular embodiments the cells are delivered to the individual locally. The individual receiving the cells may be of any gender or age. The individual may or may not be diagnosed by a medical practitioner with the cardiac medical condition. In certain embodiments, the individual has a personal or family medical history of a cardiac medical condition. The individual may be at risk for a cardiac medical condition, such as smoking; High LDL and/or low HDL; uncontrolled hypertension; physical inactivity; obesity (more than 20% over one's ideal body weight); uncontrolled diabetes; high C-reactive protein; or a combination thereof. In specific embodiments an individual is provided one or more methods of the disclosure upon diagnosis of a certain genotype or phenotype for the individual.

The human CSCs may be provided to an individual wherein the cells are autologous, allogeneic, or xenogeneic with respect to the individual. In cases wherein the cells are allogeneic or xenogeneic, the cells may be processed to reduce the risk of rejection of the cells by the individual's immune system. However, in specific embodiments the cells' general makeup allow them not to elicit an immune response. If there is an immune response generated, one can use autologous based cells for clinical application.

Upon isolation of the desired cells from the source individual, and prior to their delivery to the individual in need thereof, the cells may be further modified, such as through manipulation for recombinant expression of one or more expression constructs, further culturing and/or enrichment, and so forth. Such practices are routine in the art. An expression construct transfected into the cells may be of any kind, but in specific embodiments, the construct expresses a cytokine, pro-angiogenic factor, growth factor, transcription factor, and so forth. In specific embodiments the construct expresses VEGF-A, HGF, SCF, SDF-1α, ANG-1, HSF-1, HSP60, HSP70, Hsp70, Hsp27, ISL-1, PGDF-A, IL-6, FGF-2, or a combination thereof and/or expresses another protein that directly or indirectly increases their expression. The cells may be exposed to one or more agents to increase secretion and/or expression of certain proteins.

In certain embodiments, a therapeutically effective amount of cells as described herein are utilized in one or more treatment methods, although in specific embodiments the individual instead receives therapeutically effective amounts of conditioned media from the cells; part of all of the secretome from the cells; one or more secreted proteins or other factors (such as miRNAs) from the cells; or a combination thereof. The use of any one of these components or combinations facilitates proliferation of endogenous cardiomyocytes upon their use, in specific embodiments. In certain embodiments, the use of any one of these components or combinations allow for regenerating or remodeling of the myocardium. In certain embodiments, the use of any one of these components or combinations facilitates or enhances the regenerative or remodeling capacity of hCSCs that are endogenous to the individual.

In particular embodiments, when cells are provided to the individual, they may be provided in conjunction with (in the same or a different composition) or at the same time as another therapeutic moiety. That is, in specific embodiments the cells are administered to the individual at substantially the same time as one or more agents that enhance the function of the cells upon their administration in vivo. Such an agent may be of any kind, but in specific embodiments the agent is one or more heat shock response inducers.

Although in some cases one or more agents are provided to the individual at substantially the same time as the cells, in specific embodiments the cells are exposed to one or more agents prior to their delivery to the individual, wherein the agent(s) enhances the function of the cells upon in vivo delivery. In specific embodiments, the cells are exposed to one or more agents while in culture. The cells may be exposed to the agents one or multiple times, and when the cells are passaged in culture, the agents may or may not be present in subsequent media. In specific embodiments, the agents enhance therapeutic use of the cells by increasing expression of one or more genes, increasing secretion of one or more proteins or other factors (such as miRNAs), or a combination thereof. In particular embodiments, the genes or proteins are cytokines, pro-angiogenic factors, growth factors, transcription factors, micro RNAs (miRs), and exosomes (small carrying vehicles that contain concentrated proteins and miRs), and so forth. In certain embodiments, the agents are heat shock response inducers.

In one embodiment, a particular and therapeutically effective number of the cells will be provided to the individual. In specific embodiments, 1-20 million cells are provided, but in some embodiments the number of millions of cells is 1-19, 1-18, 1-17, 1-16, 1-15, 1-14, 1-13, 1-12, 1-11, 1-10, 1-9, 1-8, 1-7, 1-6, 1-5, 1-4, 1-3, 1-2, 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-20, 3-19, 3-18, 3-17, 3-16, 3-15, 3-14, 3-13, 3-12, 3-11, 3-10, 3-9, 3-8, 3-7, 3-6, 3-5, 3-4, 4-20, 4-19, 4-18, 4-17, 4-16, 4-15, 4-14, 4-13, 4-12, 4-11, 4-10, 4-9, 4-8, 4-7, 4-6, 4-5, 5-20, 5-19, 5-18, 5-17, 5-16, 5-15, 5-14, 5-13, 5-12, 5-11, 5-10, 5-9, 5-8, 5-7, 5-6, 6-20, 6-19, 6-18, 6-17, 6-16, 6-15, 6-14, 6-13, 6-12, 6-11, 6-10, 6-9, 6-8, 6-7, 7-20, 7-19, 7-18, 7-17, 7-16, 7-15, 7-14, 7-13, 7-12, 7-11, 7-10, 7-9, 7-8, 8-20, 8-19, 8-18, 8-17, 8-16, 8-15, 8-14, 8-13, 8-12, 8-11, 8-10, 8-9, 9-20, 9-19, 9-18, 9-17, 9-16, 9-15, 9-14, 9-13, 9-12, 9-11, 9-10, 10-20, 10-19, 10-18, 10-17, 10-16, 10-15, 10-14, 10-13, 10-12, 10-11, 11-20, 11-19, 11-18, 11-17, 11-16, 11-15, 11-14, 11-13, 11-12, 12-20, 12-19, 12-18, 12-17, 12-16, 12-15, 12-14, 12-13, 13-20, 13-19, 13-18, 13-17, 13-16, 13-15, 13-14, 14-20, 14-19, 14-18, 14-17, 14-16, 14-15, 15-20, 15-19, 15-18, 15-17, 15-16, 16-20, 16-19, 16-18, 16-17, 17-20, 17-19, 17-18, 18-20, 18-19, or 19-20, for example.

In particular embodiments, one can isolate the proteins, miRs, or any other factors within the conditioned media. In specific embodiments, from the conditioned media the secretome itself or one or more components of the secretome, such as proteins and exosomes, are provided to an individual. Exosomes have very strong regenerative abilities by themselves and may be provided therapeutically to the individual rather than the cells. In specific embodiments, the conditioned media is provided therapeutically to the individual rather than the cells.

IV. Cardiac Medical Conditions

Embodiments of the disclosure concern treatment of one or more cardiac medical conditions. Particular aspects for such embodiments result in reversal of one or more cardiac medical conditions or improvement of at least one symptom of one or more cardiac medical conditions. In exemplary embodiments, the cardiac medical condition is heart failure. The heart failure may be the result of one or more causes, including coronary artery disease, heart attack, high blood pressure, faulty heart valves, cardiomyopathy (such as caused by disease, infection, alcohol abuse and the toxic effect of drugs, such as cocaine or some drugs used for chemotherapy), idiopathic cardiomyopathy, congenital heart disease and/or genetic factors.

Particular but exemplary indications of embodiments of the disclosure include at least applications for heart failure, including congestive heart failure; prevention of ventricular remodeling; and/or cardiomyopathy. Other indications may also include coronary artery disease, ischemic heart disease, valvular heart disease, etc. In specific embodiments, methods and compositions of the disclosure provide myocardial regeneration that is sufficient to treat, including reverse, an established cardiac medical condition such a cardiomyopathy or congestive heart failure.

In cases where the individual has cardiomyopathy, the cardiomyopathy may be ischemic or non-ischemic cardiomyopathy. The cardiomyopathy may be caused by long-term high blood pressure, heart valve problems, heart tissue damage from a previous heart attack, chronic rapid heart rate, metabolic disorders, nutritional deficiencies, pregnancy, alcohol abuse, drug abuse, chemotherapy drugs, viral infection, hemochromatosis, genetic condition, elevated cholesterol levels, or a combination thereof. Cardiomyopathy may also have no identified cause, i.e., idiopathic cardiomyopathy.

V. Combination Therapy

In some embodiments, an individual who has received therapy of the disclosure, or is receiving, or will receive therapy of the disclosure, is also provided another therapy for the cardiac medical condition. The therapy of the present disclosure may precede or follow the other treatment by intervals ranging from minutes to hours to days to weeks or months. In embodiments where the other agent and the instant therapy are given separately to the individual, one would generally ensure that a significant period of time did not expire between the time of each delivery, such that the therapy of the disclosure and the additional therapy would still be able to exert an advantageously combined effect on the individual. In such instances, it is contemplated that one may contact the individual with both modalities simultaneously or within minutes of each other or within about 1-12, 6-12, or 12-24 h of each other, for example. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

In specific embodiments, the therapy of the present disclosure and the additional therapy are provided at the same time or at different times. The separate entities may be within the same compositions or they may be comprised in separate compositions. In cases wherein the therapy of the present disclosure and the second therapy are provided at different times, they may be separated by any suitable range in times, such as minutes, hours, days, or weeks. In embodiments wherein they are provided separately, the order of delivery of two (or more) therapies may be of any suitable order, including delivery of cells, secretomes, and/or conditioned media prior to or subsequent to another therapy.

Examples of other treatments to be employed with the therapy of the disclosure include one or more of the following: ACE Inhibitors, Aldosterone Inhibitor, Angiotensin II Receptor Blocker (ARBs); Beta-Blockers, Calcium Channel Blockers, Cholesterol-Lowering Drugs, Digoxin, Diuretics, Inotropic Therapy, Potassium or Magnesium, Vasodilators, anticoagulant medication, aspirin, surgery, VAD implantation, VAT, coronary bypass, percutaneous coronary intervention (PCI) or a combination thereof.

VI. Kits of the Disclosure

Any of the c-kit+ CSCs described herein may be comprised in a kit. The kit may additionally comprise other agents for therapy of a cardiac medical condition.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing the one or more compositions in close confinement for commercial sale. Such containers may include injection or blow-molded plastic containers into which the desired vials are retained. In specific embodiments the cells are delivered in a frozen state and may or may not be provided in plastic vials.

The composition may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

The kits of the present disclosure will also typically include a means for containing the vials in close confinement for commercial sale, such as, e.g., injection and/or blow-molded plastic containers into which the desired vials are retained.

In particular embodiments, the kit comprises reagents and/or tools for determining that an individual has a cardiac medical condition. In some embodiments, the kit comprises one or more additional therapies for a cardiac-related medical condition, such as one or more of ACE Inhibitor, aldosterone inhibitor, angiotensin II receptor blocker (ARBs); beta-blocker, calcium channel blocker, cholesterol-lowering drug, digoxin, diuretics, inotropic therapy, potassium, magnesium, vasodilator, anticoagulant medication, aspirin, TGF-beta inhibitor, and a combination thereof.

VI. Pharmaceutical Compositions

Embodiments of pharmaceutical compositions of the present disclosure comprise an effective amount of cardiac stem cells dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that comprises cells are known to those of skill in the art in light of the present disclosure, as exemplified by Remington: The Science and Practice of Pharmacy, 21st Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. Except insofar as any conventional carrier is incompatible with the active ingredient, its use in the pharmaceutical compositions is contemplated.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1 Neonatal C-Kit-Positive Cardiac Progenitor Cells for Treatment of Cardiac Medical Conditions Cardiac medical conditions, including heart failure, are in need of effective therapy for patients of any age, including babies, children, and adults. In particular, compositions and methods are needed for regenerating functional myocardium in adults and children with cardiac medical conditions, such as heart failure caused by damaged myocardial tissue, for example.

Described in this Example is a novel population of c-kit+ hCSCs that can be administered to patients in need thereof to treat damaged myocardium. The c-kit+ hCSCs induce regeneration and/or remodeling of the damaged myocardium and improve cardiac function.

In certain embodiments, the phenotypic characterization of the newly isolated c-kit+ CSCs described herein is c-kit+, CD90+, GATA4+, CD44+, CD105+, CD34−, CD31−, CD140−, CD106− and tryptase−. This is distinct from previously published hCSCs, which were phenotypically characterized as c-kit+, lin−, and not positive for CD90, CD105, GATA4. The newly described c-kit+ CSCs are a subtype of a mesenchymal cell within the myocardium.

The isolation of the c-kit+ cells is performed using a novel protocol in which c-kit+ cells are isolated using specific c-kit+ magnetic beads (as an example of a cell-isolating substrate) and cultured in embryonic stem cell medium, as described in this Example.

The c-kit+ cells isolated from neonatal patients with congenital heart disease but putatively normal myocardium induce greater recovery of ventricular function in a rodent myocardial infarction (MI) model than do c-kit+ cells isolated from adult patients with normal myocardium.

Medium conditioned by human neonatal c-kit+ cells and administered to infarcted myocardium in rodents induced functional recovery of the myocardium (indicated by measurement of ejection fraction) as effectively as transplanted neonatal-derived c-kit+ cells. This suggests the transplanted neonatal-derived c-kit+ cells induce functional recovery by exerting a dominant paracrine effect on surrounding tissue.

In addition, the data suggest that under hypoxic in vitro conditions that replicate conditions in ischemic myocardium, neonatal c-kit+ cells significantly secreted higher levels of paracrine factors in comparison to adult c-kit+ cells. These data suggest that c-kit+ cells have a unique secretome that governs their functional activity.

The data shows that in fact c-kit+ cells secrete exosomes which are characterized by their specific CD63+ expression as shown by fluorescence-activated cell sorting (FACS) and electron microscopy properties. It was further shown that injection of the exosomes isolated from medium conditioned by neonatal c-kit+ mesenchymal cells induced functional recovery in the MI rodent model in comparison to the control medium alone. Also demonstrated is that exosomes isolated from medium conditioned by neonatal c-kit+ induced neovascularization in endothelial tube formation assays in vitro. Based on these observations, in one embodiment exosomes isolated from medium conditioned by neonatal c-kit+ cells induce recovery of the MI myocardium more strongly than exosomes derived from medium conditioned by adult derived c-kit+ cells due to preferential expression of cytokines and mIRs by the neonatal cells versus the adult cells.

The neonatal c-kit+ cells described herein can be used as an "off the shelf" stem cell product for allogeneic transplantation into damaged myocardium in patients in need of such treatment. Because these cells express mesenchymal stem cell markers, they have the innate ability to be immunologically privileged in the manner of immunologically privileged bone marrow-derived mesenchymal cells. The neonatal c-kit+ cells are HLA Class I+, HLA Class II−, CD80−, and CD86−.

Figure 1B:
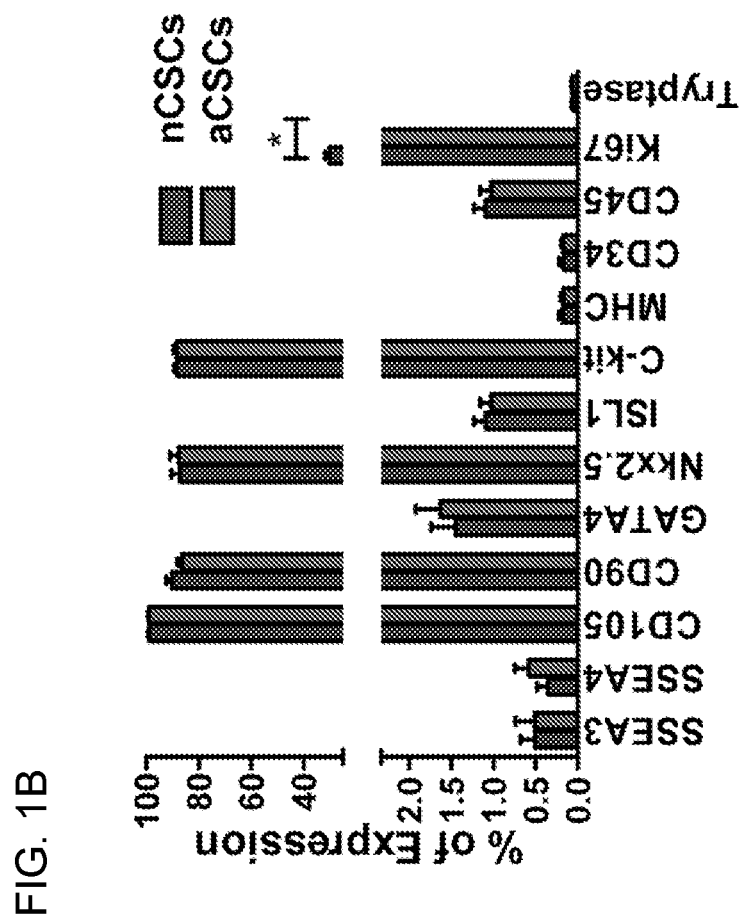
Figure 1C:
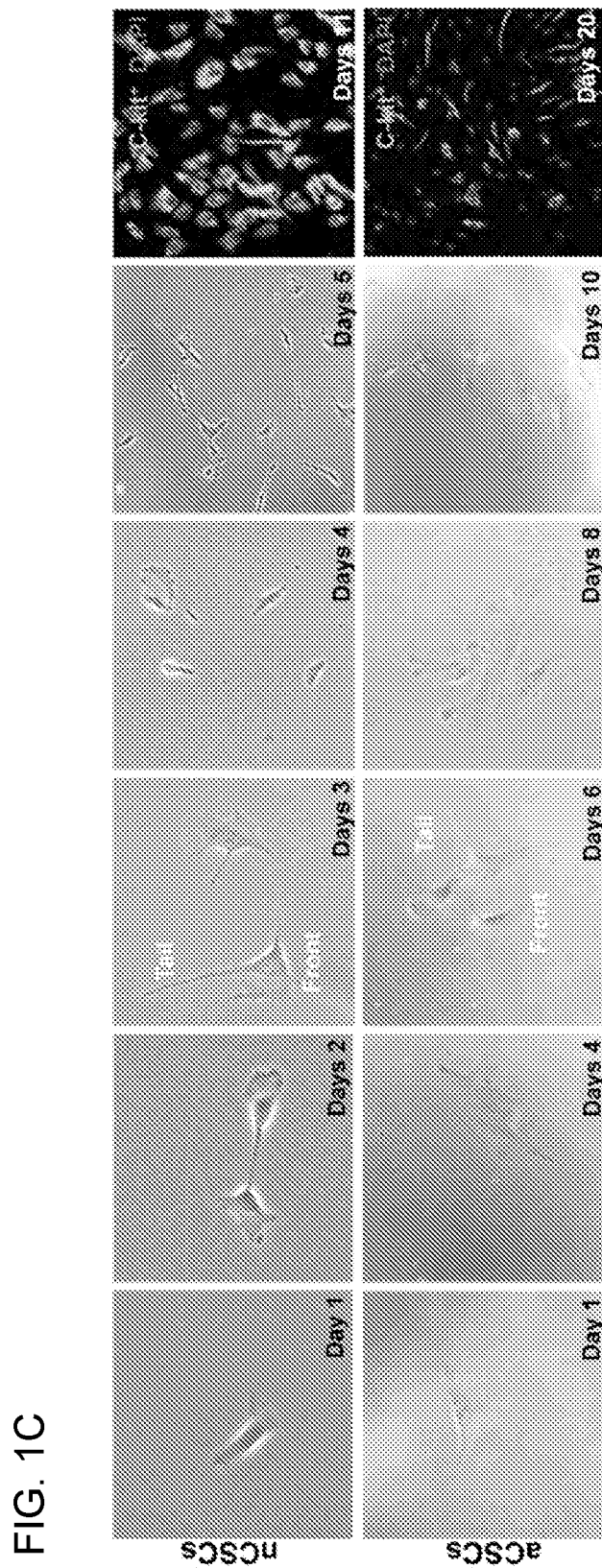
Figure 1D:
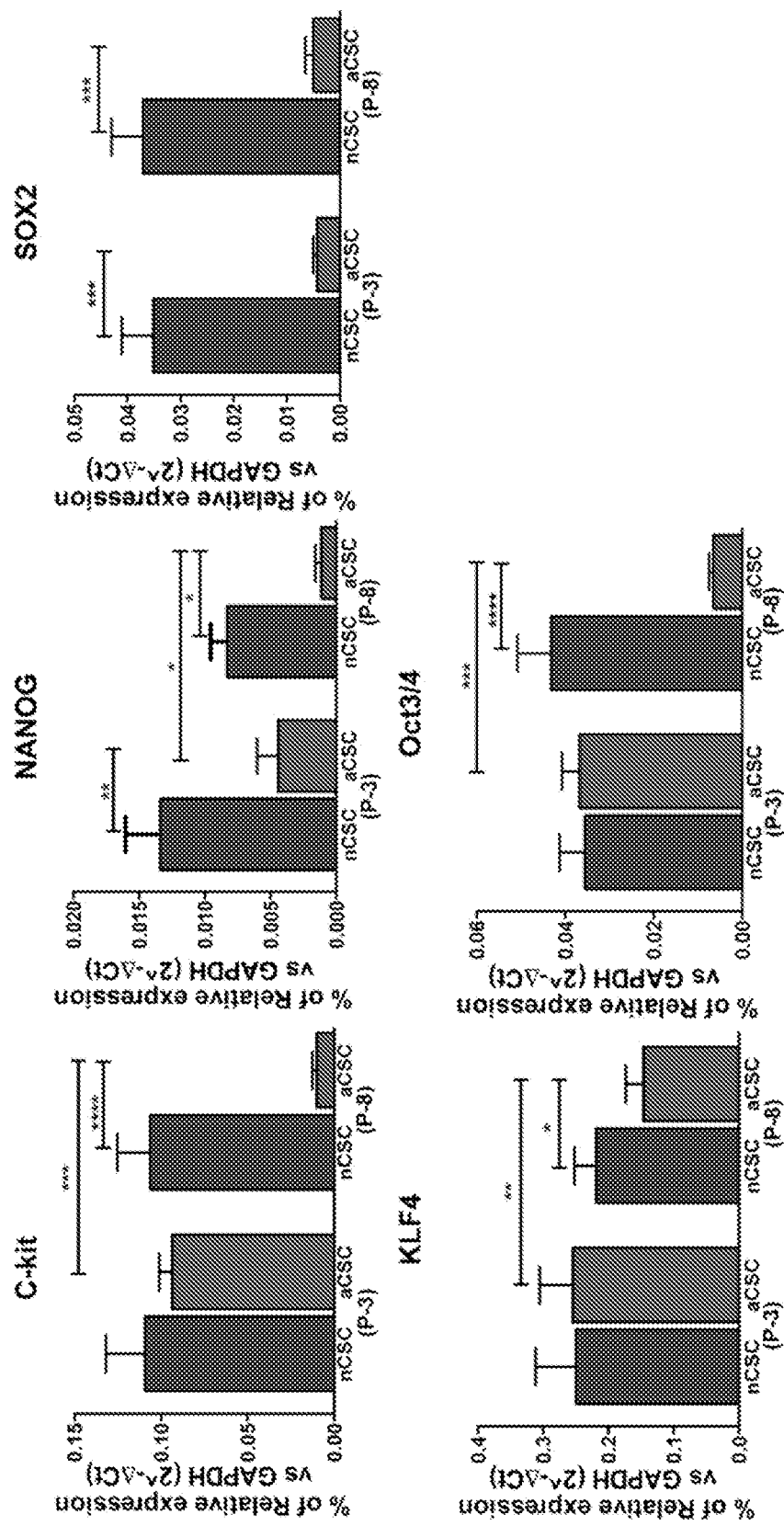

FIGS. 1A-ID show comparative analysis of proliferative and clonogenic potential of nCSCs and aCSCs. FIG. 1A). Representative flow cytometry panel. Higher expression of Ki67 was observed in nCSCs and compared to aCSCs at passage P3. Conjugated isotype control is depicted as red. FIG. 1B). Quantification of expression of various cardiac stem cells specific surface or transcription factors. The expression of ki67 was significantly higher (*P<0.05) in nCSCs as compared to aCSCs. FIG. 1C). nCSCs showed a higher clonogenic capacity as compared to aCSCs. nCSCs underwent 14 population doubling levels (PDL) by day 11 (20,000 cells in 96 wells), while aCSCs underwent 12 PDL by day 20 (5000 cells in 96 wells). Moreover, a decline in the expression of c-kit was also observed in aCSCs as seen by immunostaining of C-kit (green in a colorized version), DAPI (blue in a colorized version). FIG. 1D). Quantitative PCR was performed to identify the expression of various stem cell specific markers. The expression levels of c-kit, KLF4, OCT3/4 (POU5F1) were similar at Passage 3 (P3) in nCSCs and aCSCs, the expression of these genes was significantly low in aCSCs by passage 8 (P8). The expression of NANOG and SOX2 was significantly low in aCSCs as compared to nCSCs at P3 and P8 both. Data was analyzed using GRAPHPAD® software and represented as mean±SEM. (*P<0.05, P<0.01, *P<0.001 and ****P<0.0005). Grouped data was analyzed by 2-way ANOVA followed by Bonferroni post hoc analysis.

Figure 2A:
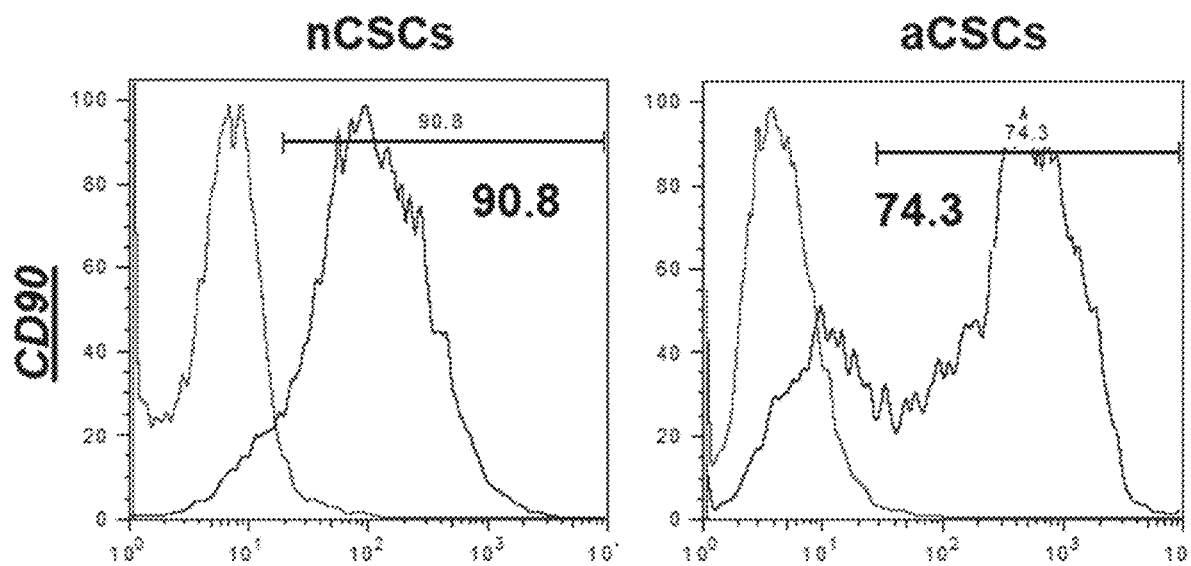
FIGS. 2A, 2B, 2C, 2D, 2E, 2F, 2G, 2H, 2I, 2J, 2K, 2L, and 2M depict C-kit+ cardiac cells specific marker profile of nCSCs and aCSCs.
Figure 2B:
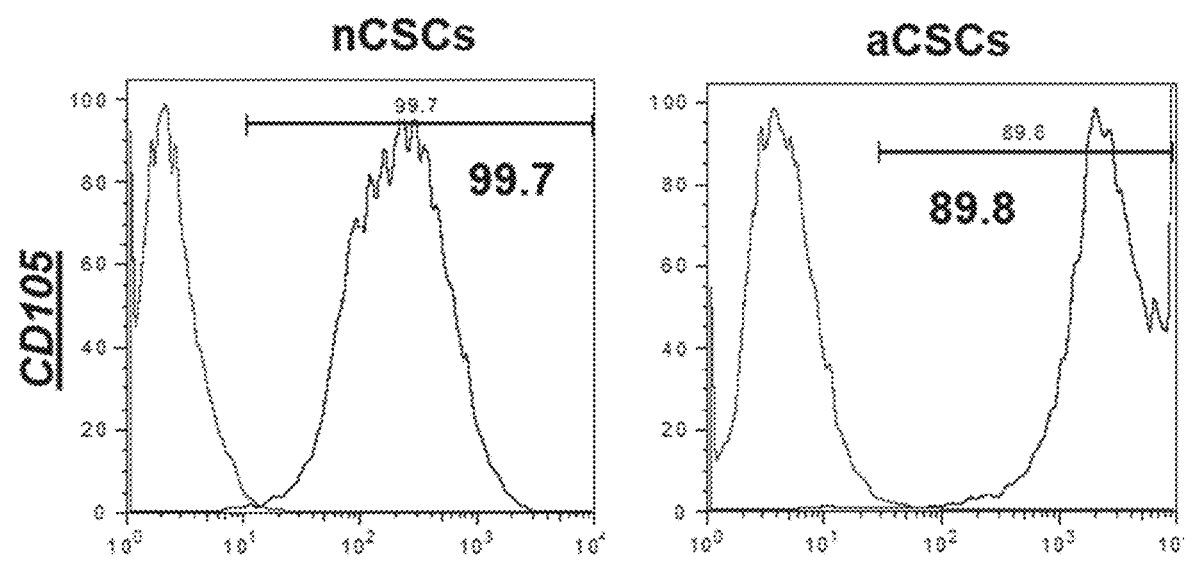
Figure 2C:
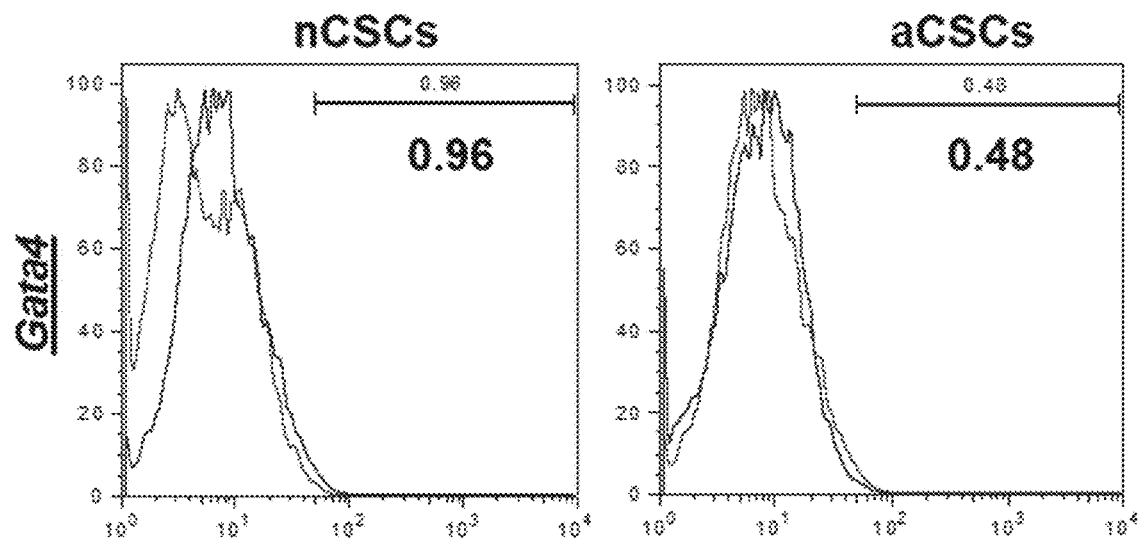
Figure 2D:
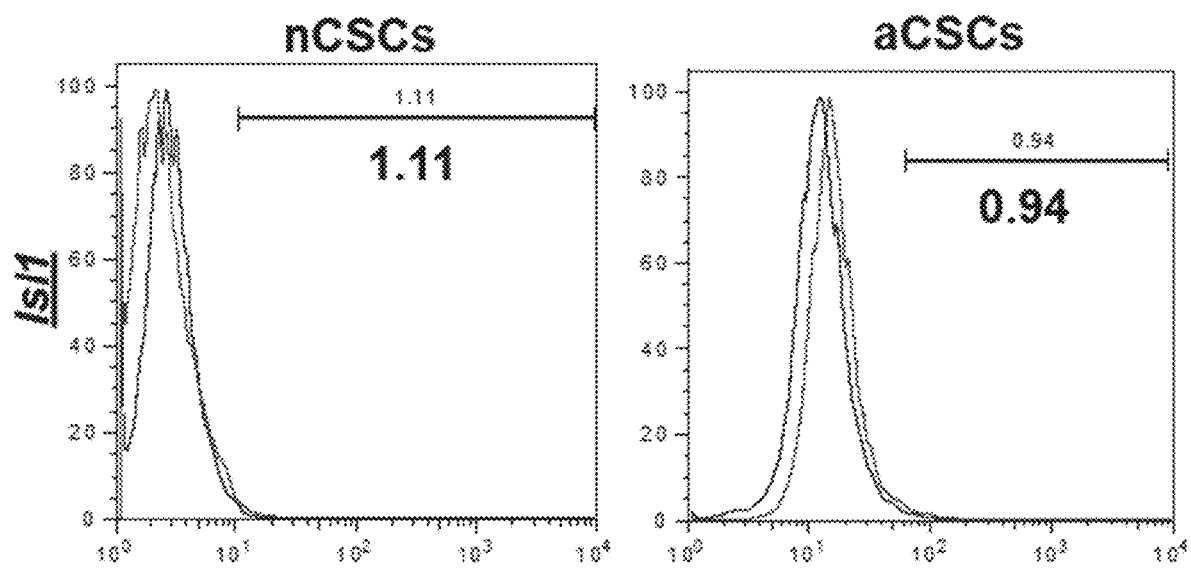
Figure 2E:
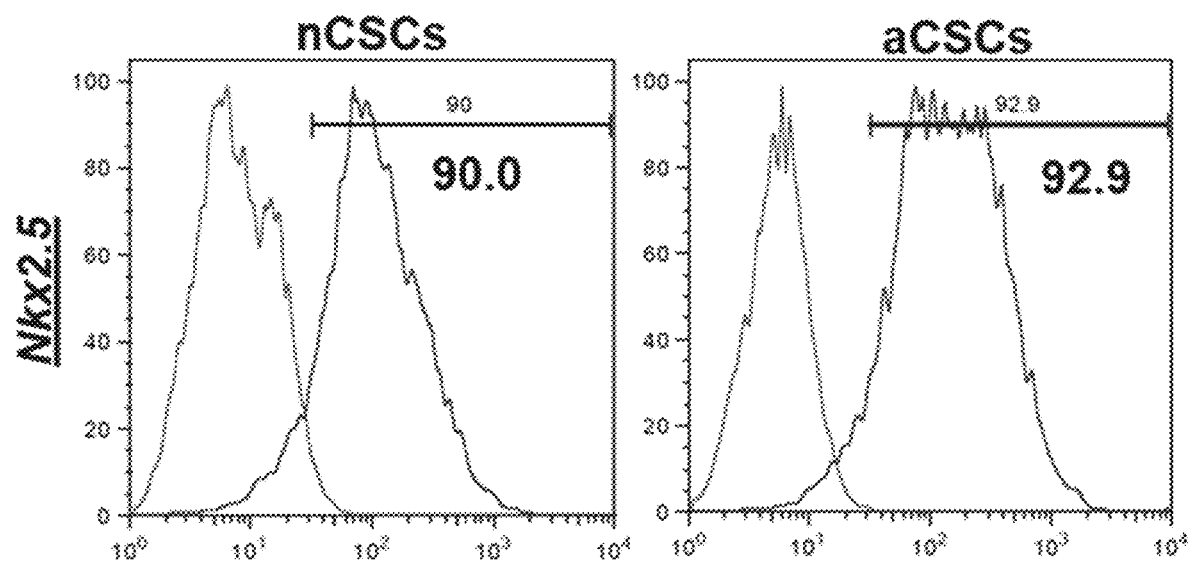
Figure 2F:
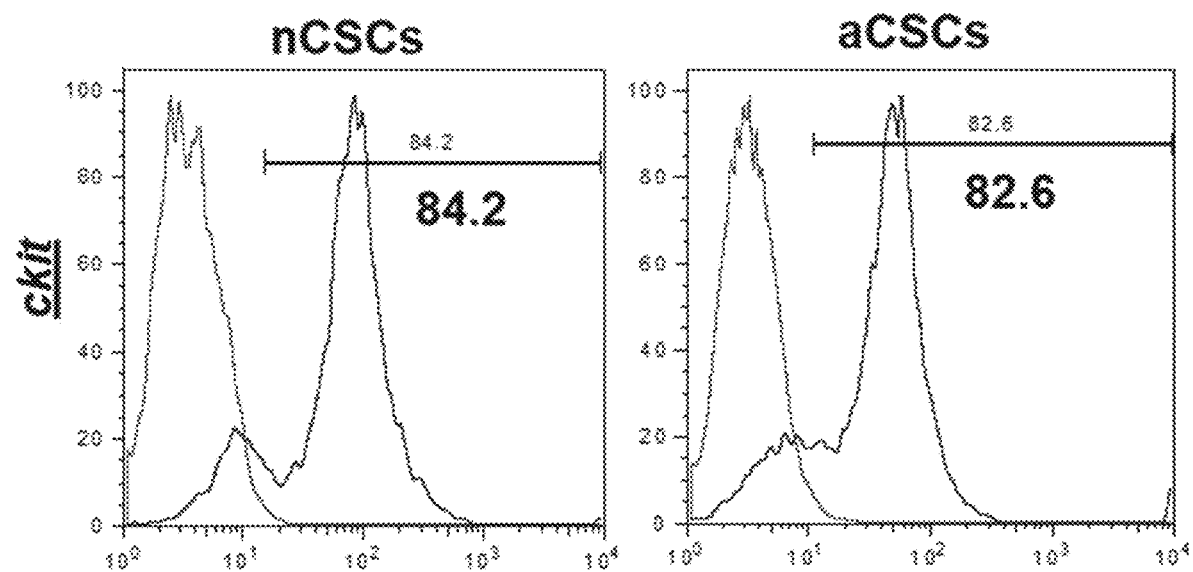
Figure 2G:
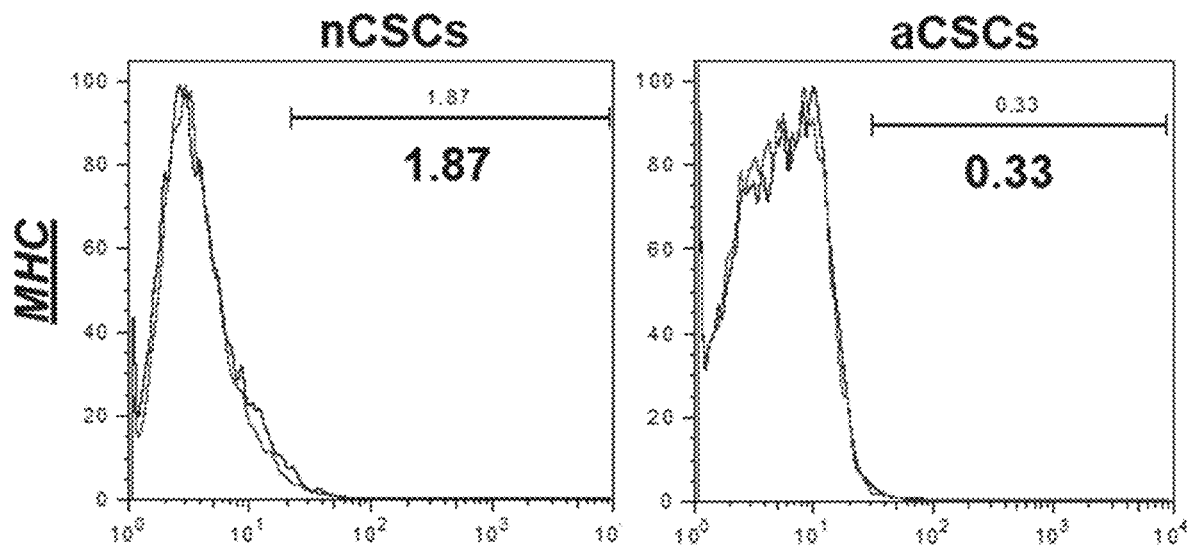
Figure 2H:
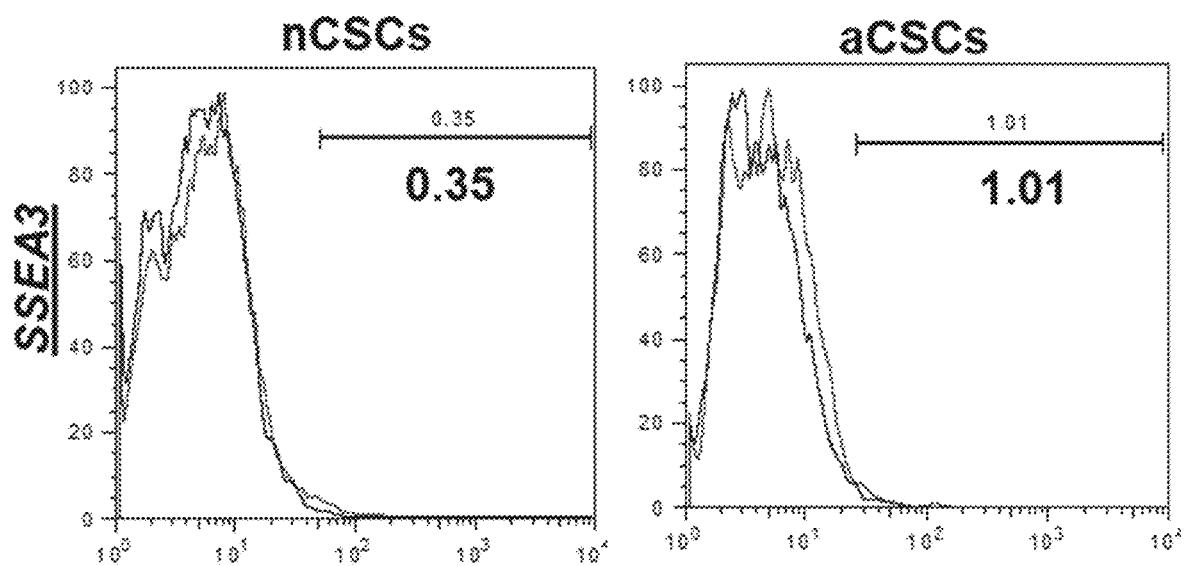
Figure 2I:
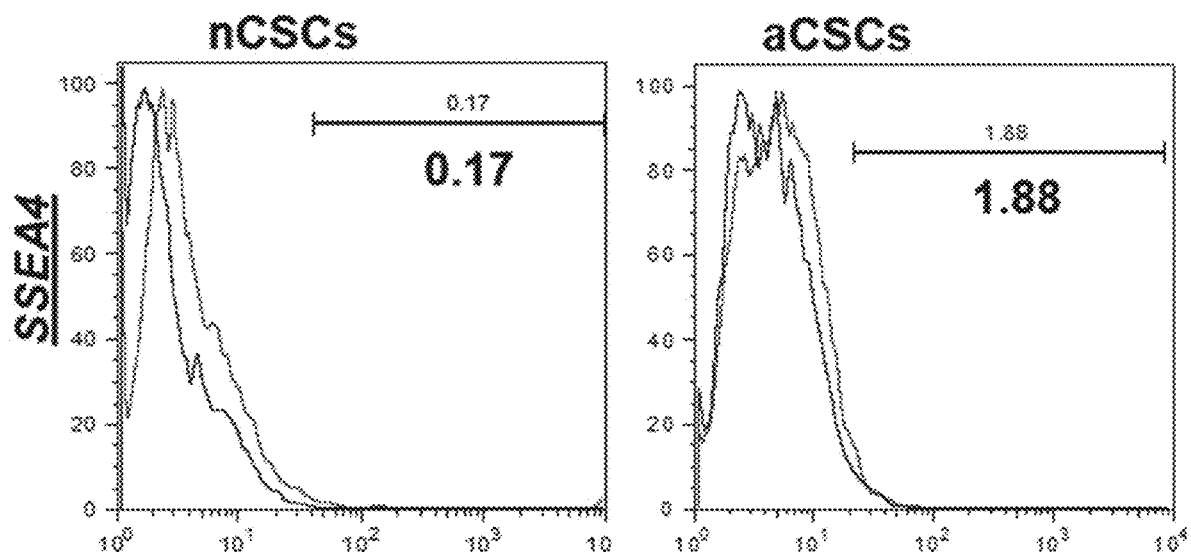
Figure 2J:
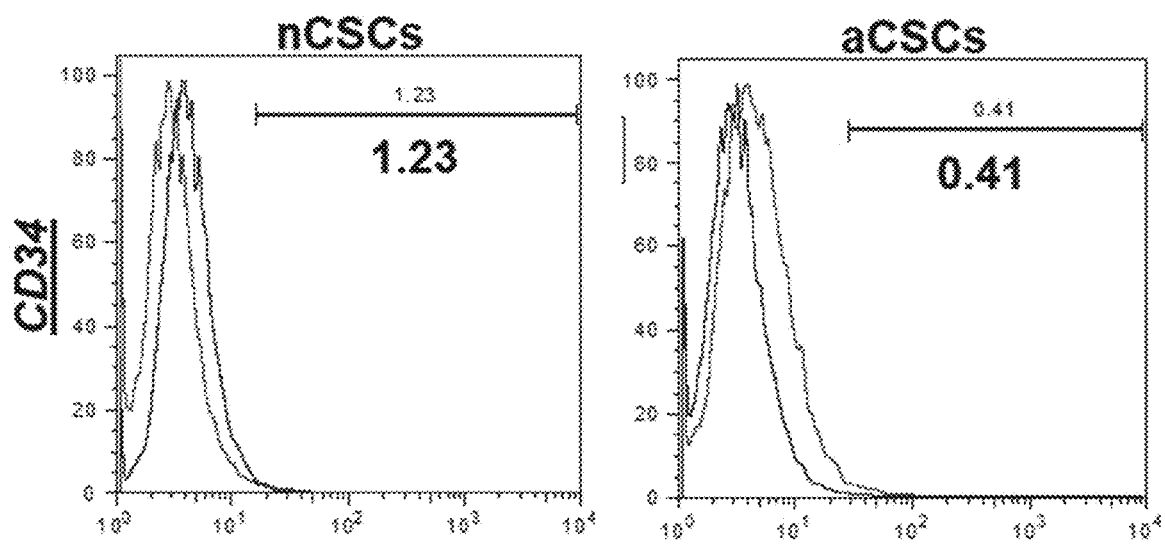
Figure 2K:
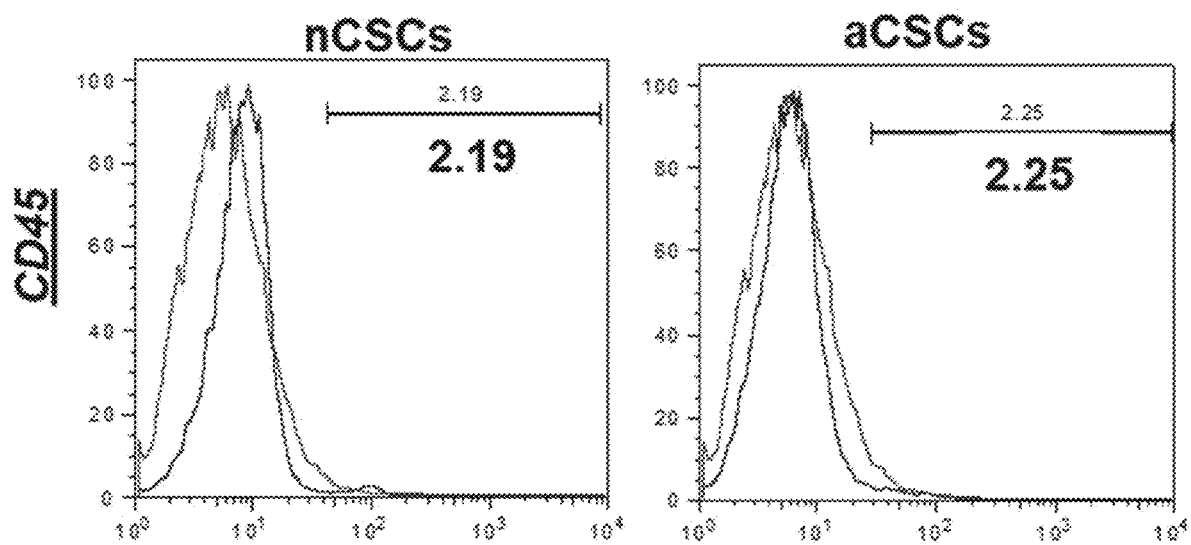
Figure 2L:
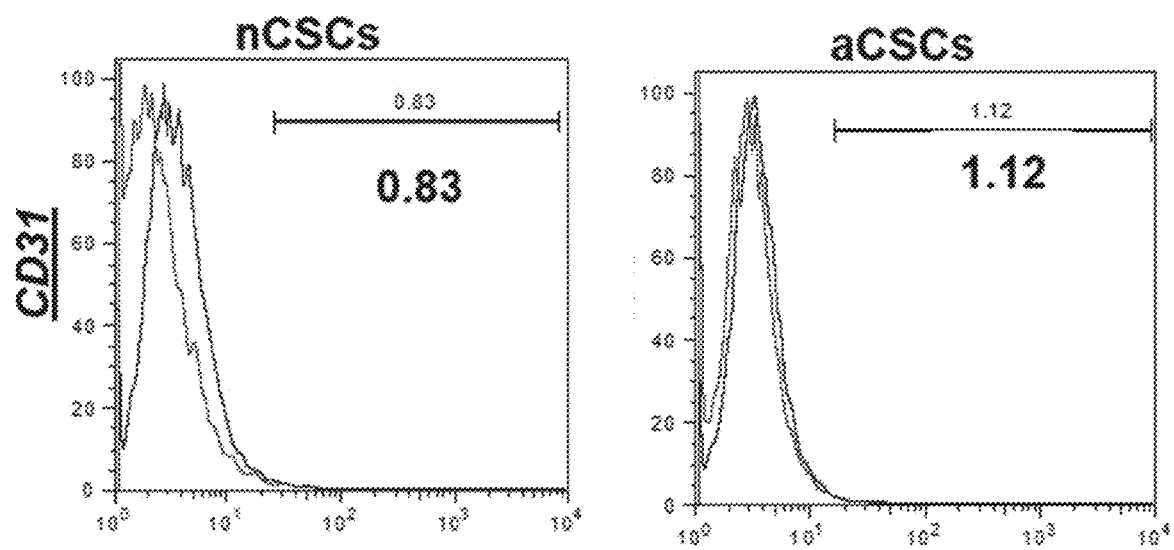
Figure 2M:
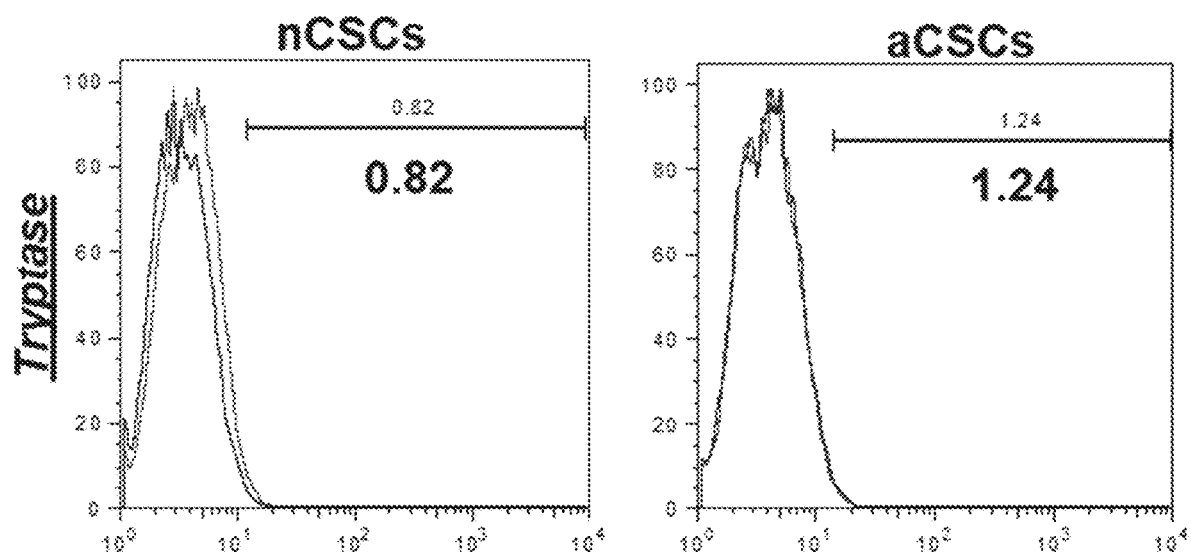

FIGS. 2A-2M. C-kit+ cardiac cells specific marker profile of nCSCs and aCSCs. Representative histograms of flow cytometry of antigenic phenotype of nCSCs and aCSCs at P3. Conjugated isotype control (red in a colorized version) used in all experiments. nCSCs and aCSCs both cell types expressed mesenchymal stem cell markers CD90, CD105 (FIGS. 2A-2B). Cardiac specific transcription factor GATA4 and ISL1 (FIGS. 2C-2D) were not expressed by nCSCs or aCSCs but both cell types expressed Nkx2.5 (FIG. 2E) and cardiac stem cell marker c-kit (FIG. 2F). nCSCs and aCSCs did not express myocytes specific marker as myosin heavy chain (MHC) (FIG. 2G), embryonic stem cell markers like SSEA3 and SSEA4 (FIGS. 2H-2I), hematopoietic marker CD34 and CD45 (J-K), endothelial marker CD31 (FIG. 2L) and mast cell marker like tryptase (FIG. 2M).

Figure 3A:
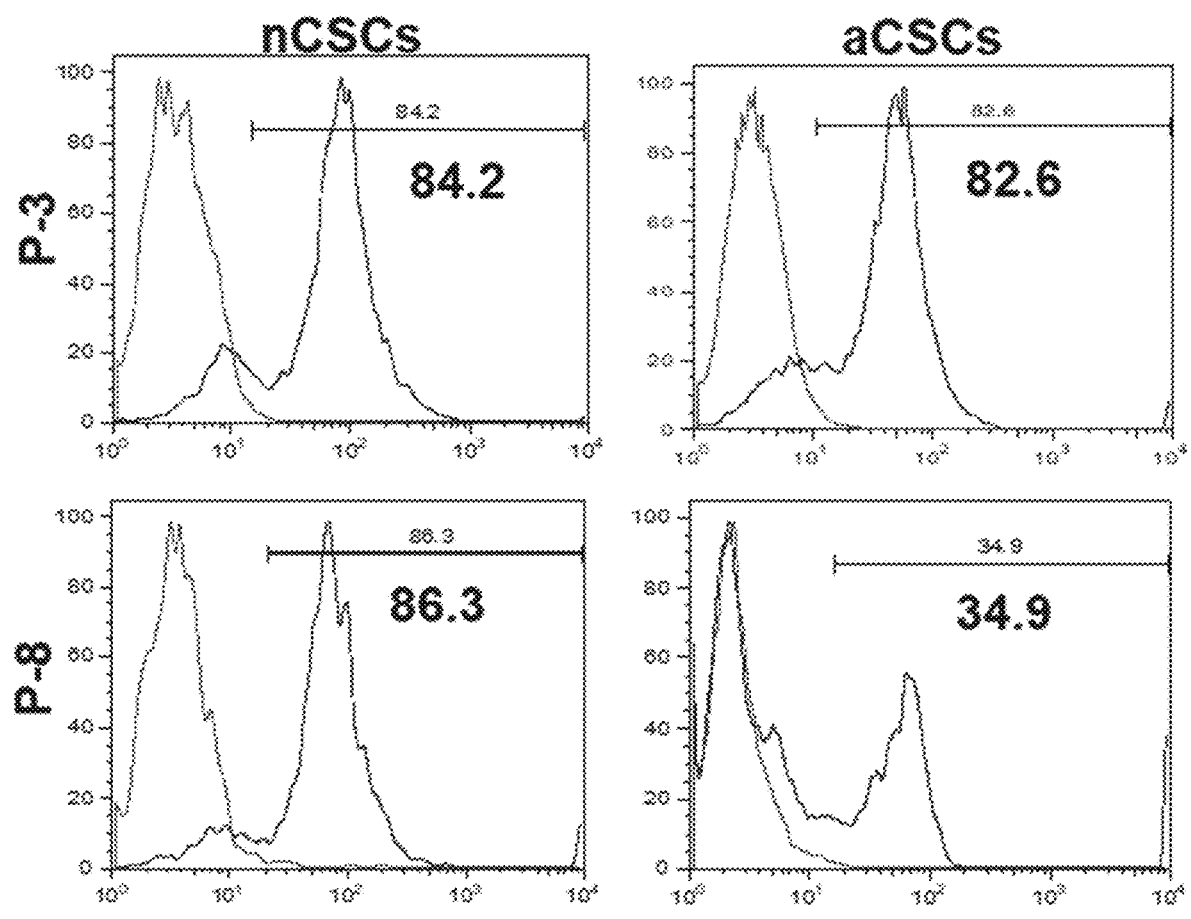
Figure 3B:
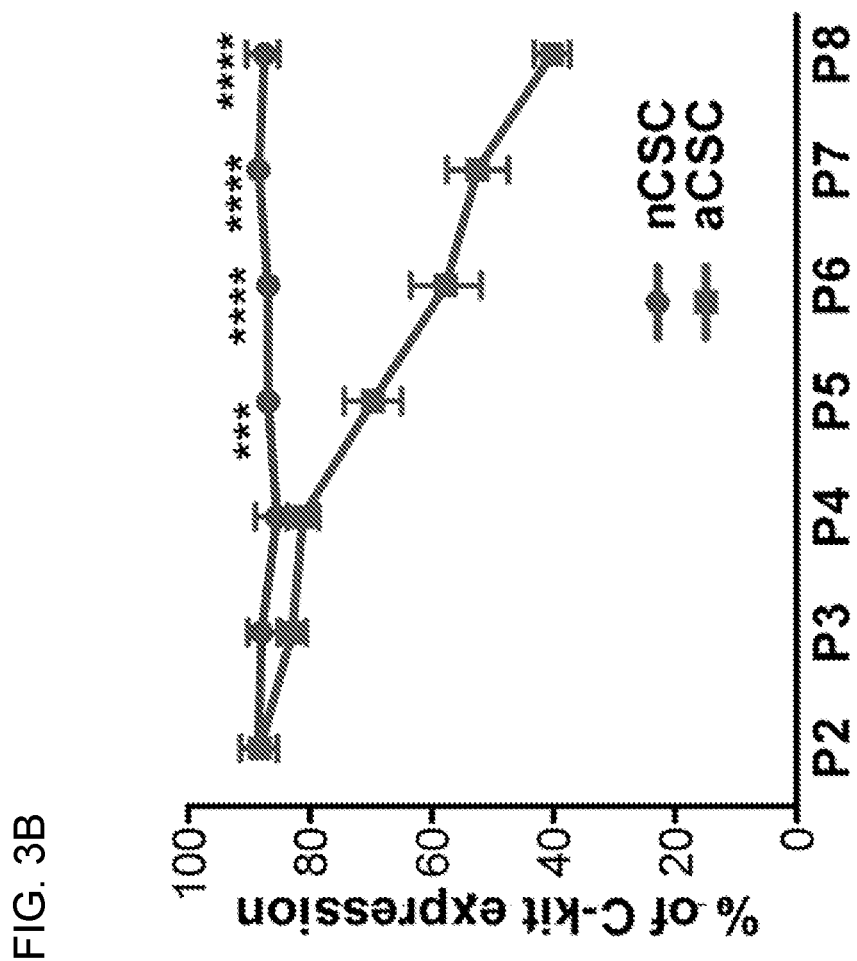
Figure 3C:
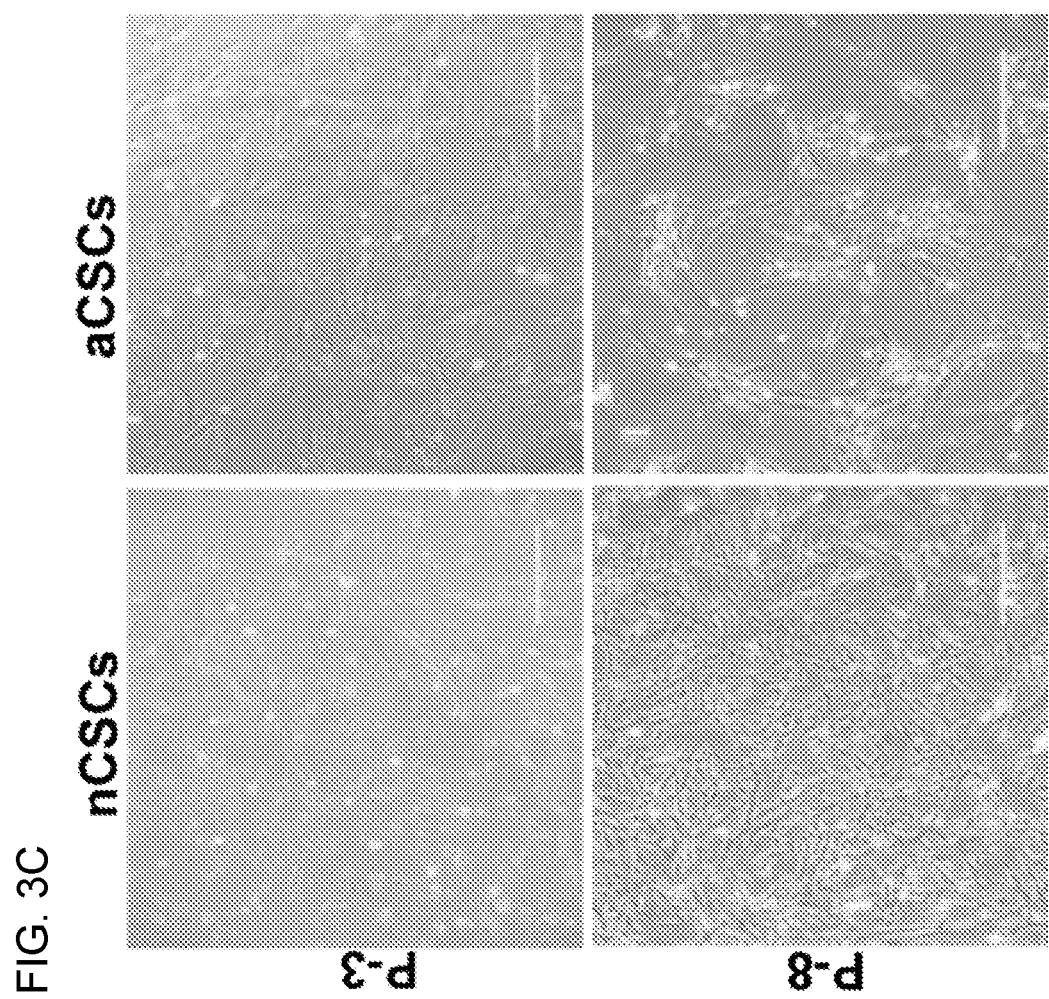
Figure 3D:
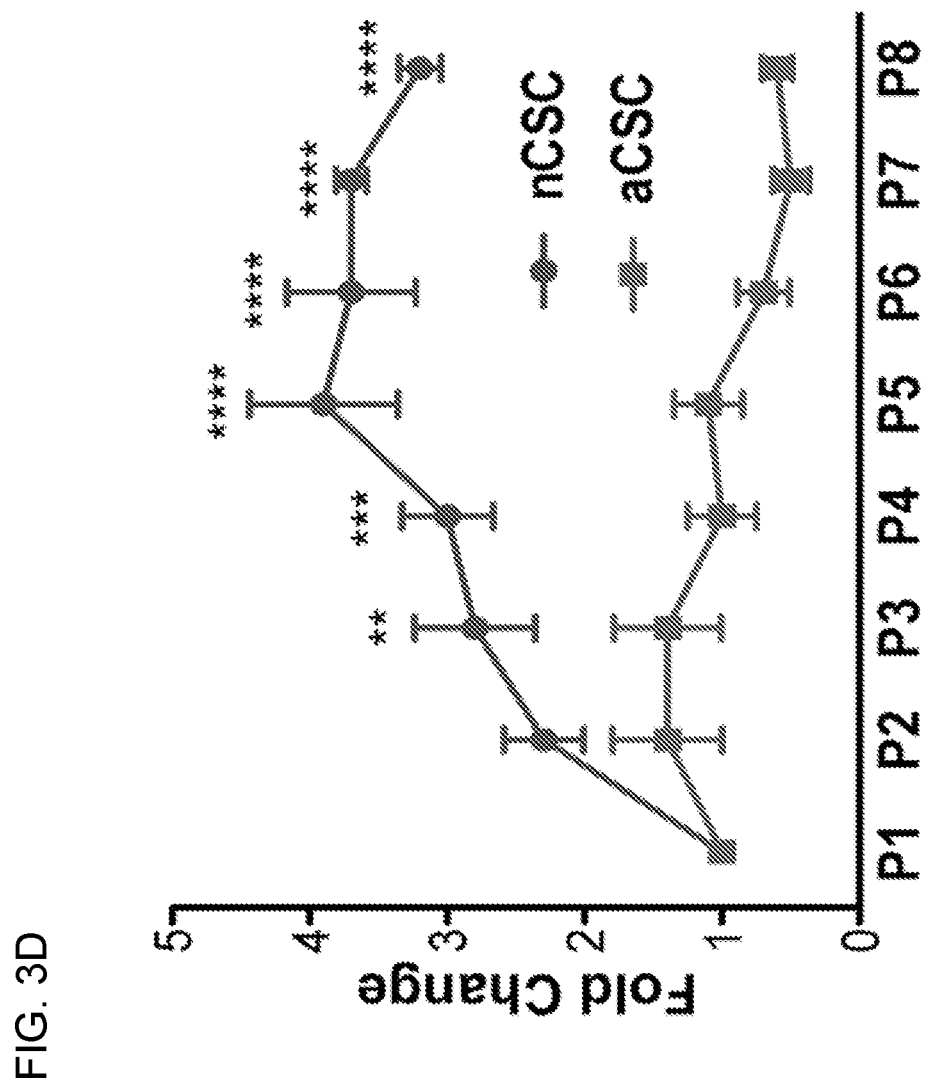
Figure 3E:
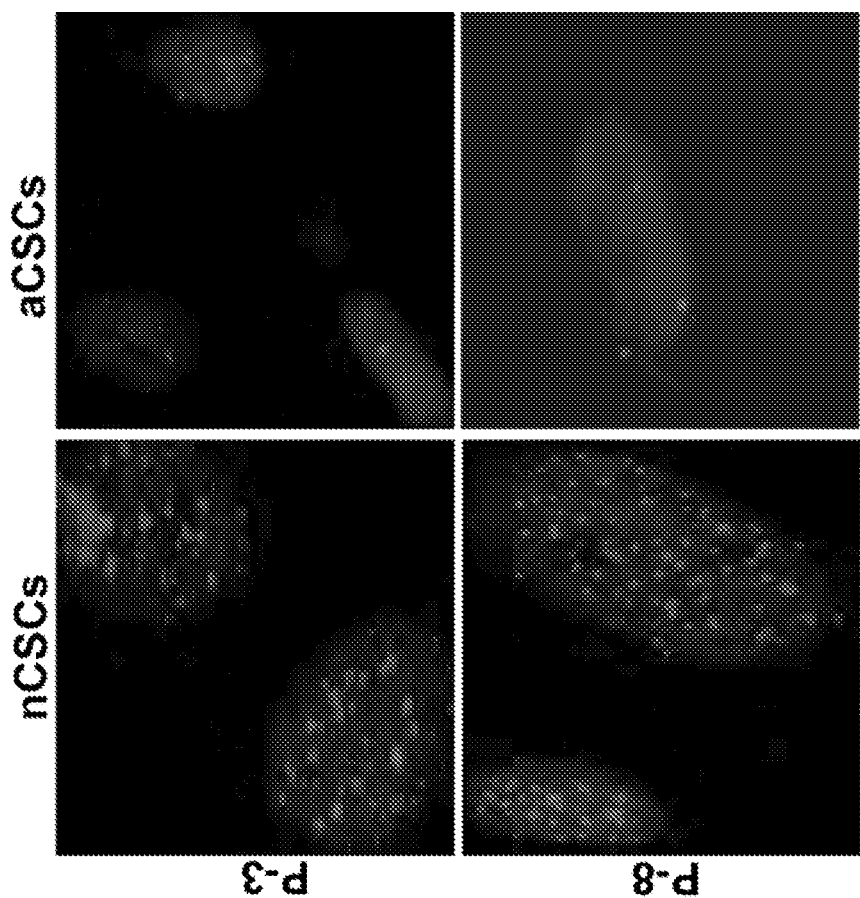
Figure 3F:
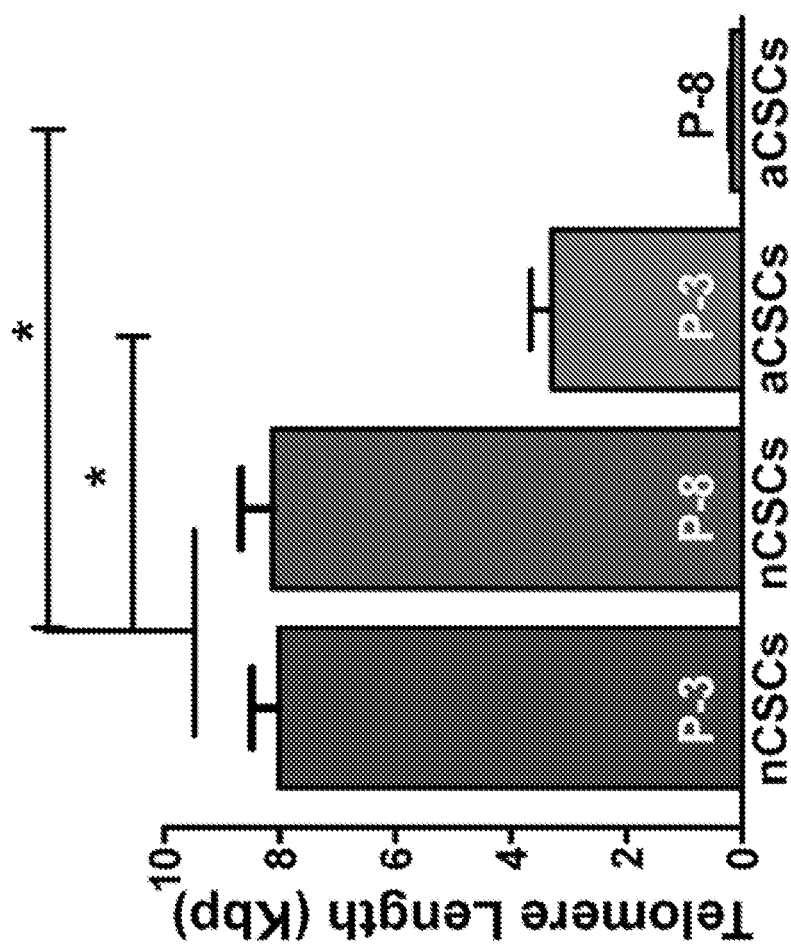
Figure 3H:
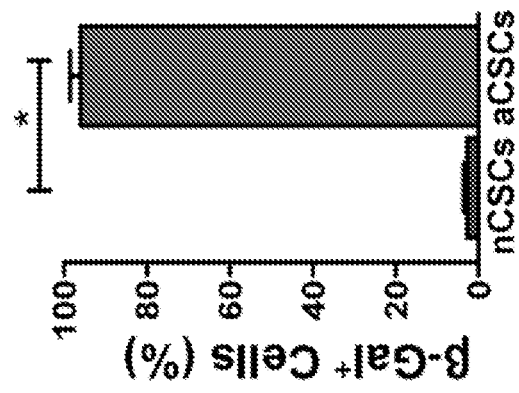
Figure 3G:
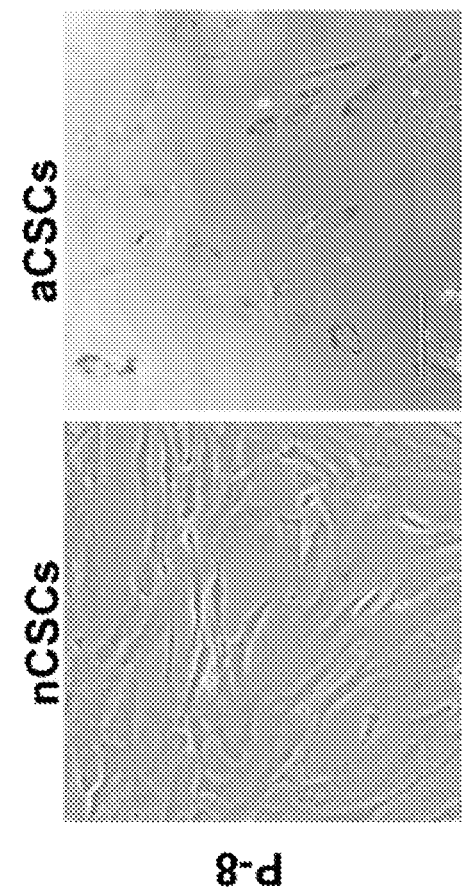

FIGS. 3A-3J. Comparative analysis of growth potential of nCSCs and aCSCs at P3 and P8. FIG. 3A). Representative histograms of flow cytometry of c-kit expression of nCSCs and aCSCs at P3 and P8. Conjugated isotype control (red) used in all experiments. C-Kit expression was significantly reduced in aCSCs at P8 as compared to nCSCs at P8. FIG. 3B). Quantification of c-kit expression at each passage in nCSCs and aCSCs. Data showed that the c-kit expression significantly reduced in aCSCs by P5 and kept declining till P8. FIG. 3C). nCSCs maintained a high growth potential which remained unaffected by increasing number of passages (P3-P8), while aCSCs gradually lost their potential to give rise to daughter cells (P8). FIG. 3D). Quantification of growth potential of nCSCs and aCSCs. FIGS. 3E-3F). Immunostaining for the telomere length showed a significant reduction in telomere length in aCSCs at P3 and P8 as compared to nCSCs. as analyzed by. FIG. 3G). nCSCs attain senescence by P8 as analyzed by beta-galactosidase staining. FIG. 3H). Quantification of beta-galactosidase positive cells a significant difference between nCSCs and aCSCs at P8. FIG. 3I). nCSCs are more resistant to apoptosis induced by 50 mM hydrogen peroxide as assessed by TUNEL staining. FIG. 3J). Quantification of apoptosis showed a significant increase in cell death in aCSCs at P8 as compared to nCSCs. The data was analyzed using GRAPHPAD® software and represented as mean±SEM. (*P<0.05, P<0.01, *P<0.001 and **P<0.0005)**P<0.0005). Grouped data was analyzed by 2-way ANOVA followed by Bonferroni post hoc analysis.

Figure 4A:
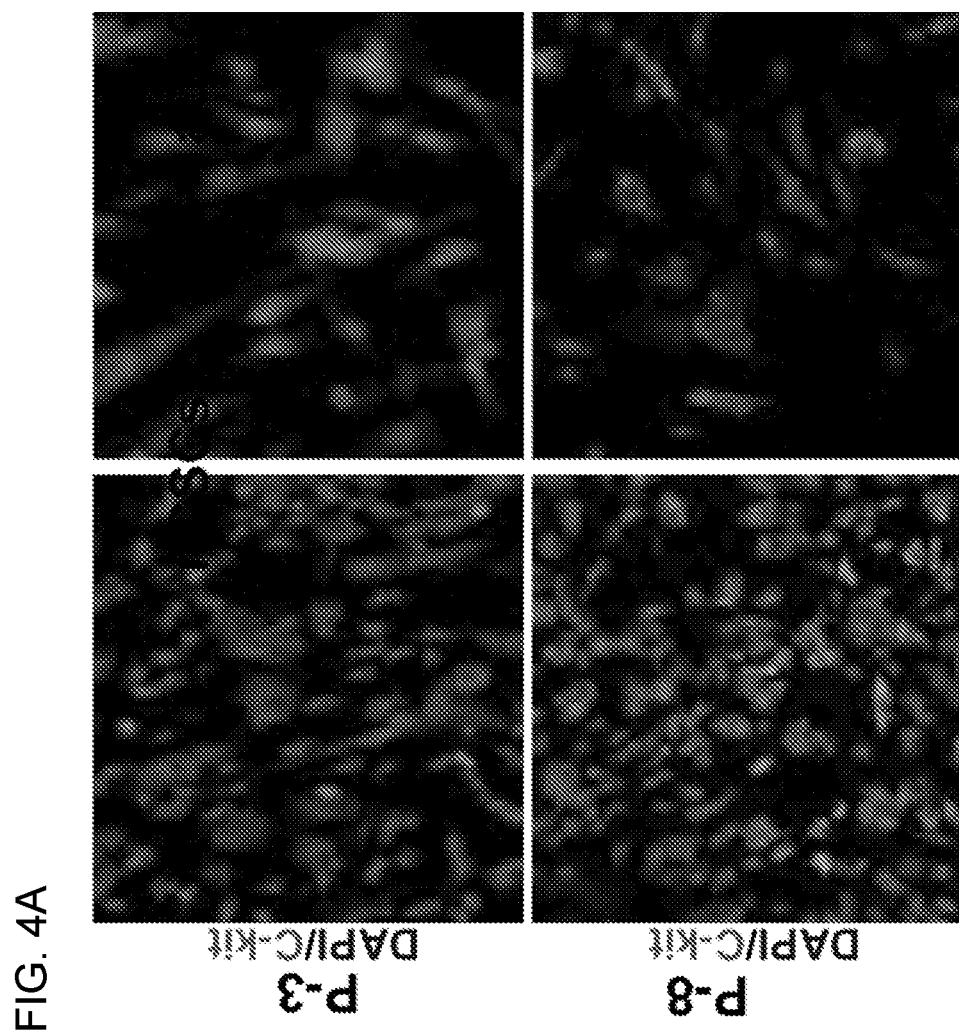
Figure 4C:
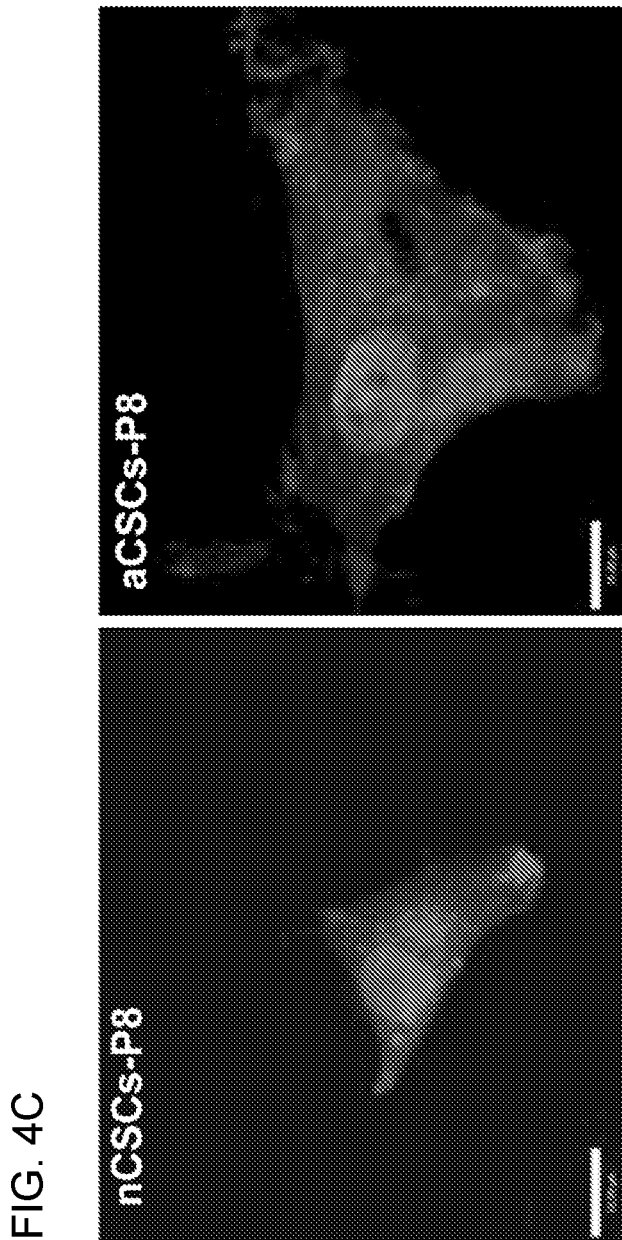

FIGS. 4A-4C. Comparative analysis of nCSCs and aCSCs at P3 and P8. FIG. 4A). Immunostaining analysis showed a declined c-kit expression in aCSCs at P8. FIG. 4B). aCSCs express p16INK4a at P8 as shown by immunocytometry. FIG. 4C). aCSCs enlarged in size at P8 as shown by immunostaining analysis using WGA membrane marker.

Figure 5E:
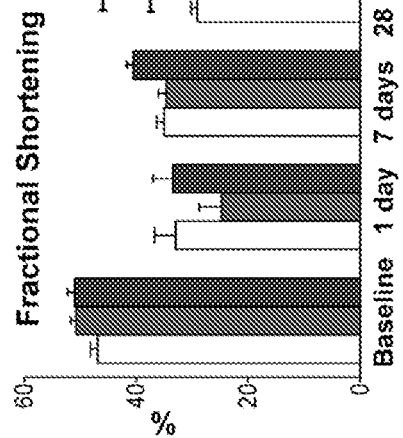
Figure 5F:
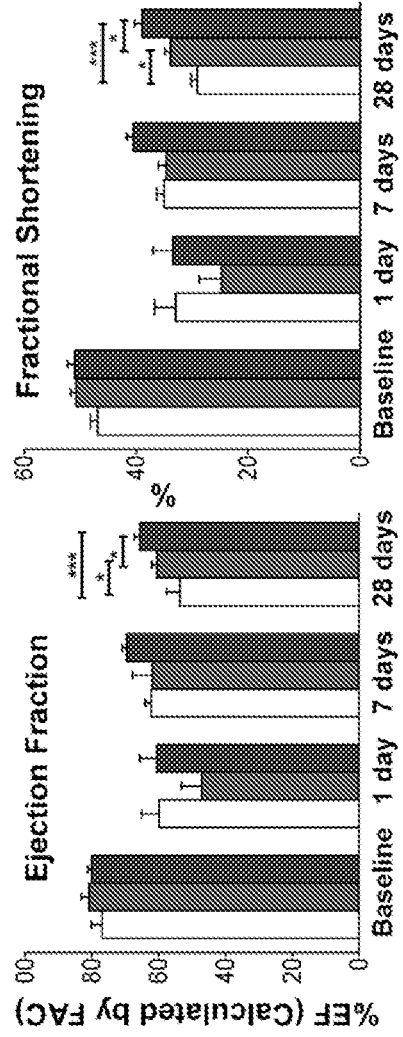
Figure 5G:
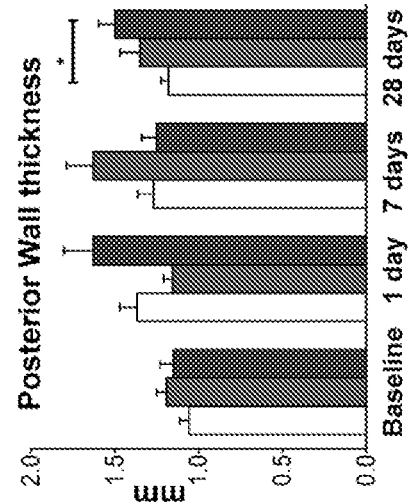
Figure 5H:
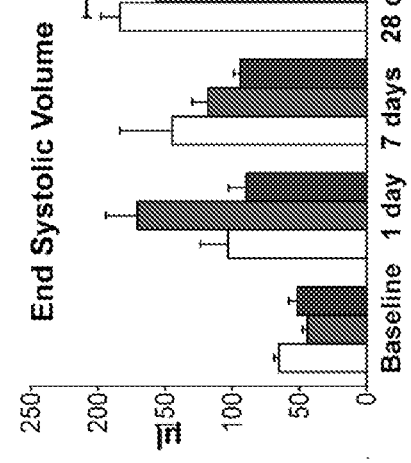
Figure 5I:
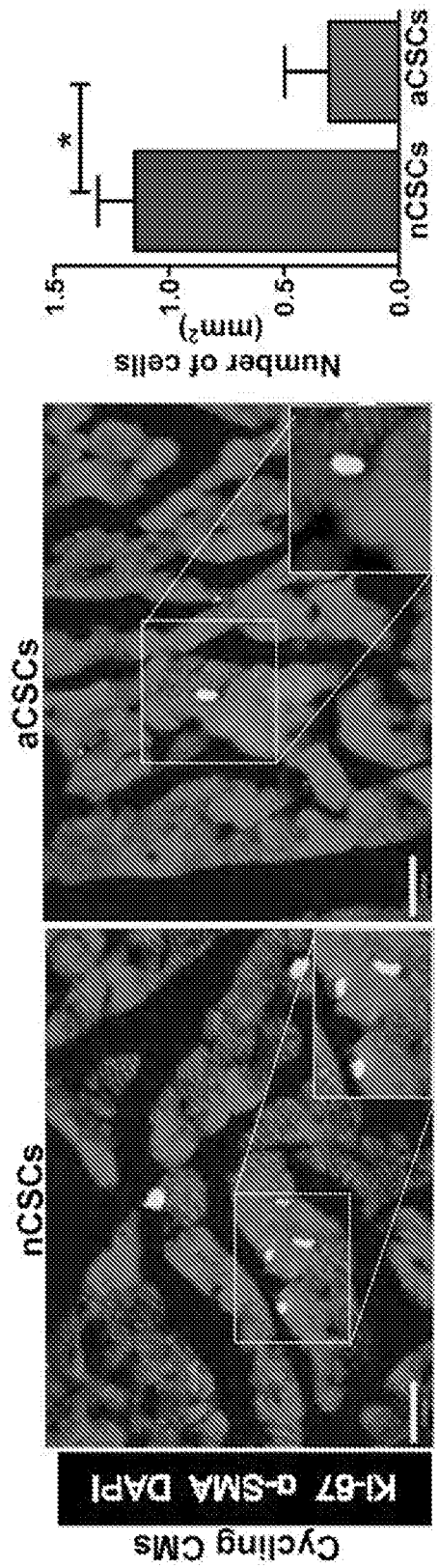
Figure 5J:
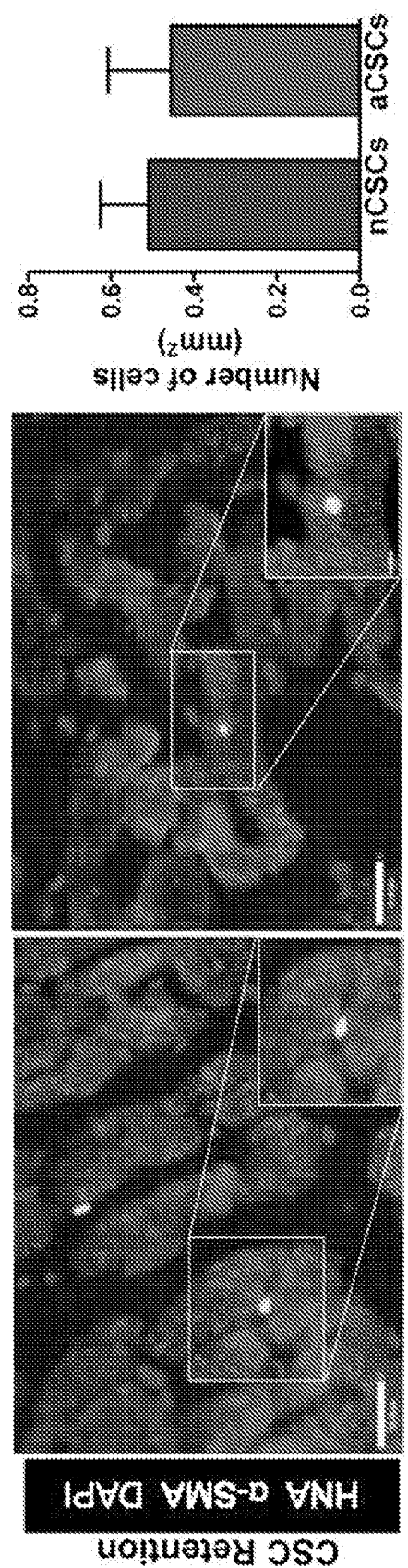
Figure 5K:
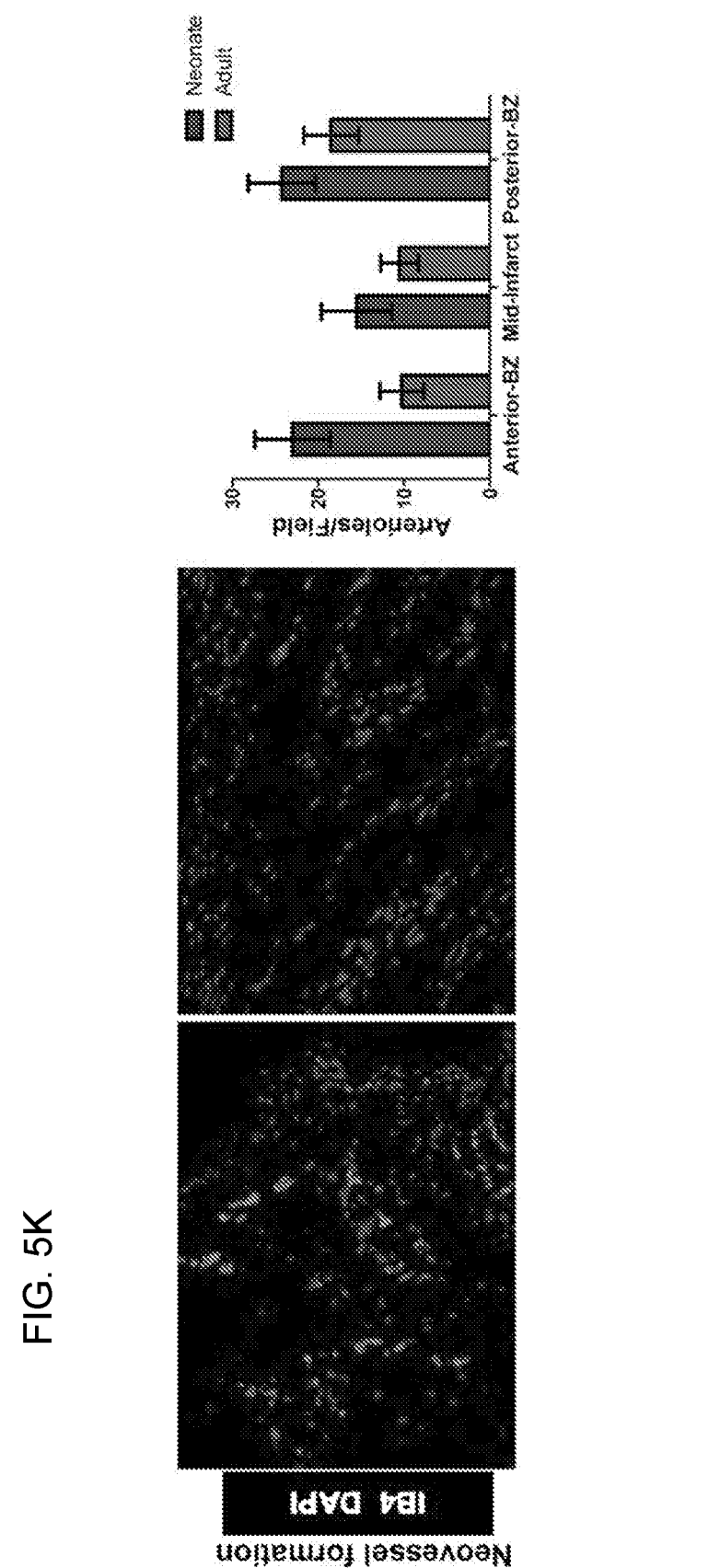
Figure 5L:
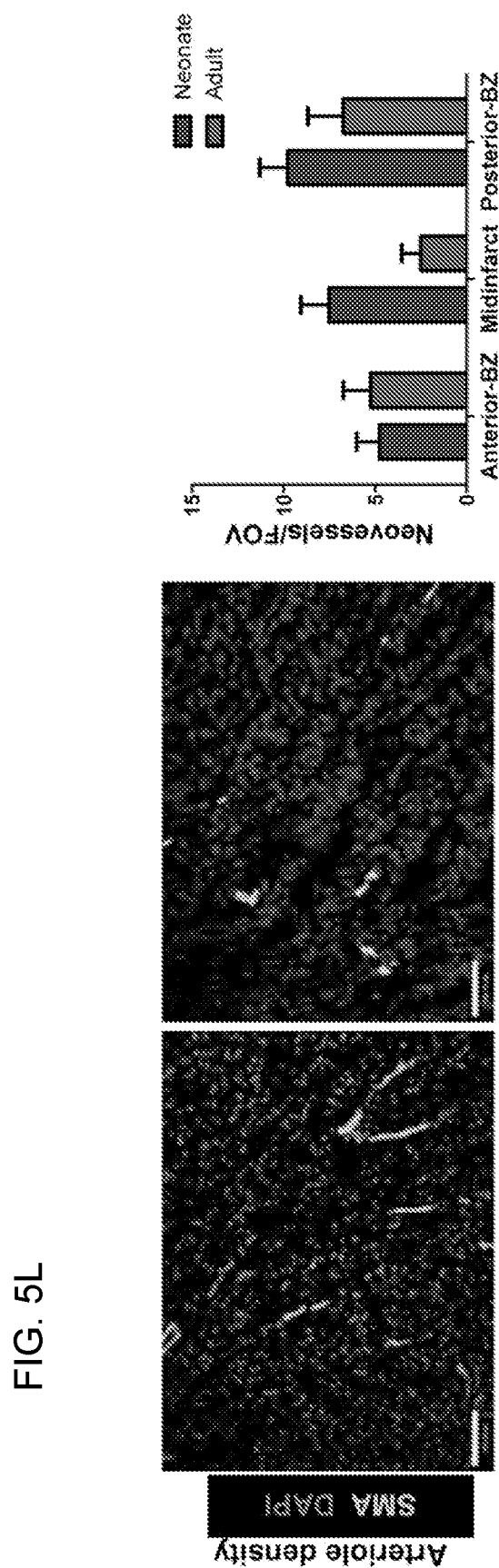

FIGS. 5A-5L. Cardiac function measured by echocardiography. FIGS. 5A-5D). Representative M-mode tracings from animals at baseline 4 weeks post-MI treated with IMDM, nCSCs, or aCSCs. All the animals that underwent surgeries, received follow-up echocardiography at 2 and 4 weeks post-MI. FIGS. 5E-5F). Structural and functional parameters derived from echocardiography measurements are shown. A significant increase in ejection fraction, fractional shortening and significant decrease in the end systolic volume was observed after nCSCs transplantation as compared to aCSCs and placebo (IMDM) (FIGS. 5G-5H). FIG. 5I. Transplantation of nCSCs significantly increased the number of cycling cardiomyocytes. FIG. 5J. 4 weeks post-MI very few cells were tracked in the rodent myocardium after nCSCs or aCSCs transplantation. Immunofluorescence demonstrated increased formation of neovessels marked by IB4 expression (FIG. 5K) and of arterioles marked by a-SMA expression (FIG. 5L) in myocardium sections of the mid-infarct regions transplanted with nCSCs than transplanted with aCSCs.

Figure 6A:
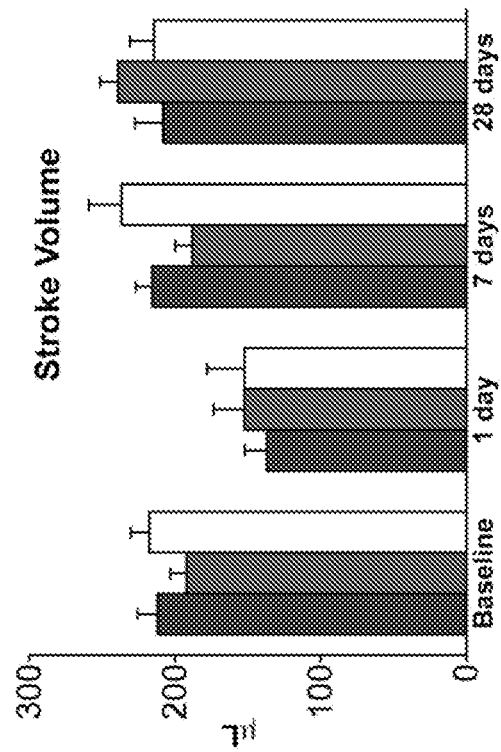
FIGS. 6A, 6B, 6C, 6D, and 6E show cardiac function and structure improvement by nCSCs or aCSCs transplantation.
Figure 6B:
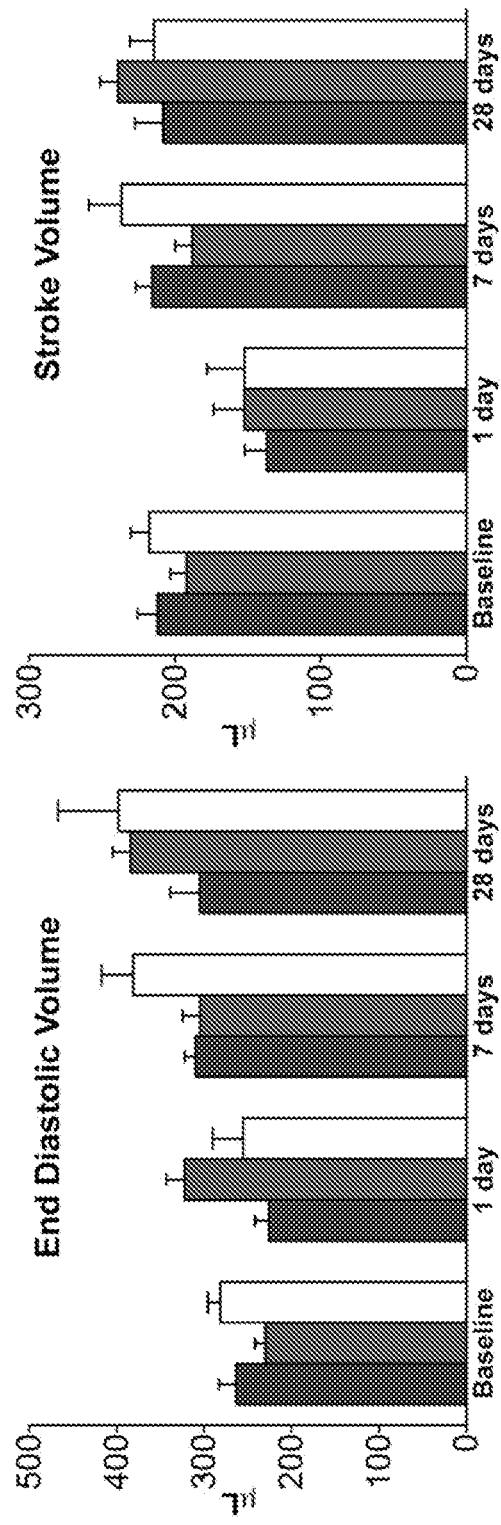
Figure 6C:
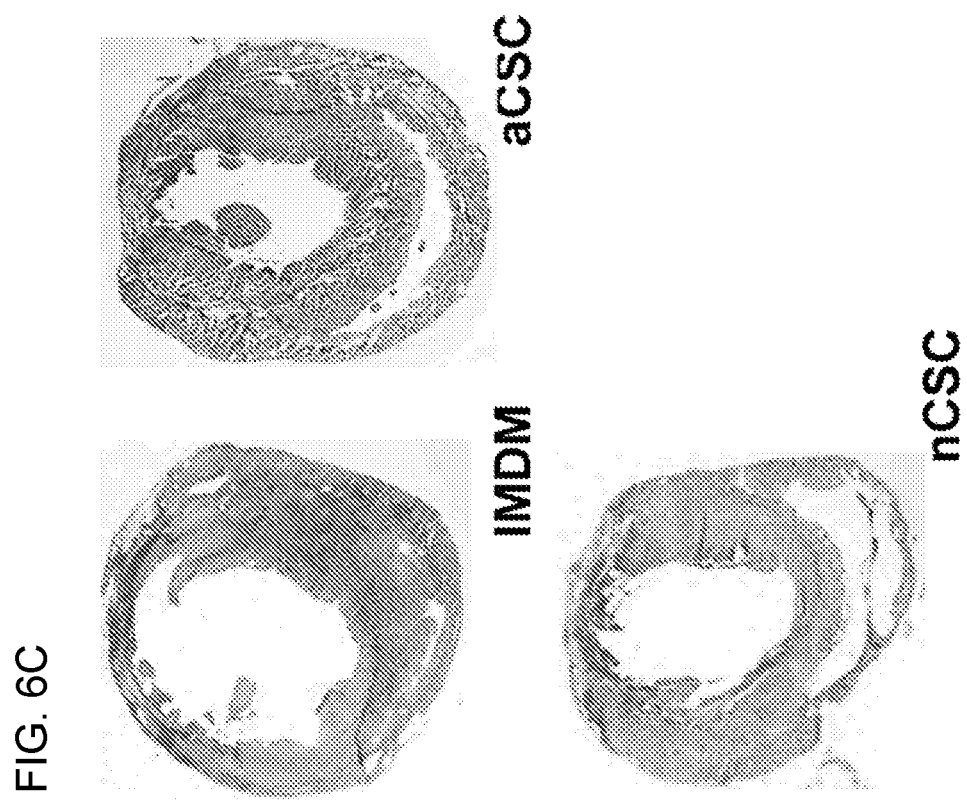
Figure 6E:
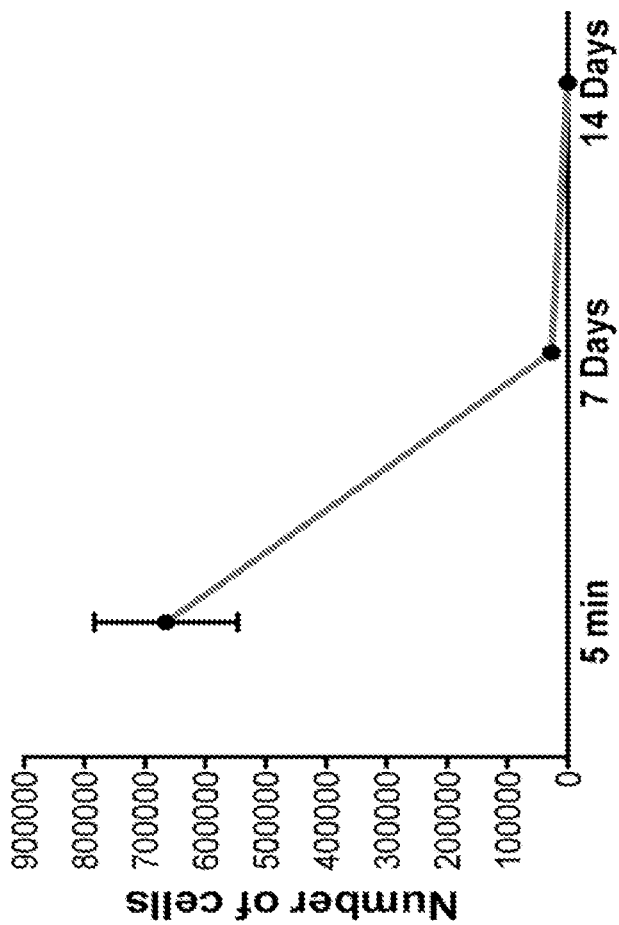
Figure 6D:
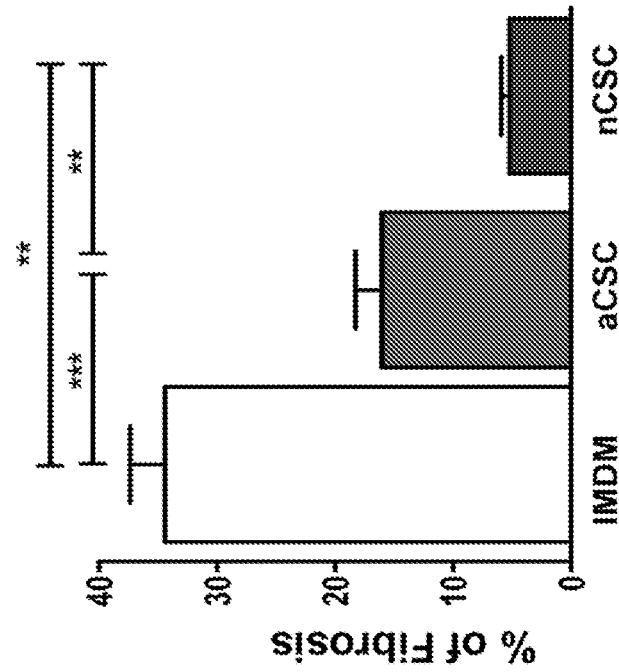

FIGS. 6A-6E. Cardiac function and structure improvement by nCSCs or aCSCs transplantation. FIGS. 6A-6B.) End diastolic and stroke volume were not affected by transplantation of aCSCs or nCSCs. FIGS. 6C-6D). Infarct size determined by Masson's trichrome staining was reduced with transplanted nCSCs when compared with IMDM or aCSCs. FIG. 6E). Quantification of the cells retained in rodent myocardium as determined by RT-PCR analysis.

Figure 7A:
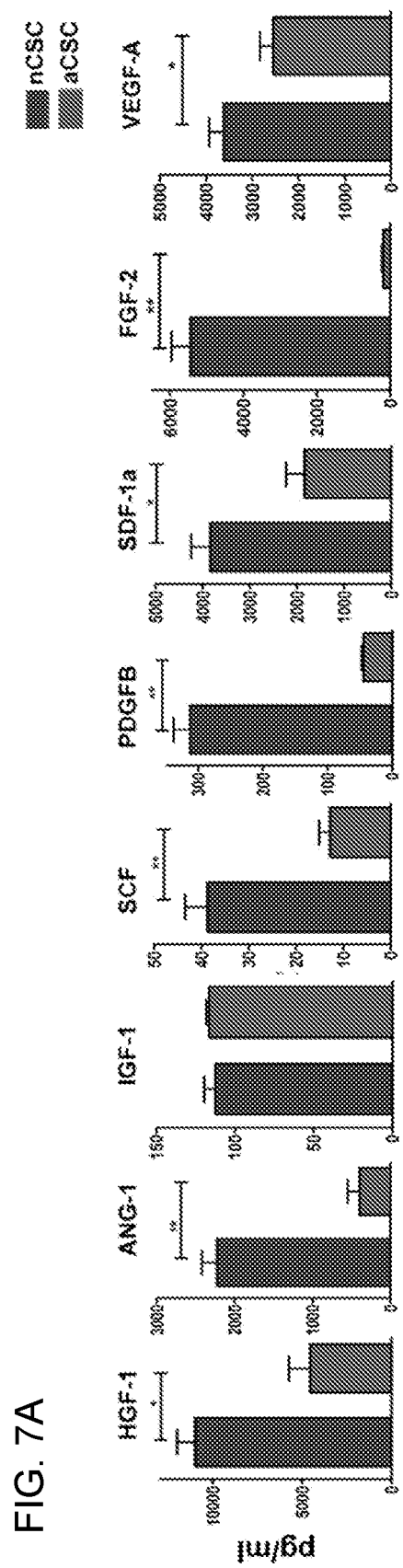
FIGS. 7A and 7B display expression of angiogenic paracrine factors in vitro and in vivo by nCSCs and aCSCs.
Figure 7B:
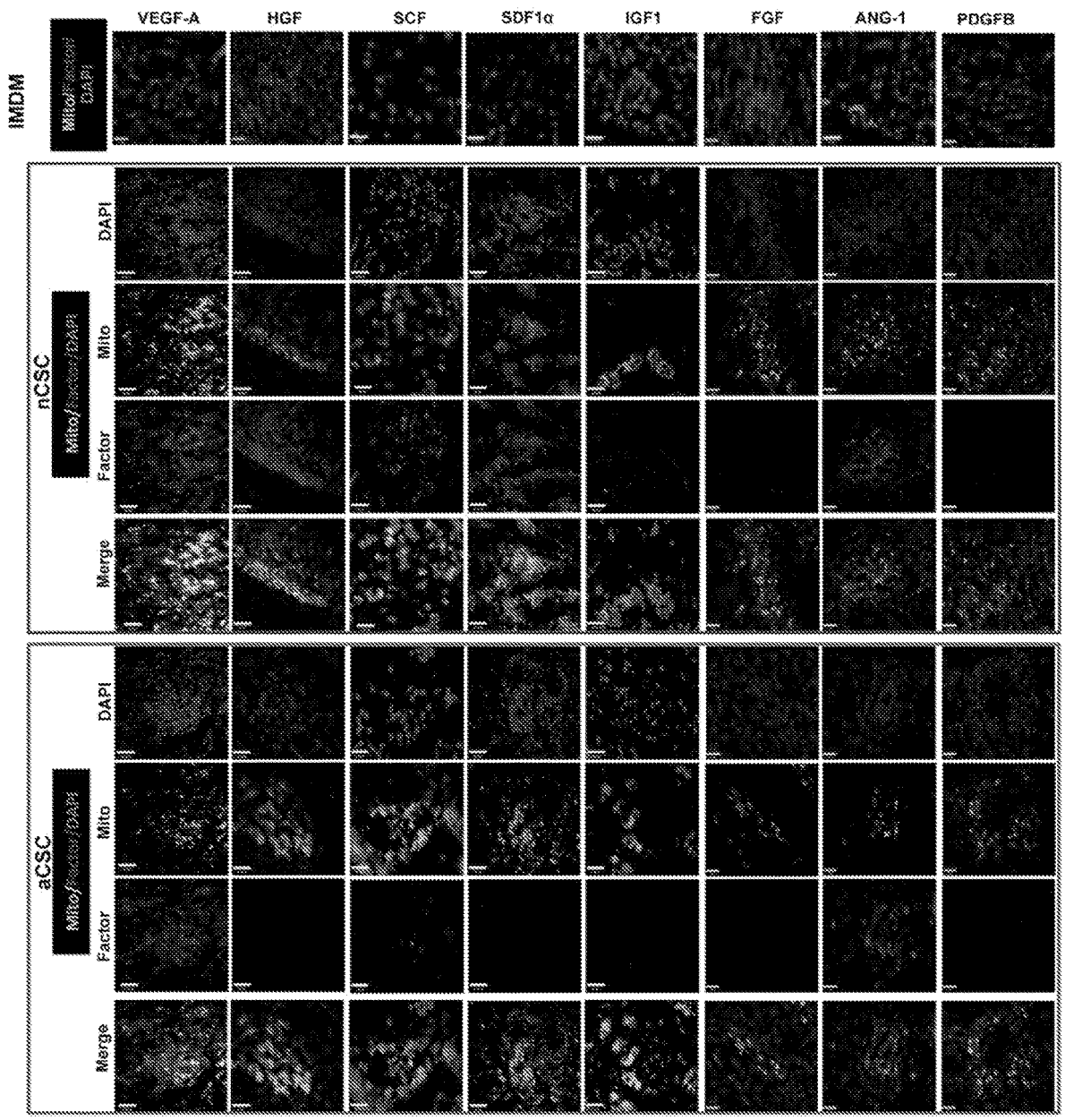

FIGS. 7A-7B. Expression of angiogenic paracrine factors in vitro and in vivo by nCSCs and aCSCs. FIG. 7A). ELISA of the paracrine factors like HGF-1, ANG-1, PDGFB, SDF-1α, FGF-2 and VEGFA was significantly higher in nCSCs as compared to aCSCs. No difference was observed in the secretion of IGF-1 by nCSCs or aCSCs. FIG. 7B). Characterization of paracrine factors secreted by nCSCs and aCSCs after 24 hours post-MI in vivo. After 10 minutes of MI, rats received nCSCs or aCSCs. The animals were euthanized 24 hours post-MI for analysis of paracrine factor production. Human cells (nCSCs or aCSCs) were tracked using human mitochondria antigen in rat myocardium. nCSCs stained positive for VEGF, HGF-1, SCF, SDF-1α and ANG-1 but negative for IGF-1, PDGFB and FGF. aCSCs stained positive for VEGFA and ANG-1 but stained negative for PDGFB, SCF, HGF, IGF-1, and SDF-1α. Nuclei are labeled with DAPI (blue in a colorized version). VEGF, vascular endothelial growth factor, Ang-1 indicates angiopoietin-1; bFGF, basic fibroblast growth factor; HGF, hepatocyte growth factor; IGF1, insulin like growth factor; PDGF, platelet-derived growth factor; SCF, stem cell factor; SDF-1α, stromal-derived factor-1. Data are represented as mean±SEM and analyzed by t-test (Mann-Whitney test) followed by Dunn's post hoc test. (*P<0.05, P<0.01, *P<0.001)

Figure 8:
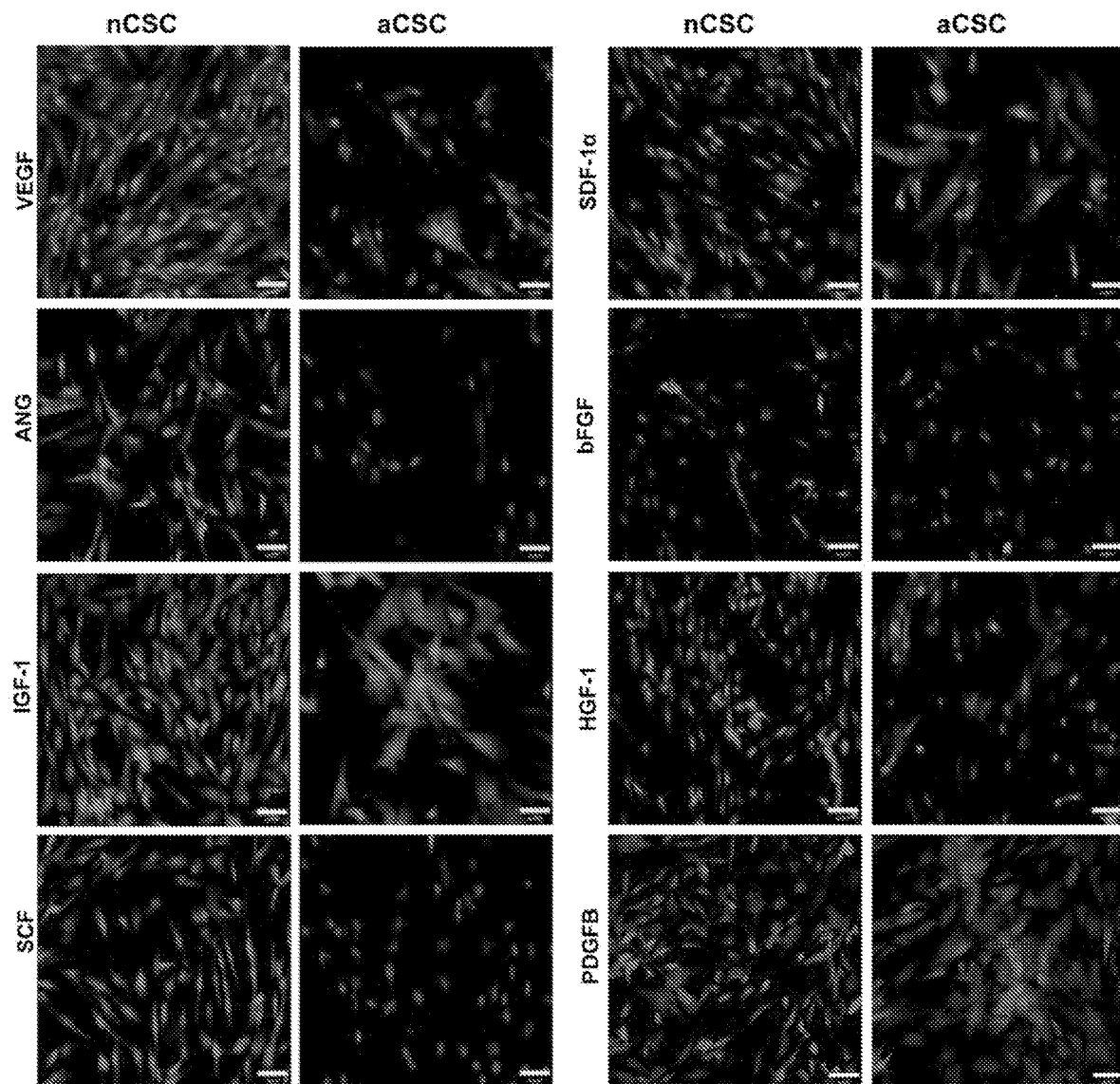
FIG. 8 provides expression of various angiogenic paracrine factors in vitro by nCSCs and aCSCs.

FIG. 8. Expression of various angiogenic paracrine factors in vitro by nCSCs and aCSCs. Higher expression of VEGFA, ANG-1, SCF, SDF-1α, HGF-1 and PDGFB was observed in nCSCs as compared to aCSCs.

Figure 9A:
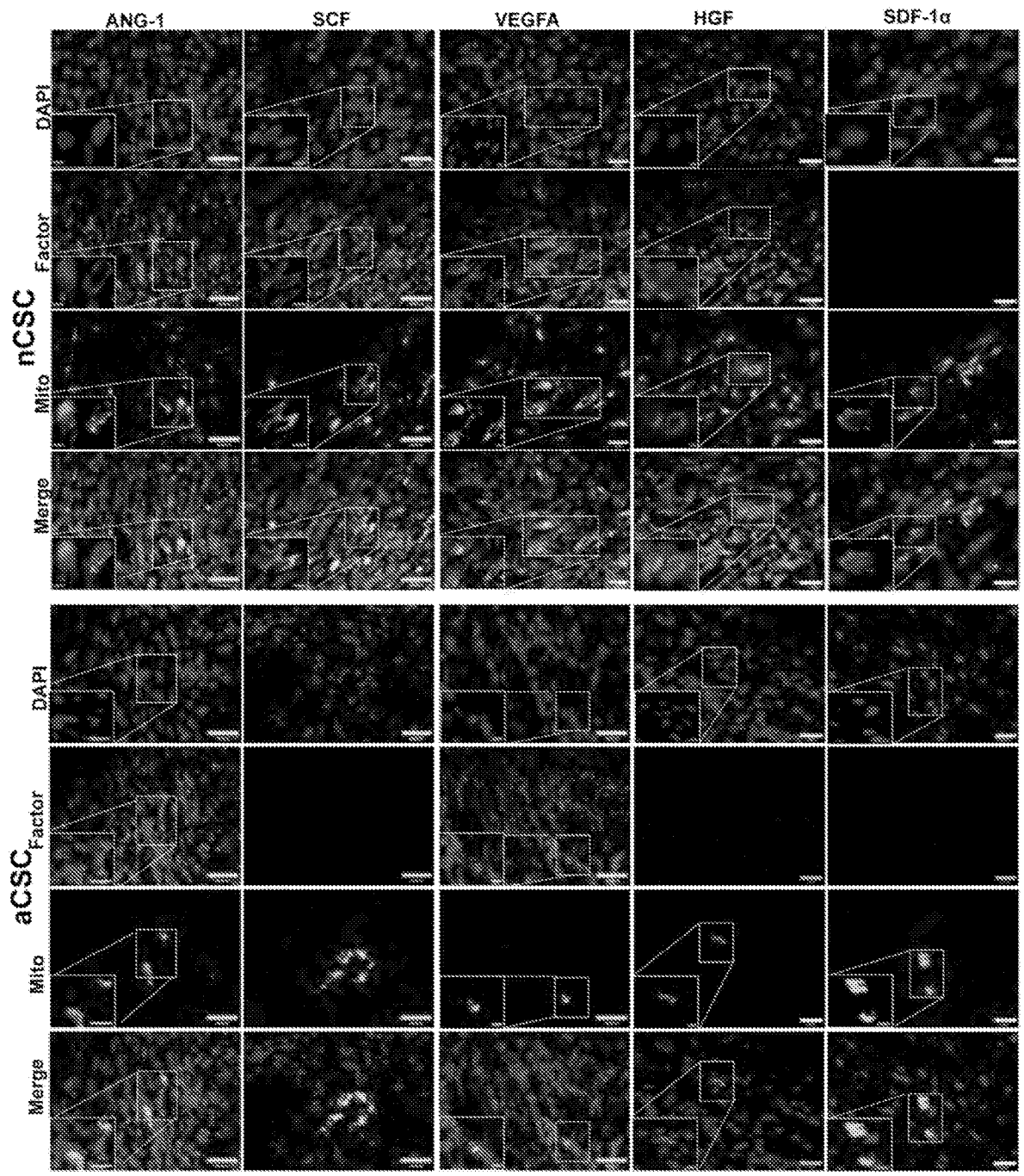
FIGS. 9A, 9B, 9C, 9D, and 9E depict expression of pro-angiogenic paracrine factors and effect on proliferation and inflammation after 72 hours of transplantation of nCSCs and aCSCs in vivo.
Figure 9B:
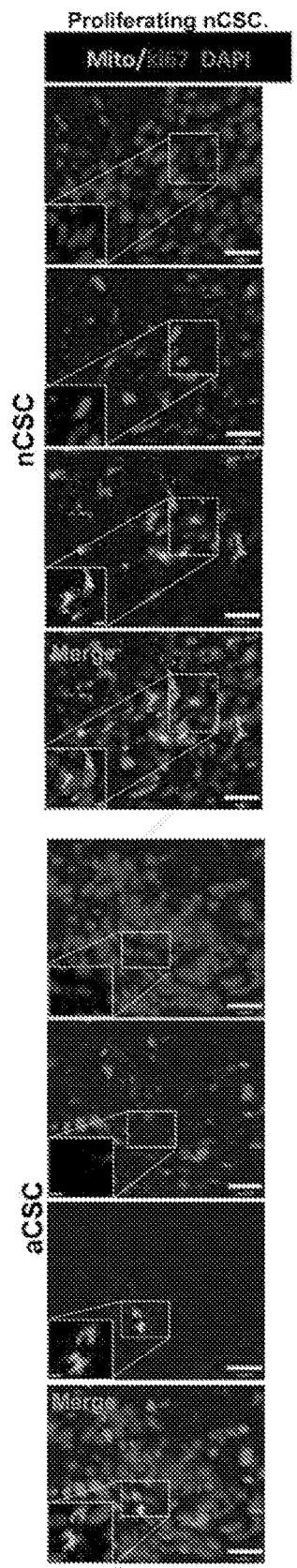
Figure 9C:
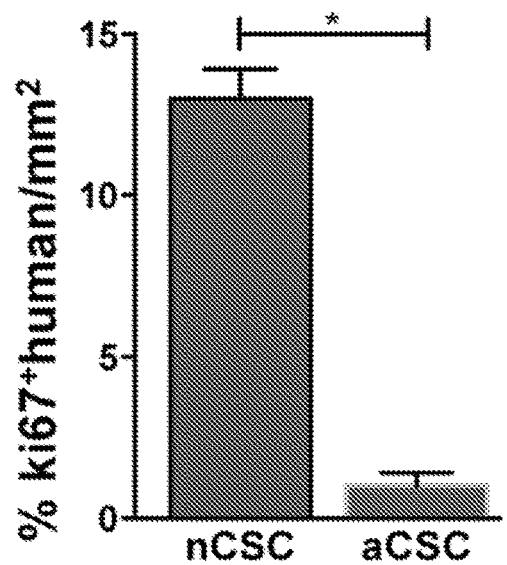
Figure 9D:
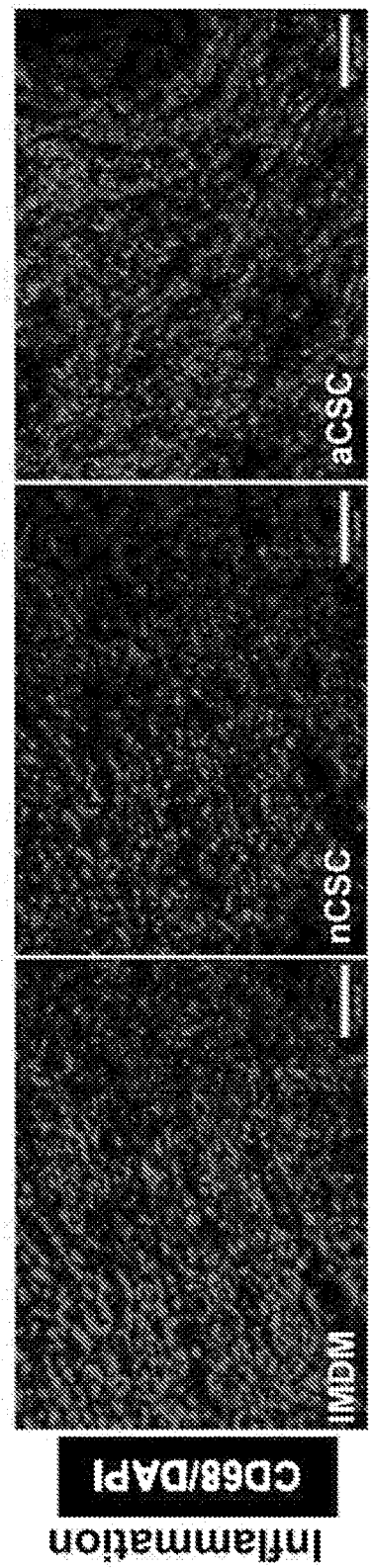
Figure 9E:
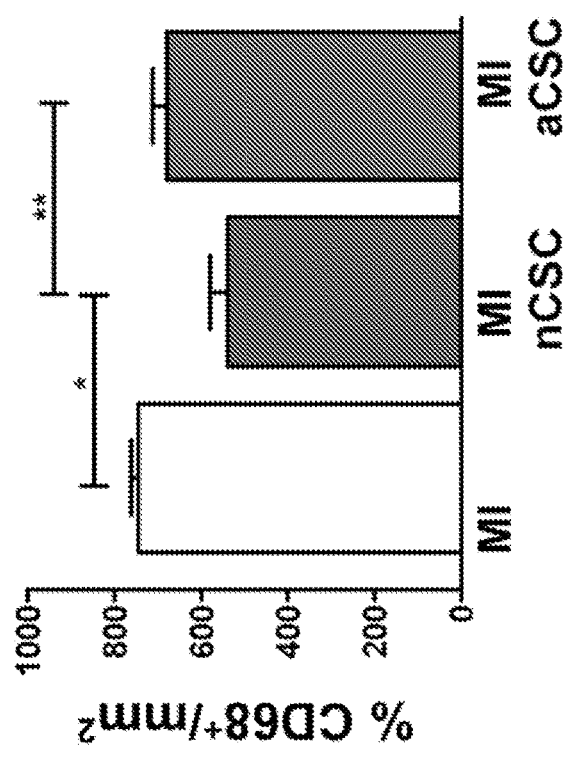

FIGS. 9A-9E. Expression of pro-angiogenic paracrine factors and effect on proliferation and inflammation after 72 hours of transplantation of nCSCs and aCSCs in vivo. FIG. 9A). After 10 minutes of MI, rats received nCSCs or aCSCs. The animals were euthanized 72 hours post-MI for analysis of paracrine factor production. Human cells (nCSCs or aCSCs) were tracked using human mitochondria antigen in rat myocardium. After 72 hours nCSCs stained positive for VEGF, HGF-1, SCF, and ANG-1 but negative for SDF-1α aCSCs stained positive for VEGFA and ANG-1. FIGS. 9B-9C). nCSCs showed a higher rate of proliferation in ischemic rat myocardium after 72 hours as compared to aCSCs. FIGS. 9D-9E). Inflammation in the myocardium at 72 hours post-MI as identified by immune-histological staining of CD68-positive cells after transplantation of nCSCs or aCSCs. Transplantation of nCSCs reduce the inflammation significantly more than IMDM or aCSCs. Data are represented as mean±SEM and analyzed by t-test (Mann-Whitney test) followed by Dunn's post hoc test. *P<0.05

Figure 10A:
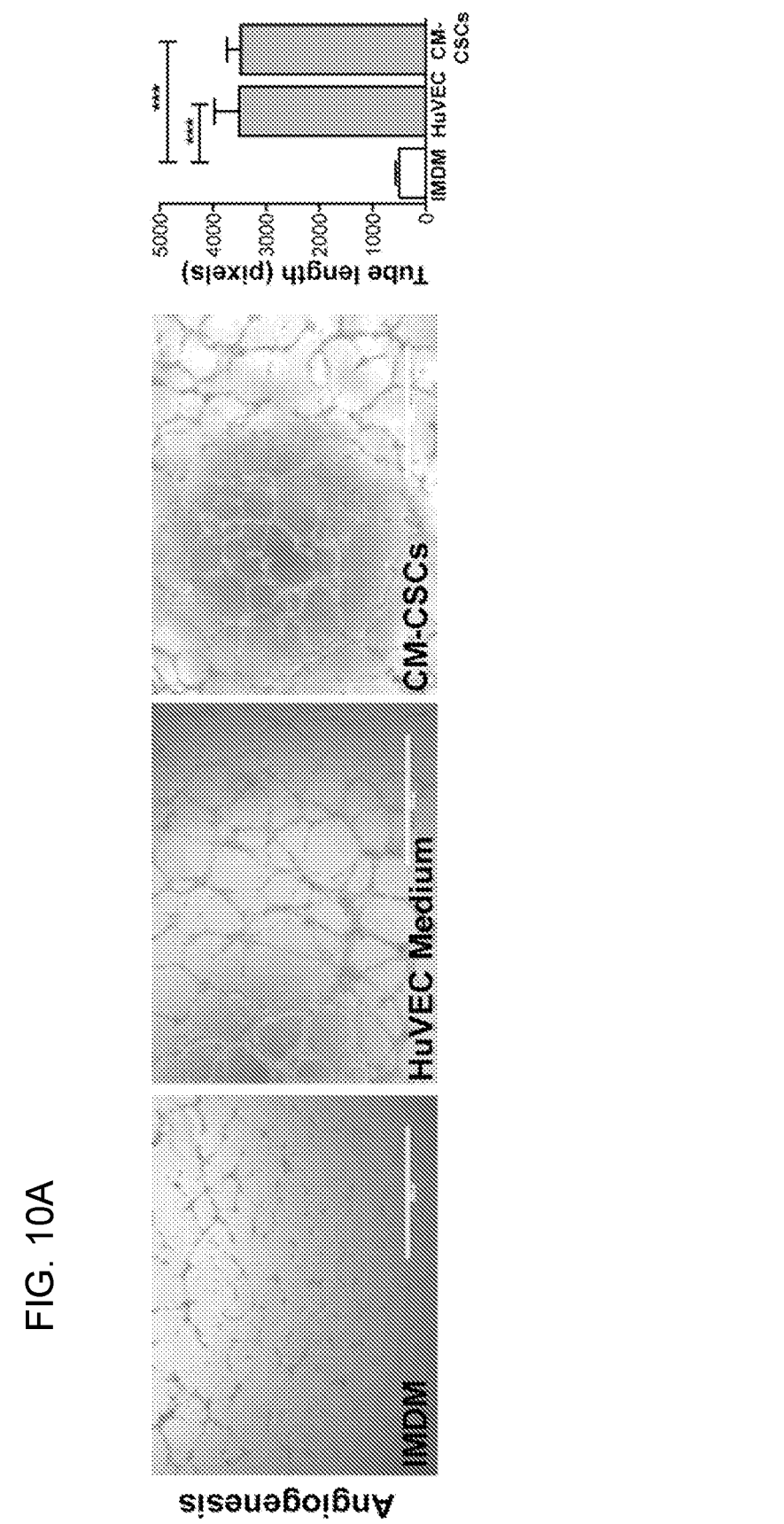
FIGS. 10A, 10B, 10C, 10D, and 10E display conditioning medium (CM) of CSCs contain pro-angiogenic, pro-proliferative and anti-apoptotic factors, which can improve cardiac function and attenuate ventricular remodeling similar to CSCs transplantation in MI model.
Figure 10B:
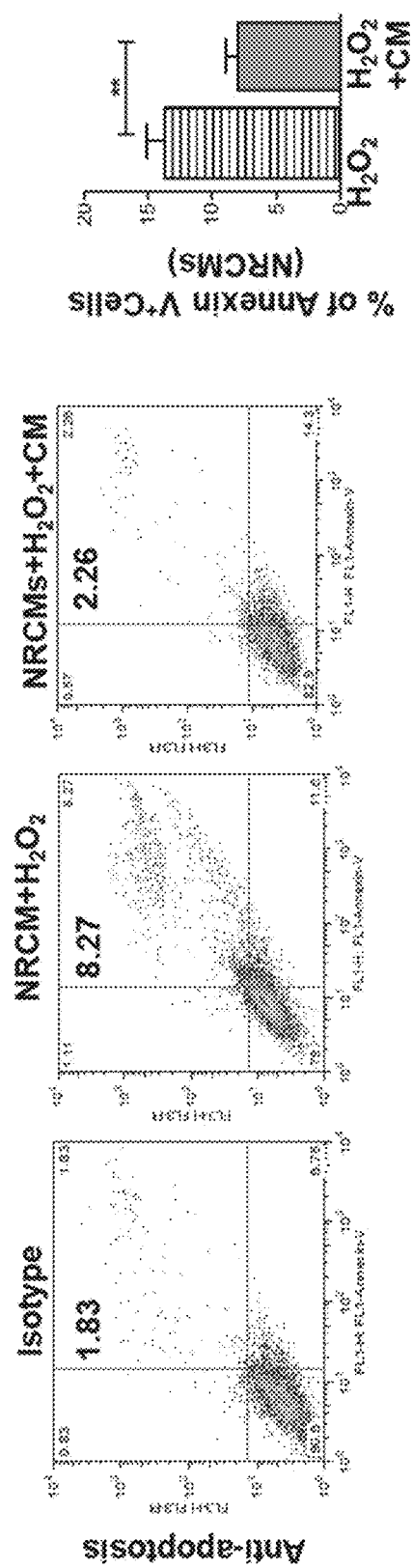
Figure 10C:
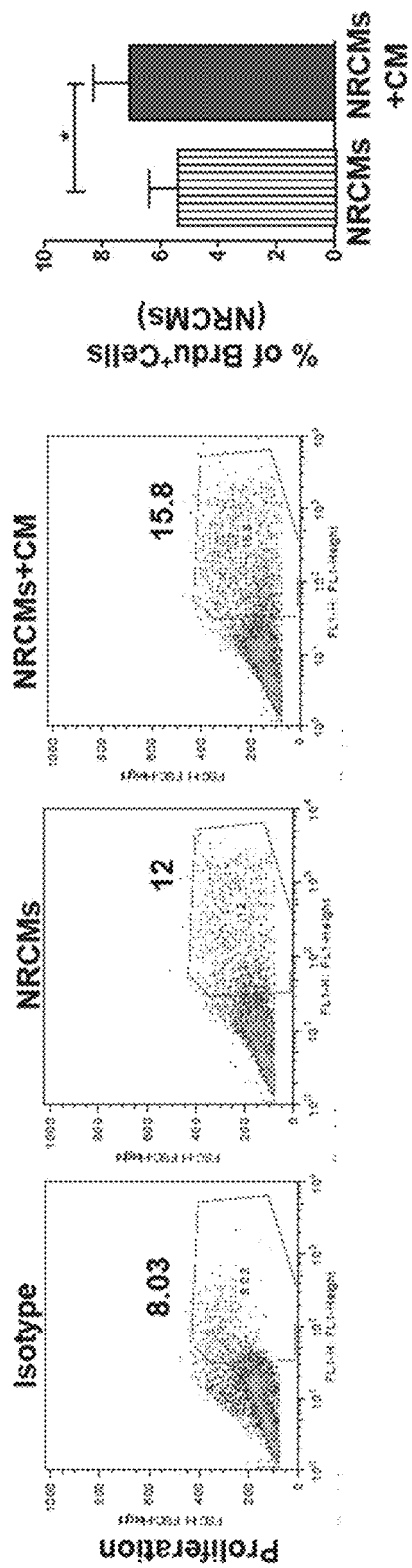
Figure 10D:
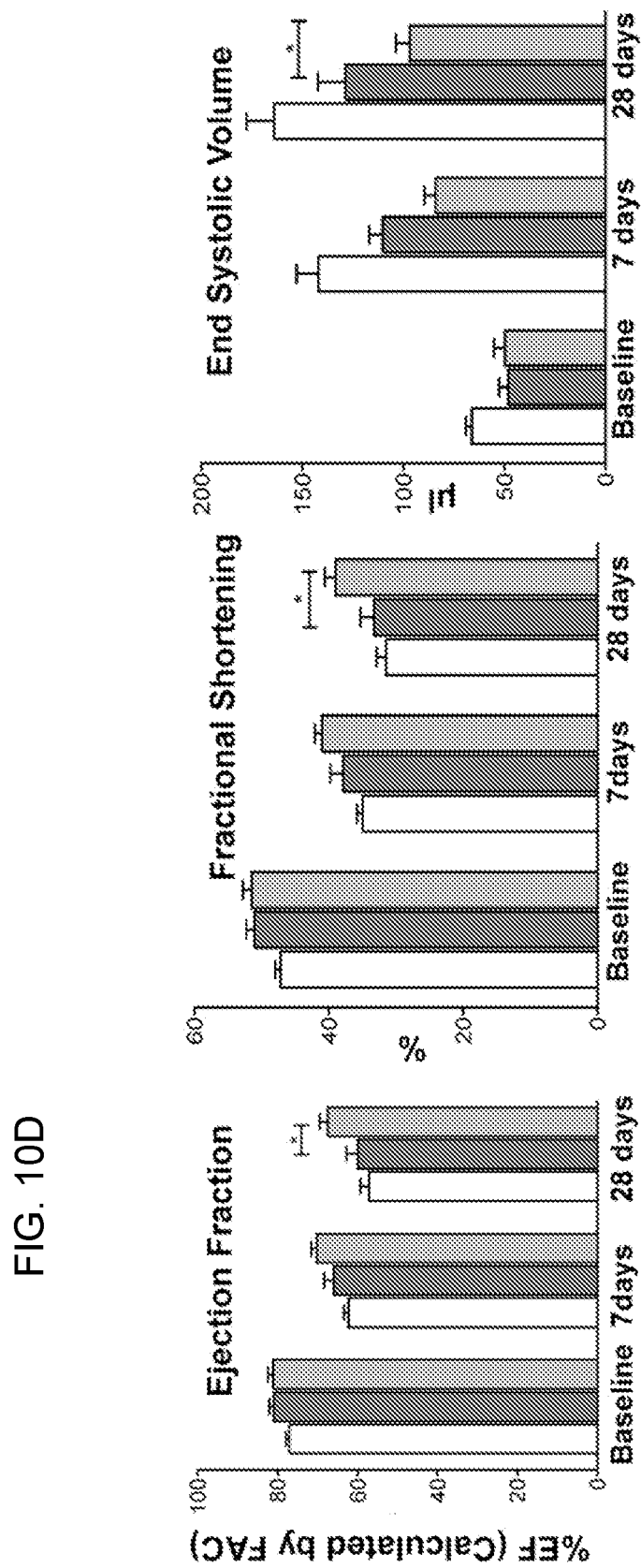
Figure 10E:
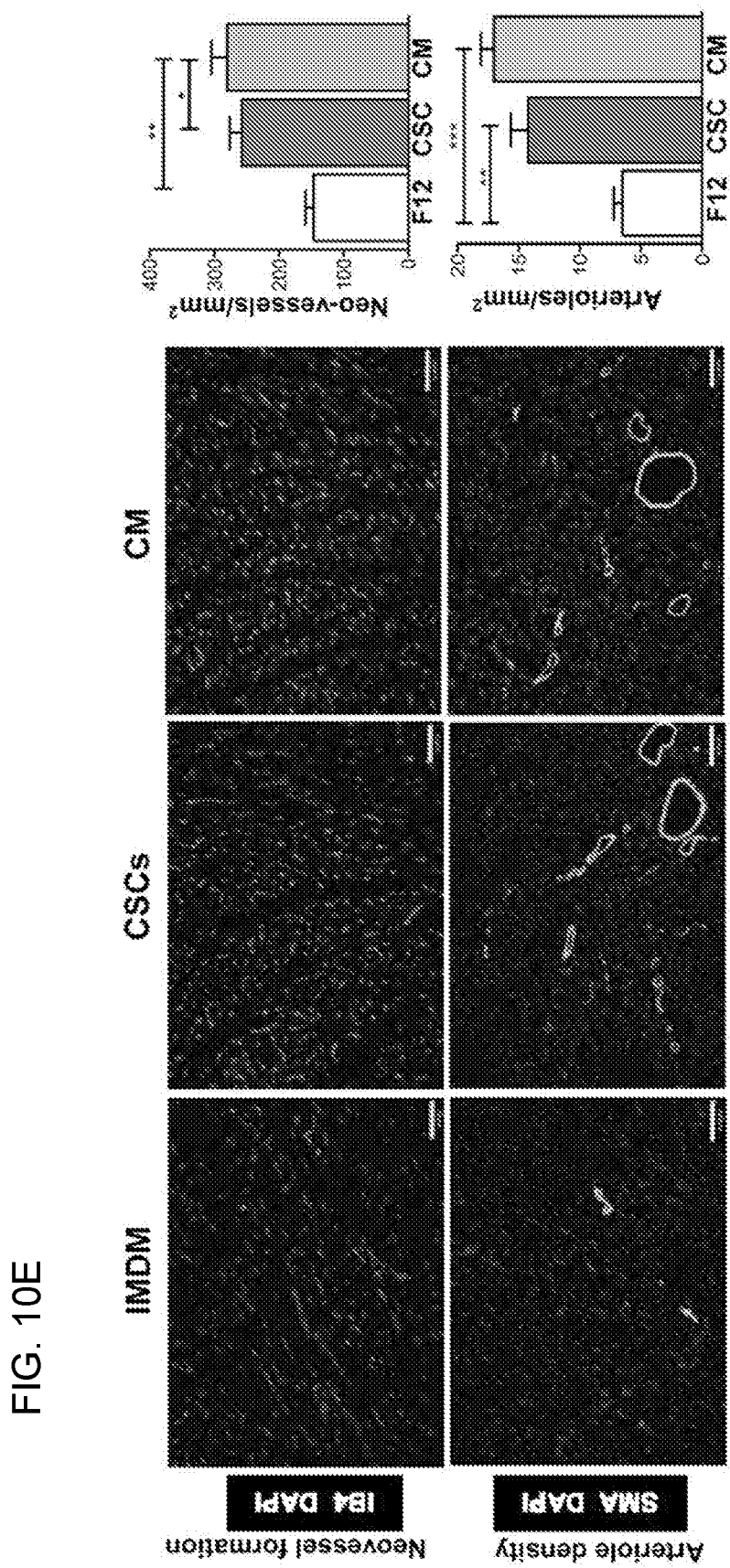

FIGS. 10A-10E. Conditioning medium (CM) of CSCs contain pro-angiogenic, pro-proliferative and anti-apoptotic factors, which can improve cardiac function and attenuate ventricular remodeling similar to CSCs transplantation in MI model. FIG. 10A). Representative images of HUVEC tube formation (left) and quantification of total tube length (right) after plating HUVEC cells on reduced growth factor matrix coated wells with IMDM condition medium from CSCs and HUVEC cells growing complete medium. Quantification shows that CSCs-CM is contains highly angiogenic property. FIG. 10B). CSCs-CM treatment significantly reduced the $H_2O_2$ induced apoptosis in NRCMs after 24 hours. FIG. 10C). CSCs-CM treatment for 48 hours significantly enhances Brdu uptake by NRCMs. FIG. 10D). Functional parameters derived from echocardiography measurements are shown. A significant increase in ejection fraction, fractional shortening and significant decrease in the end systolic volume was observed after CSCs-CM transplantation as compared to corresponding CSCs and placebo (IMDM). FIG. 10E). Immunofluorescence demonstrated increased formation of neovessels marked by IB4 expression and of arterioles marked by a-SMA expression in rat myocardium sections of the mid-infarct regions injected with CSCs-CM than transplanted with CSCs.

Figure 11A:
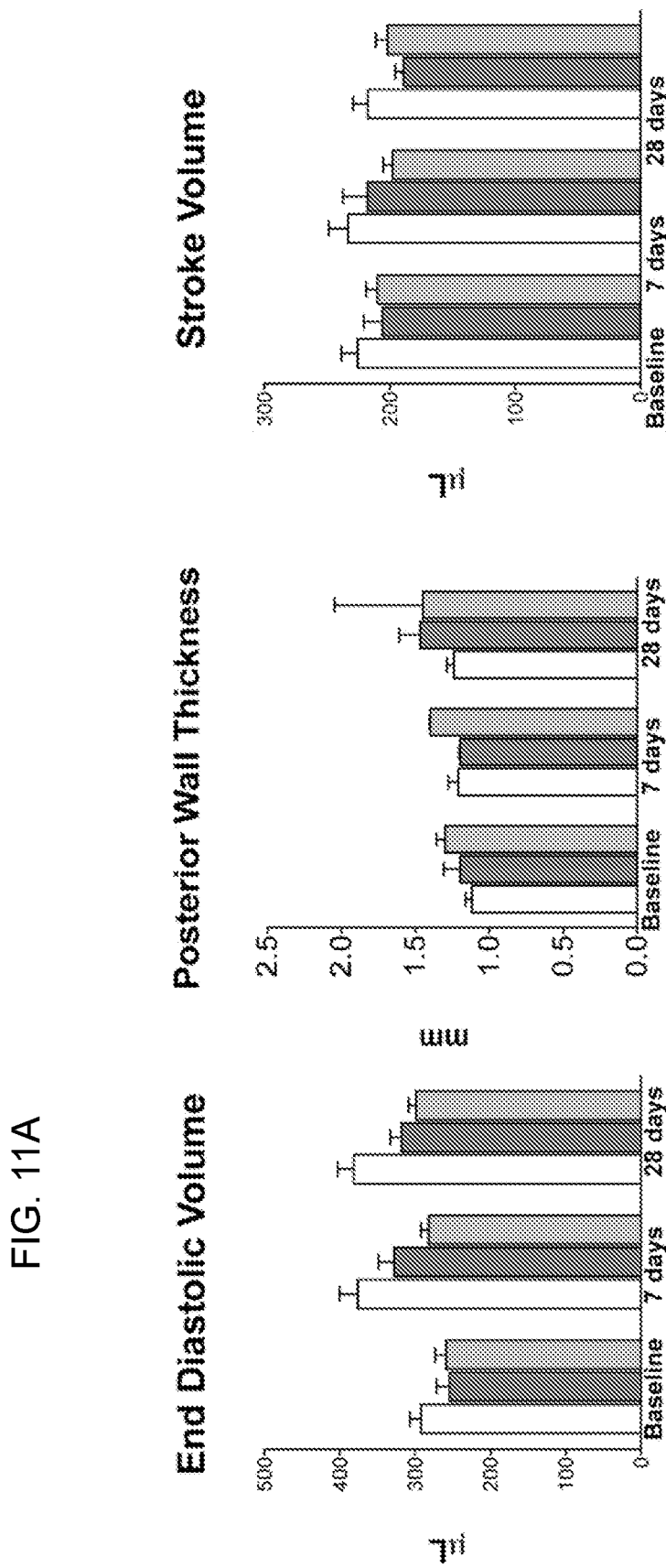
FIGS. 11A, 11B, and 11C represent cardiac function and structure improvement by CSCs-CM.
Figure 11B:
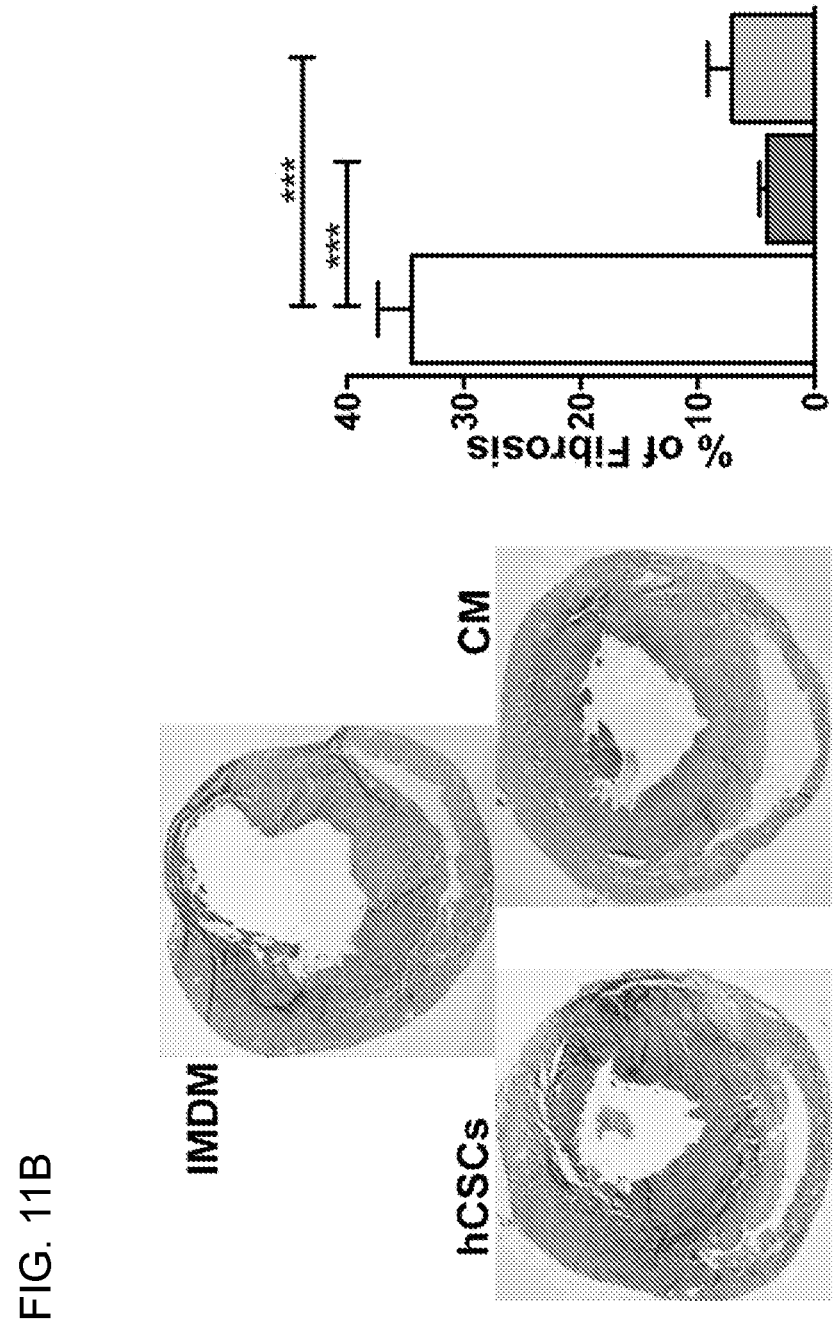
Figure 11C:
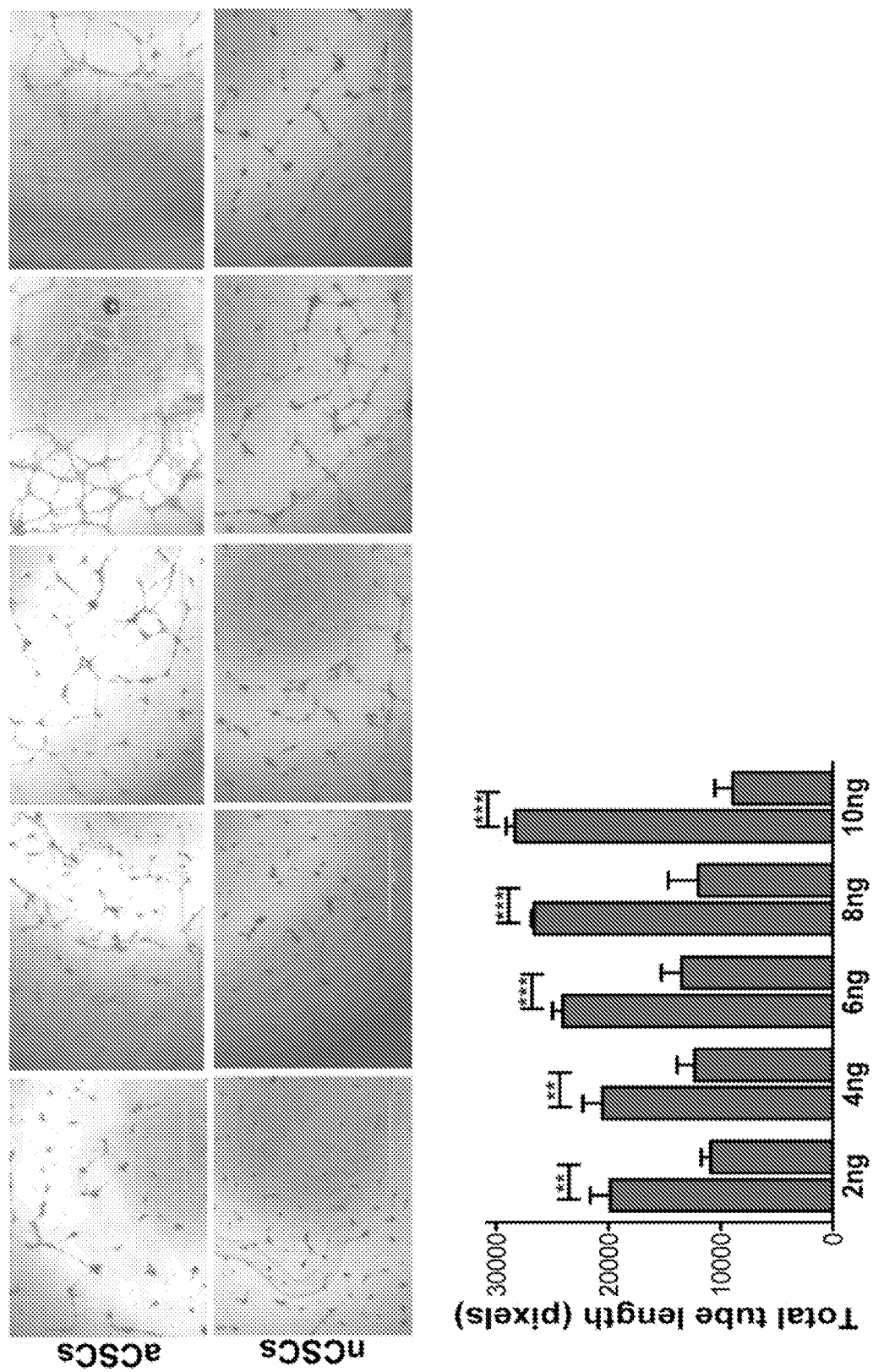

FIGS. 11A-11C. Cardiac function and structure improvement by CSCs-CM. FIG. 11A). End diastolic volume, posterior wall thickness and stroke volume were not affected by injection of CSCs-CM or CSCs. FIG. 10B). Infarct size determined by Masson's trichrome staining was reduced with injected CSC-CM when compared with IMDM or CSCs. FIG. 10C). Angiogenic potential of nCSCs-CM and aCSC-CM. nCSCs-CM shows higher angiogenic potential as compared to aCSC-CM. The angiogenic potential of aCSCs actually decreases with increase in the amount.

Figure 12A:
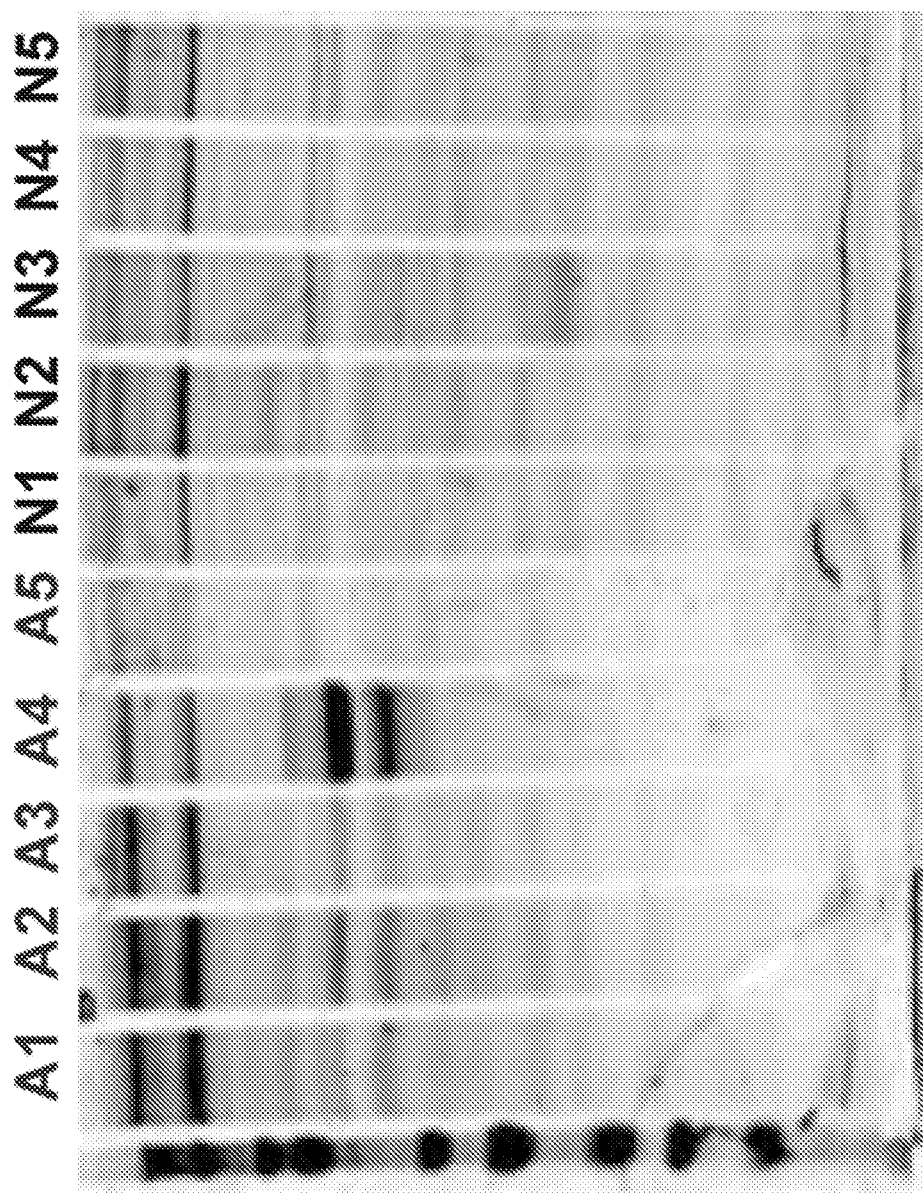
FIGS. 12A, 12B, 12C, 12D, 12E, 12F, and 12G provide a comparative analysis of the secretome of aCSCs and nCSCs by LC-MS/MS.
Figure 12B:
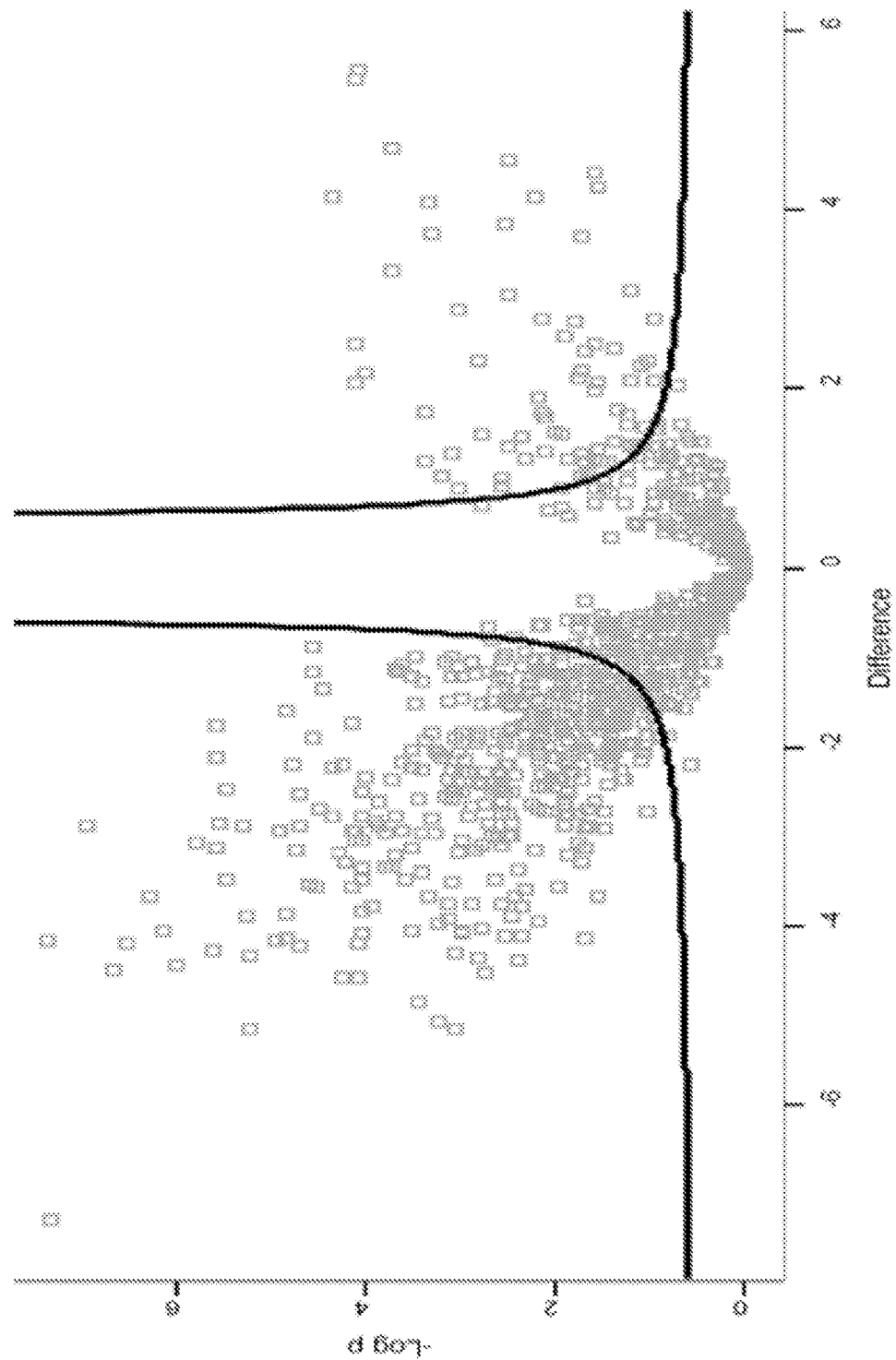
Figure 12C:
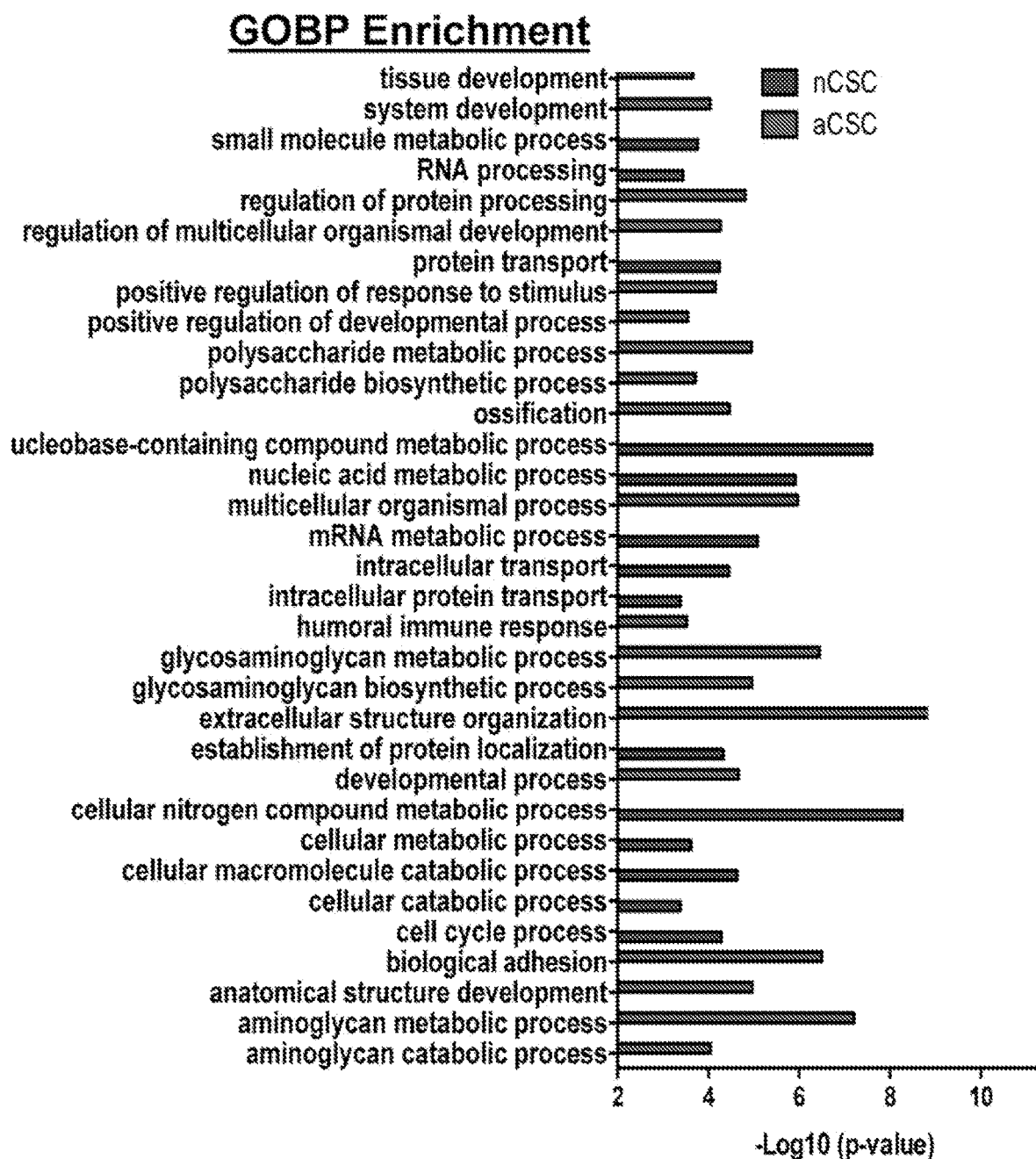
Figure 12D:
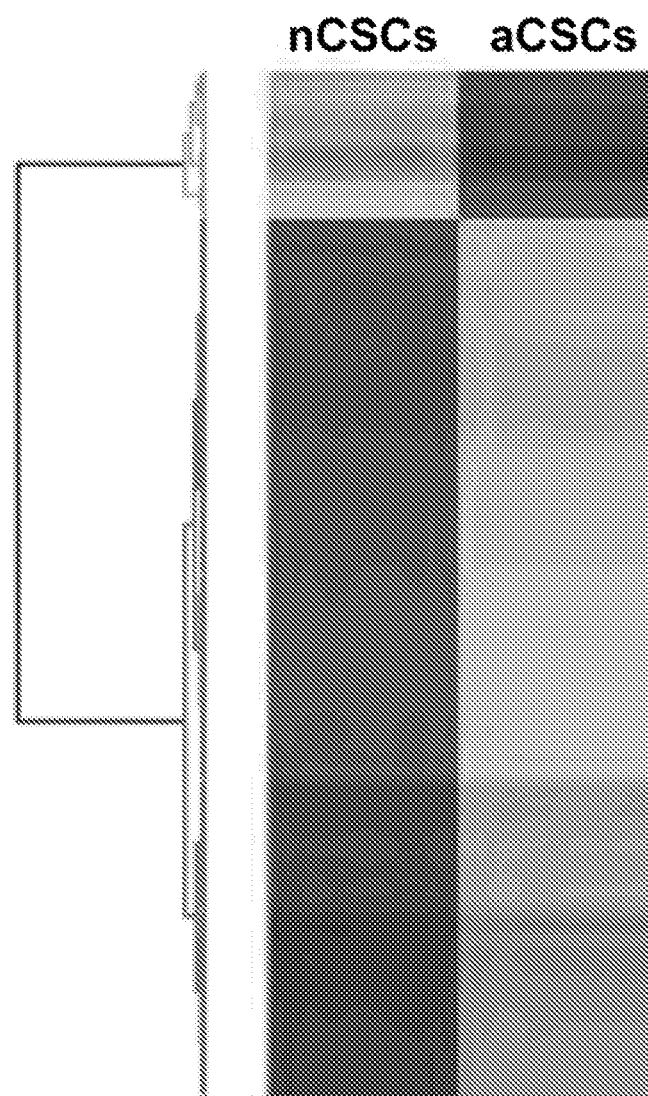
Figure 12E:
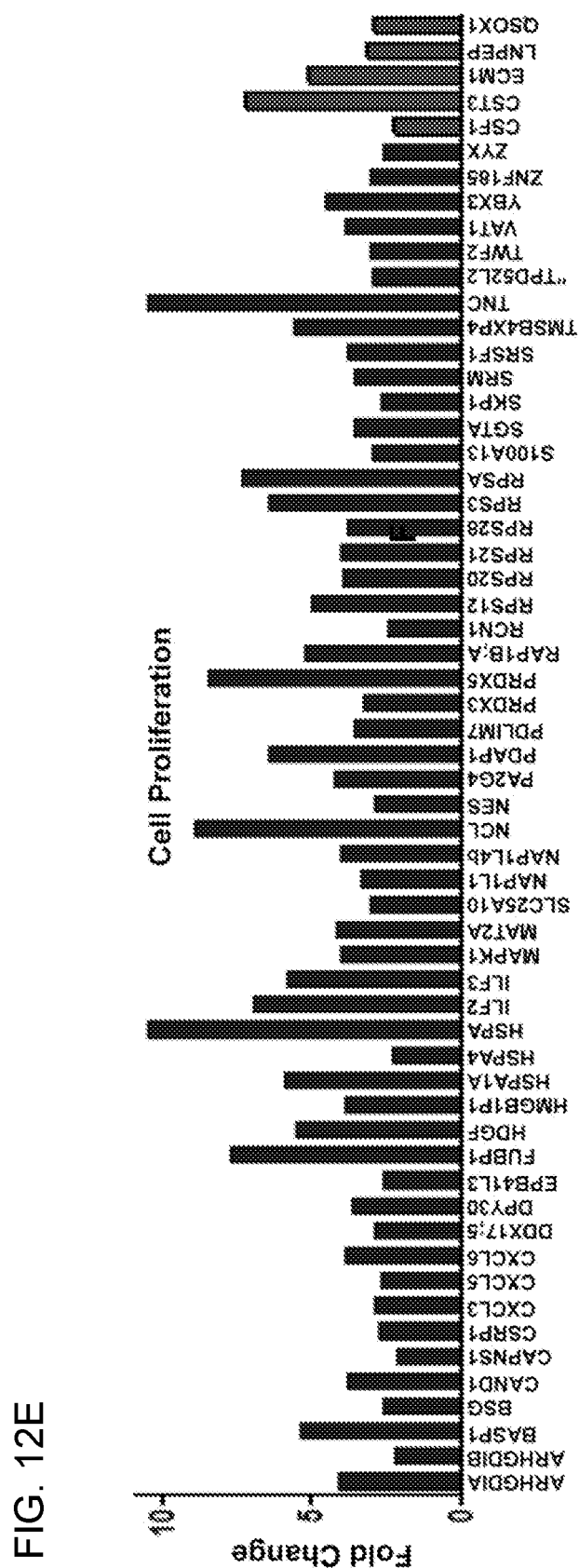
Figure 12F:
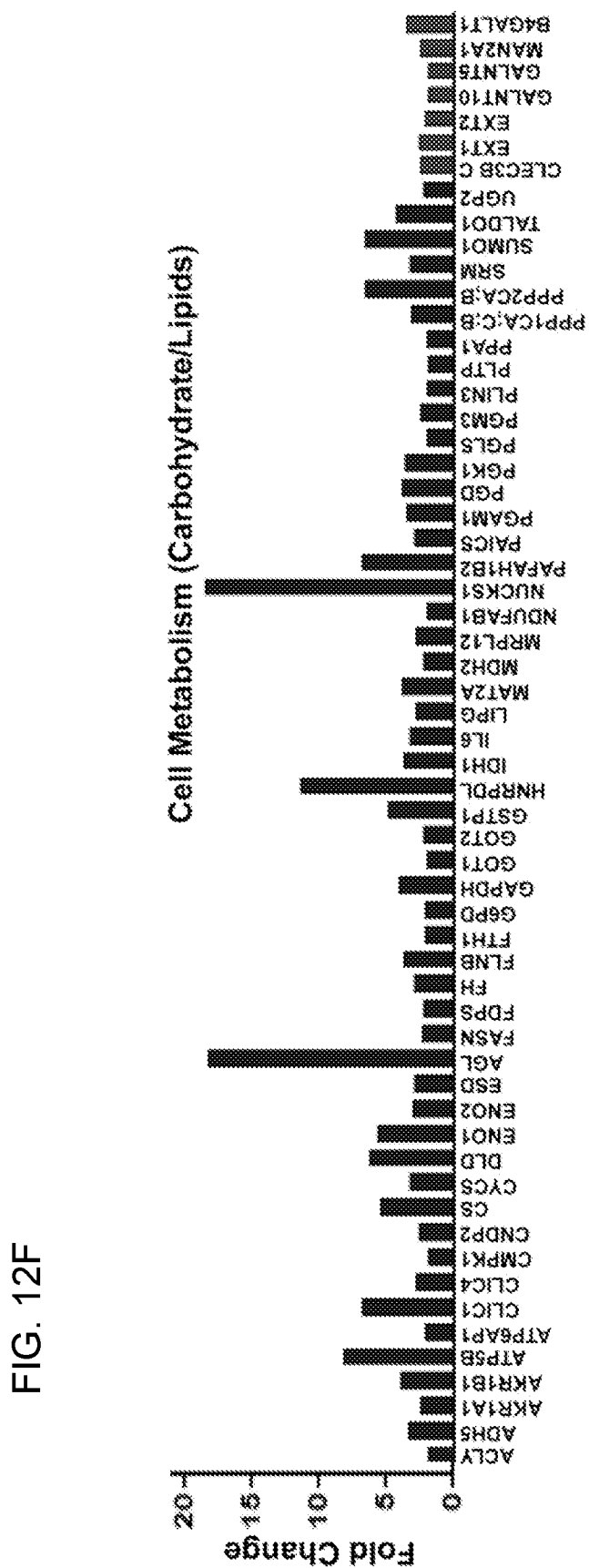
Figure 12G:
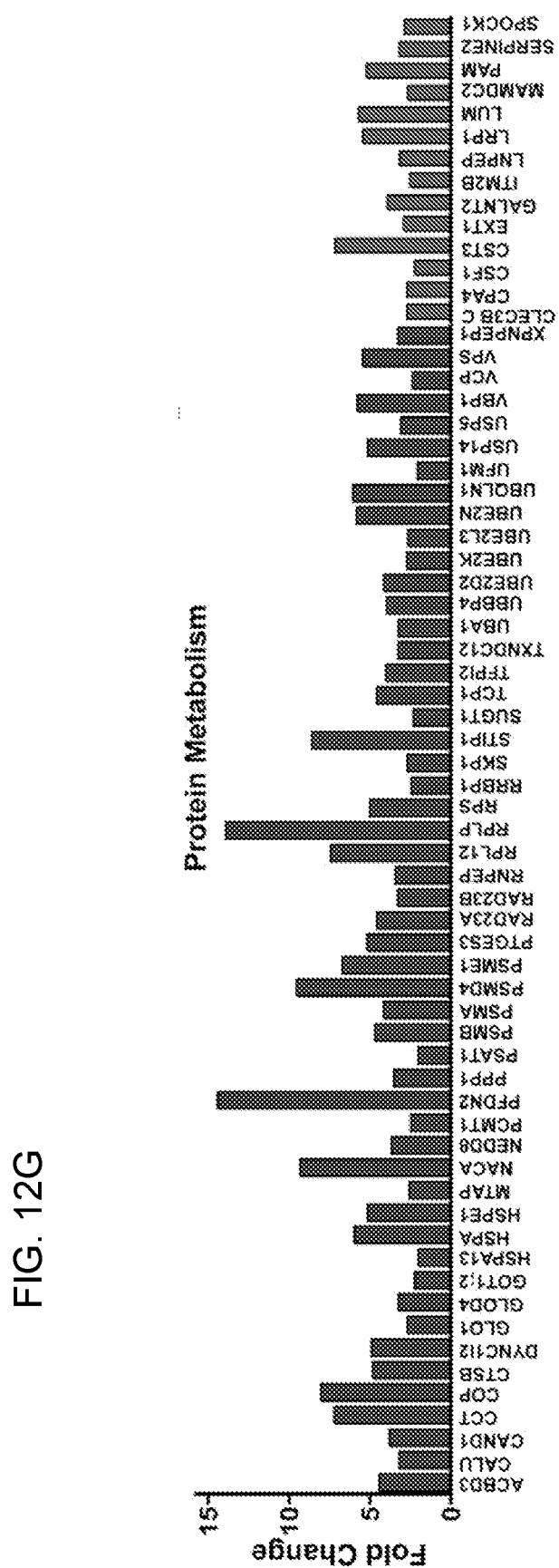

FIGS. 12A-12G. Comparative analysis of the secretome of aCSCs and nCSCs by LC-MS/MS. FIG. 12A). The presence of proteins and their integrity in nCSCs-Cm and aCSC-CM (5 different biological samples each) was determined by SDS-PAGE analysis. FIG. 12B). Volcano plot showing the distribution of the proteins. Proteins with more than 2 fold change further analyzed. FIG. 12C). The identified proteins were subjected to GOBP (Gene ontology biological process) and various categories of proteins was identified. FIG. 12D). Heat plot showing the average of protein expression in nCSC-CM and aCSC-CM. The proteins identified in nCSCs-CM and aCSC-CM with their roles in Cell proliferation (FIG. 12E), Cell metabolism (FIG. 12F) and protein metabolism (FIG. 12G).

Figure 13A:
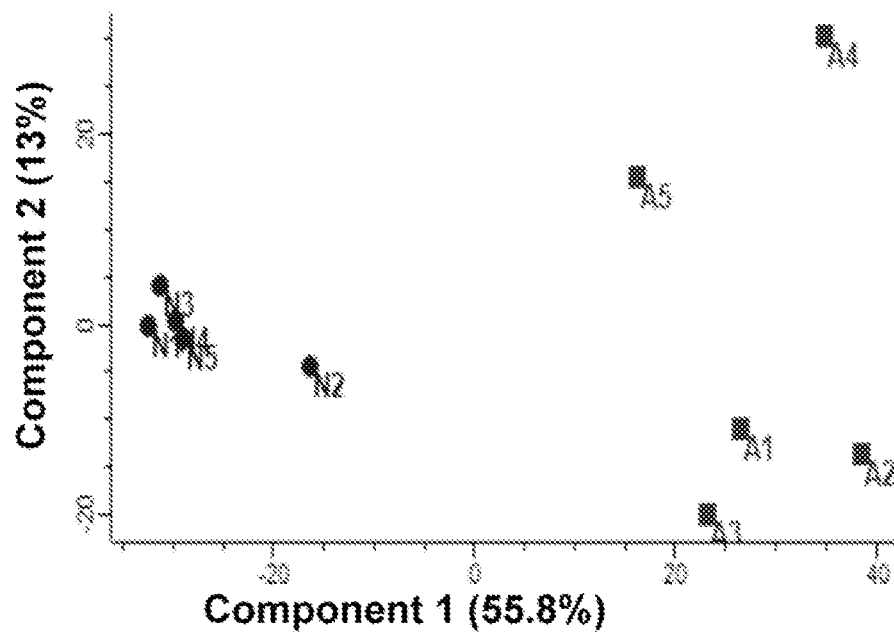
FIGS. 13A, 13B, 13C, 13D, 13E, 13F, 13G, 13H, 13I, 13J, 13K, 13L, 13M, and 13N show total Proteome analysis of the aCSC and nCSCs secretome identified by LC-MS/MS.
Figure 13B:
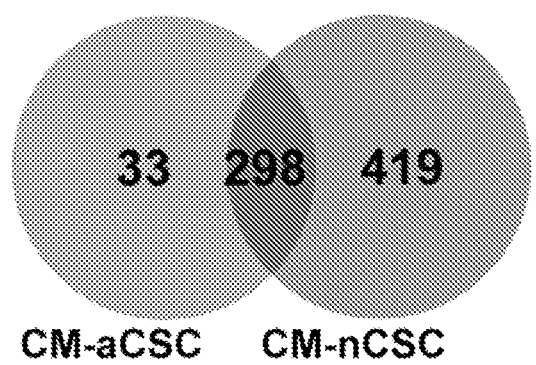
Figure 13C:
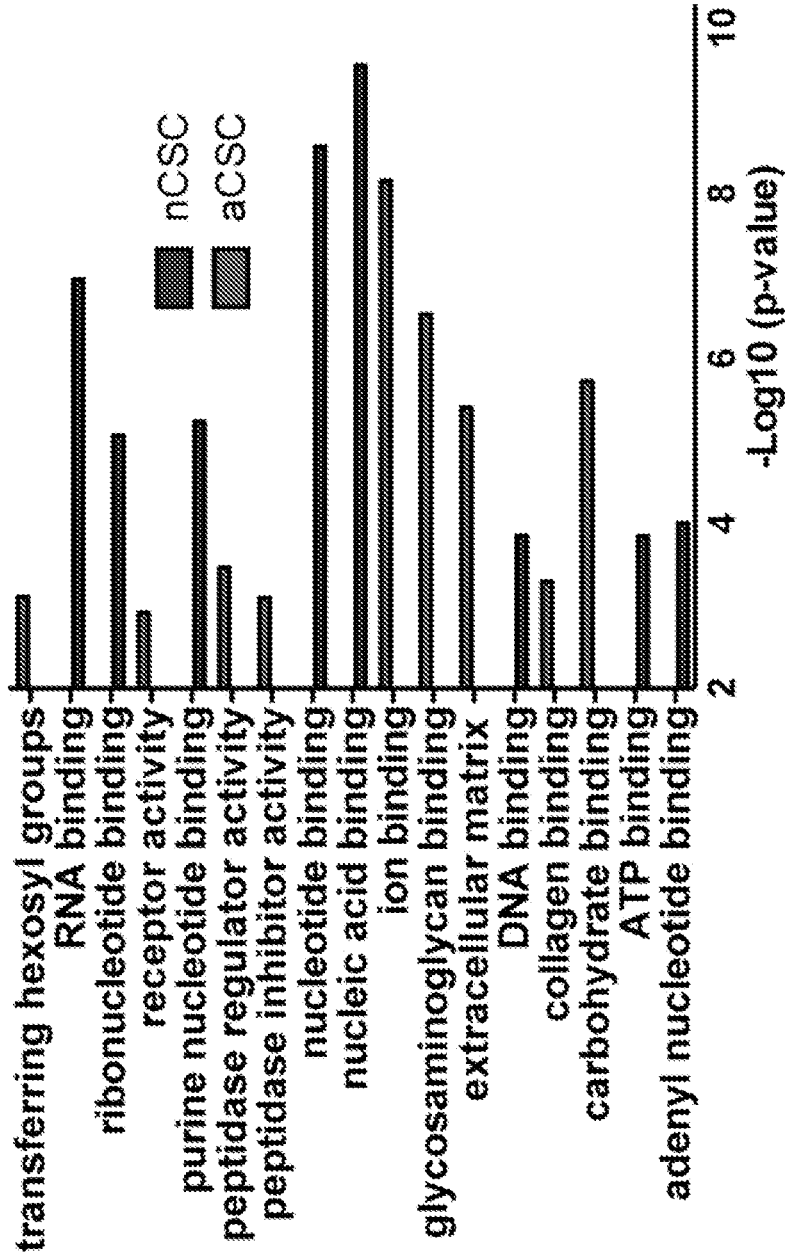
Figure 13D:
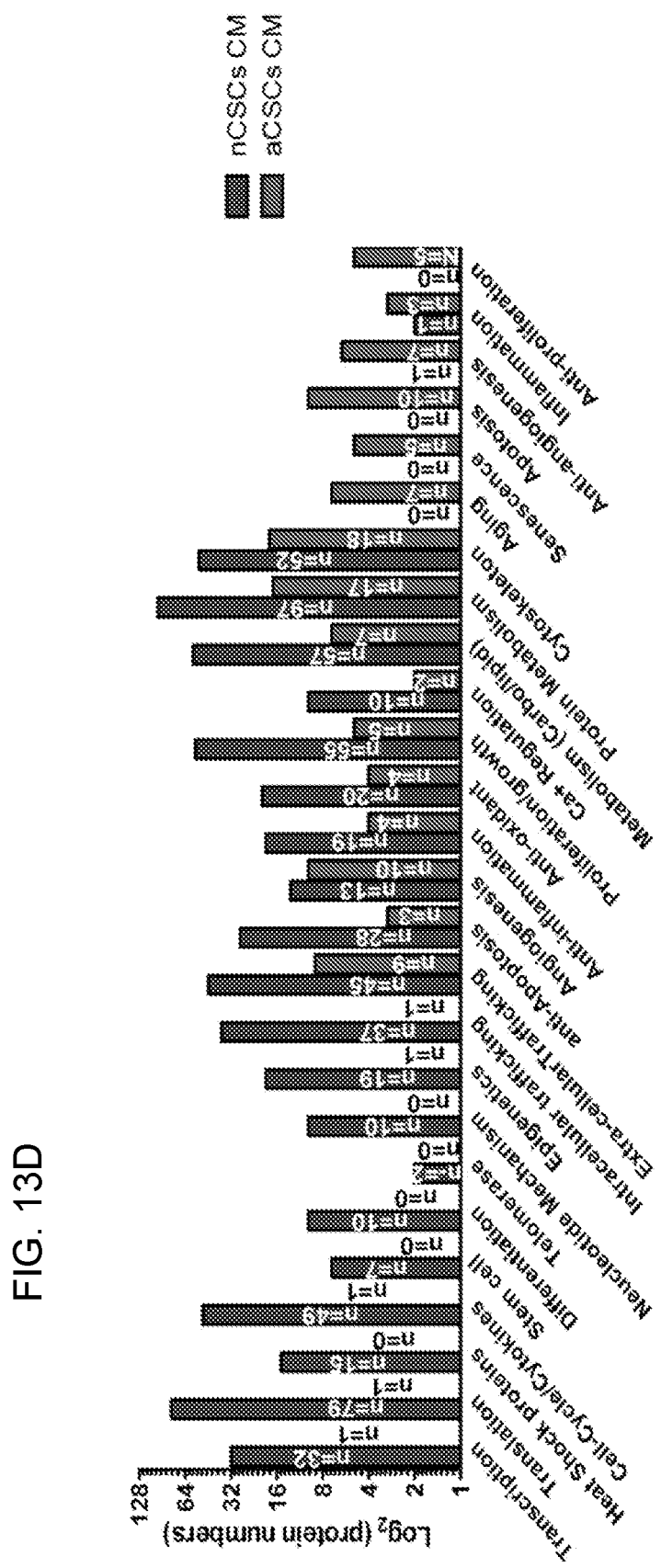
Figure 13F:
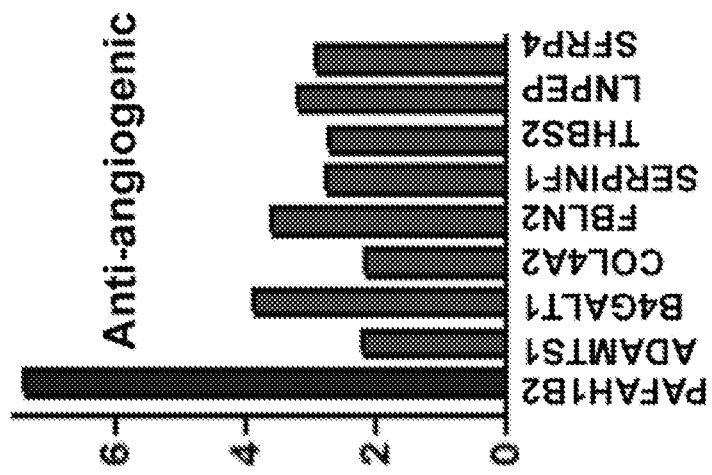
Figure 13E:
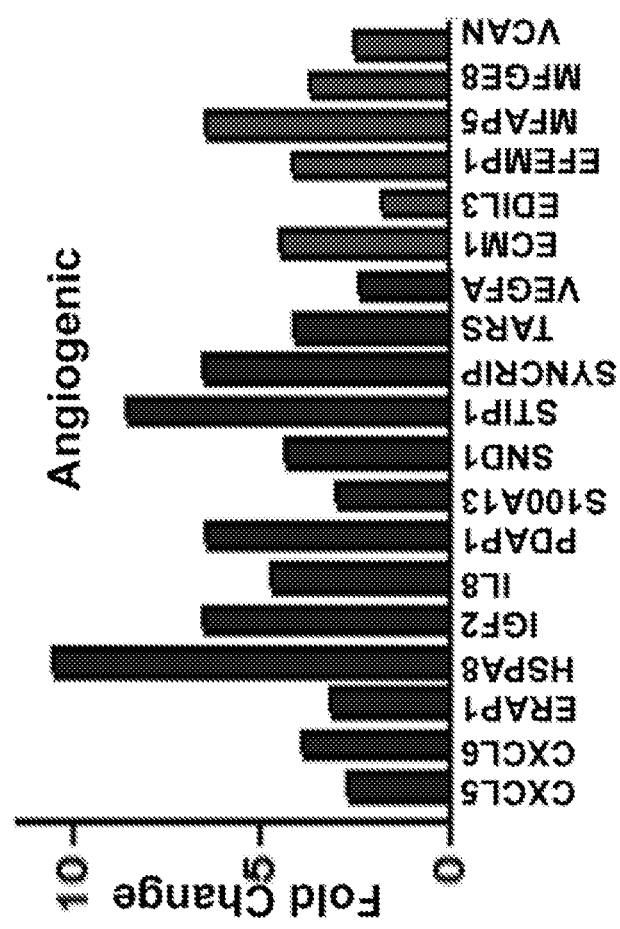
Figures 13G, 13H:
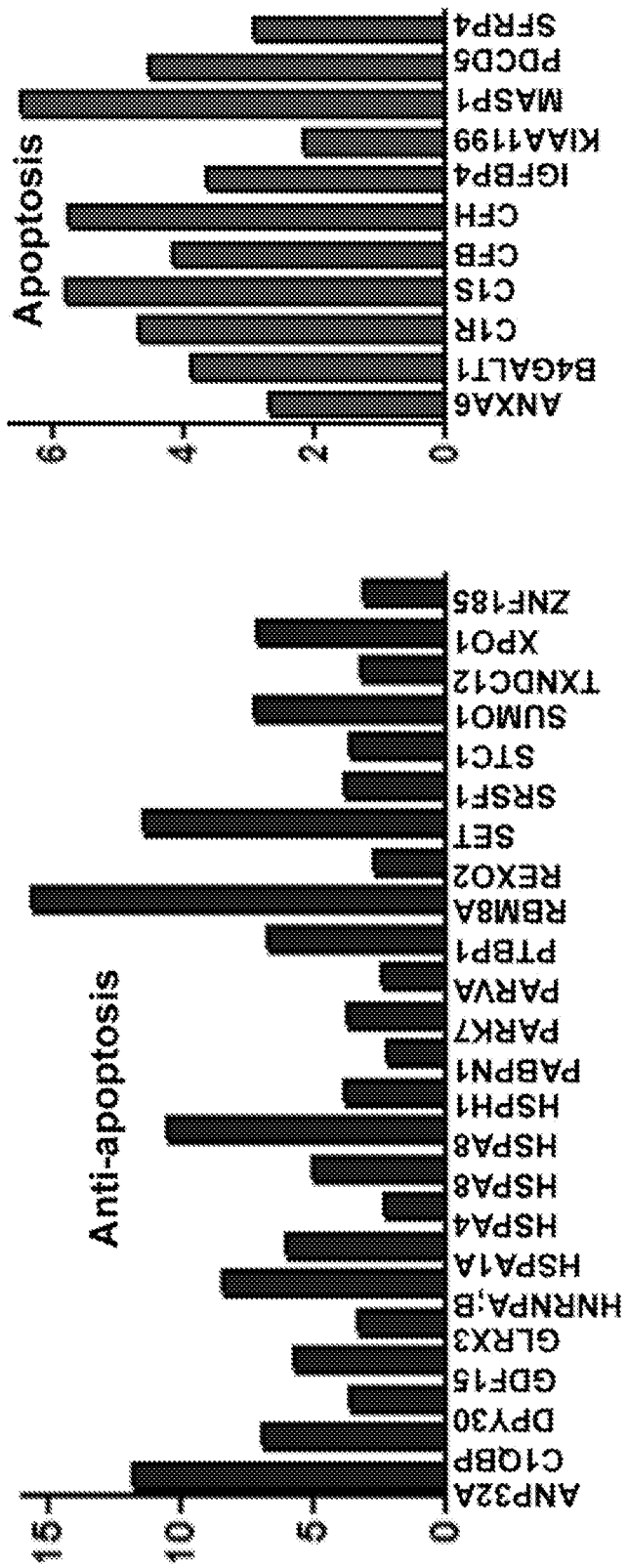
Figure 13J:
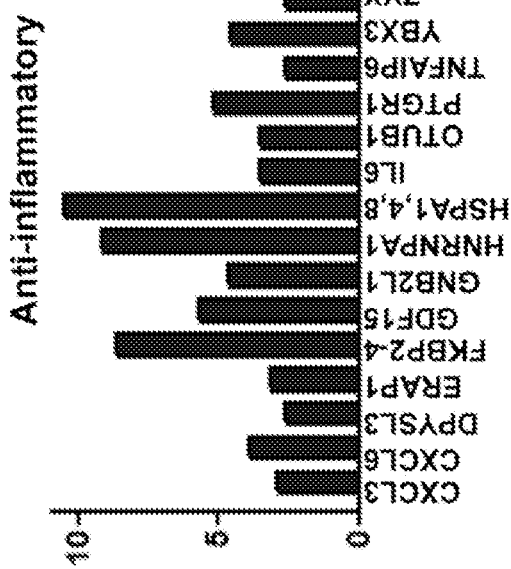
Figure 13I:
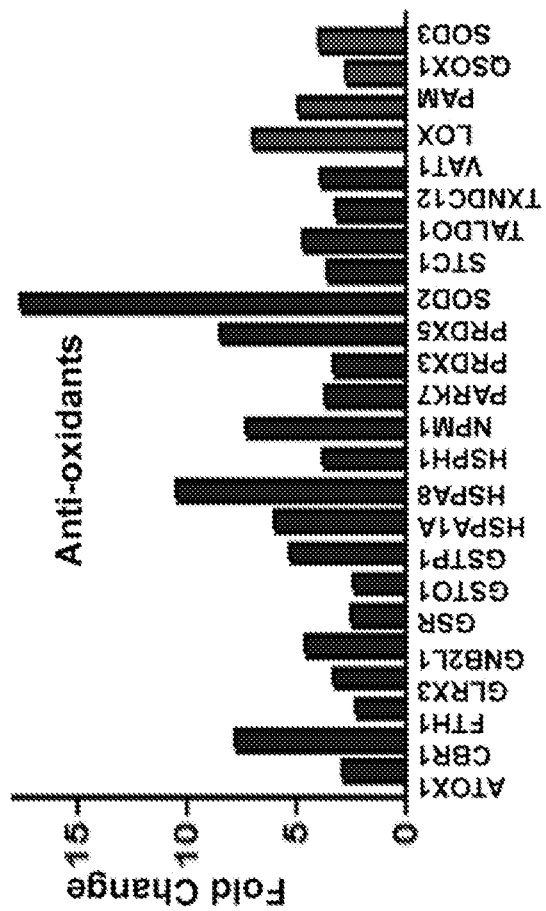
Figure 13M:
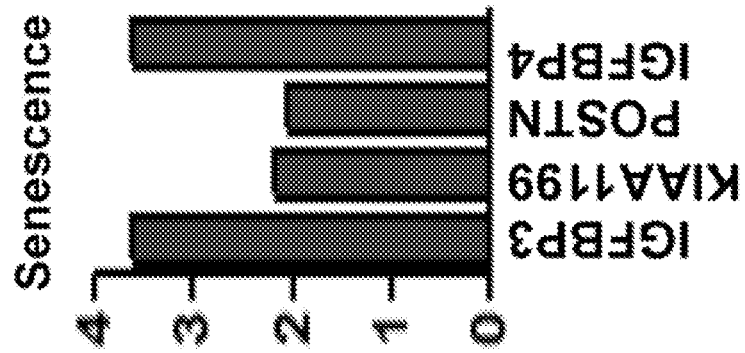
Figure 13L:
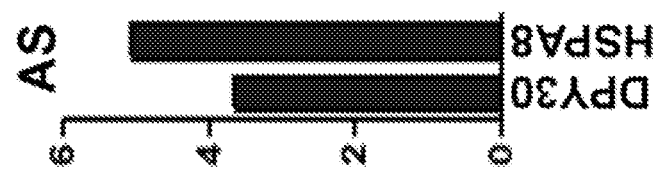
Figure 13K:
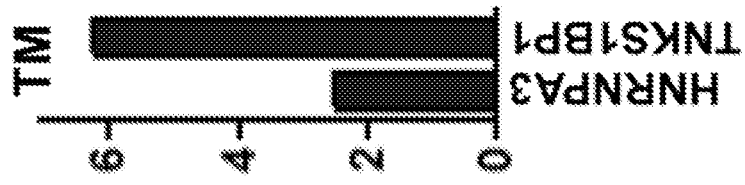
Figure 13N:
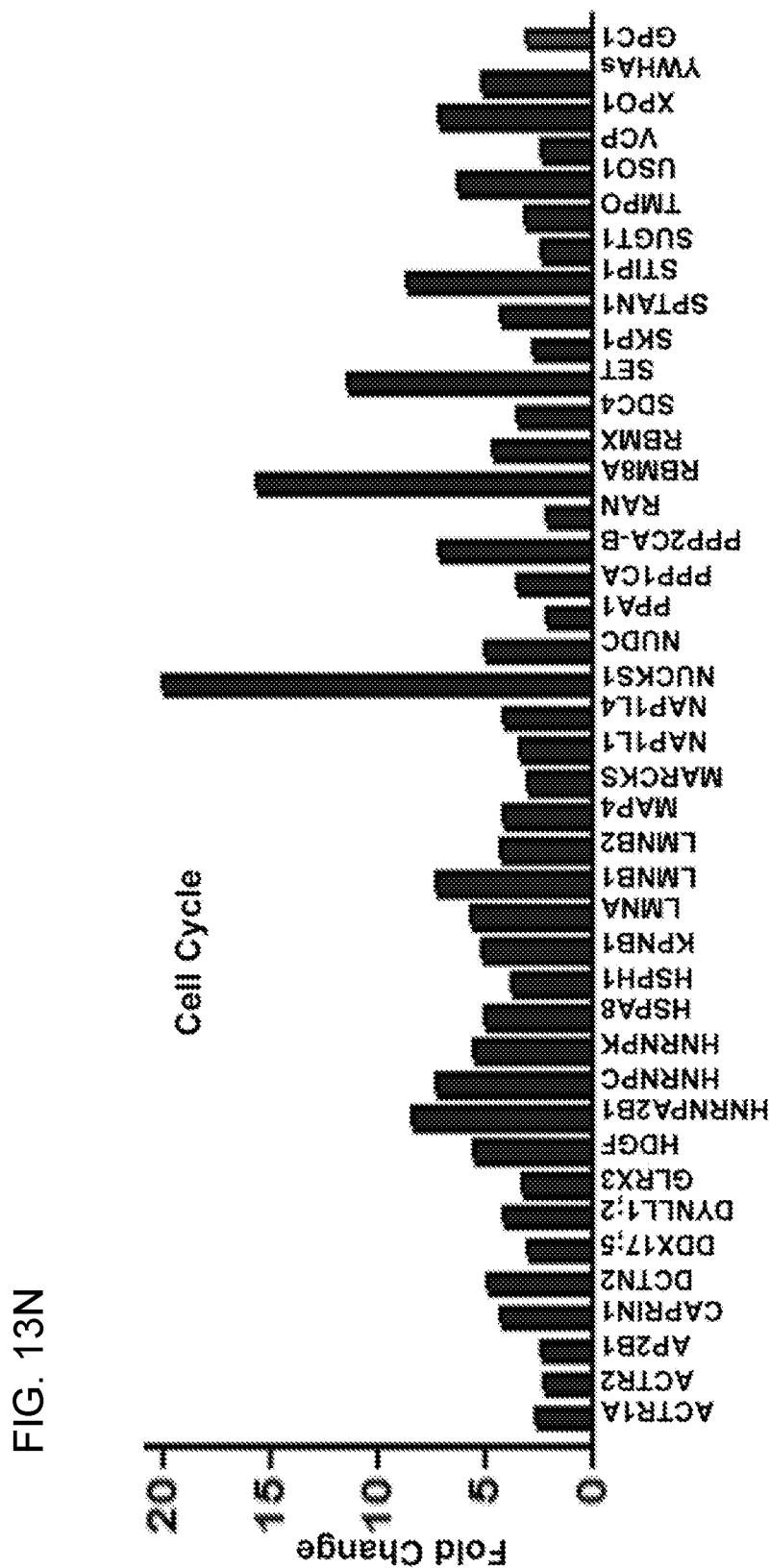
Figure 14A:
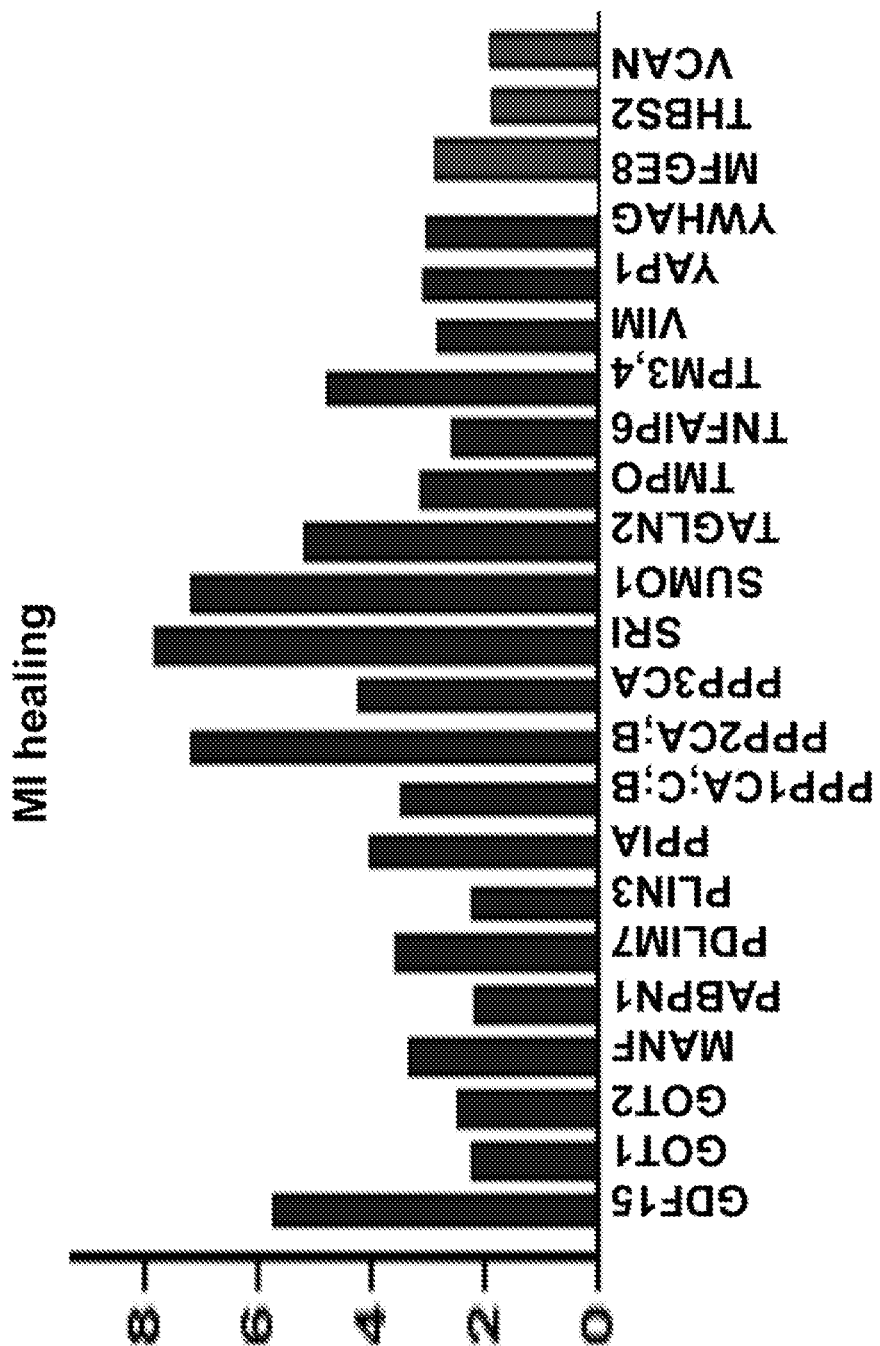
FIGS. 14A, 14B, 14C, 14D, 14E, and 14F represent total Proteome analysis of the aCSC and nCSCs secretome identified by LC-MS/MS.
Figure 14B:
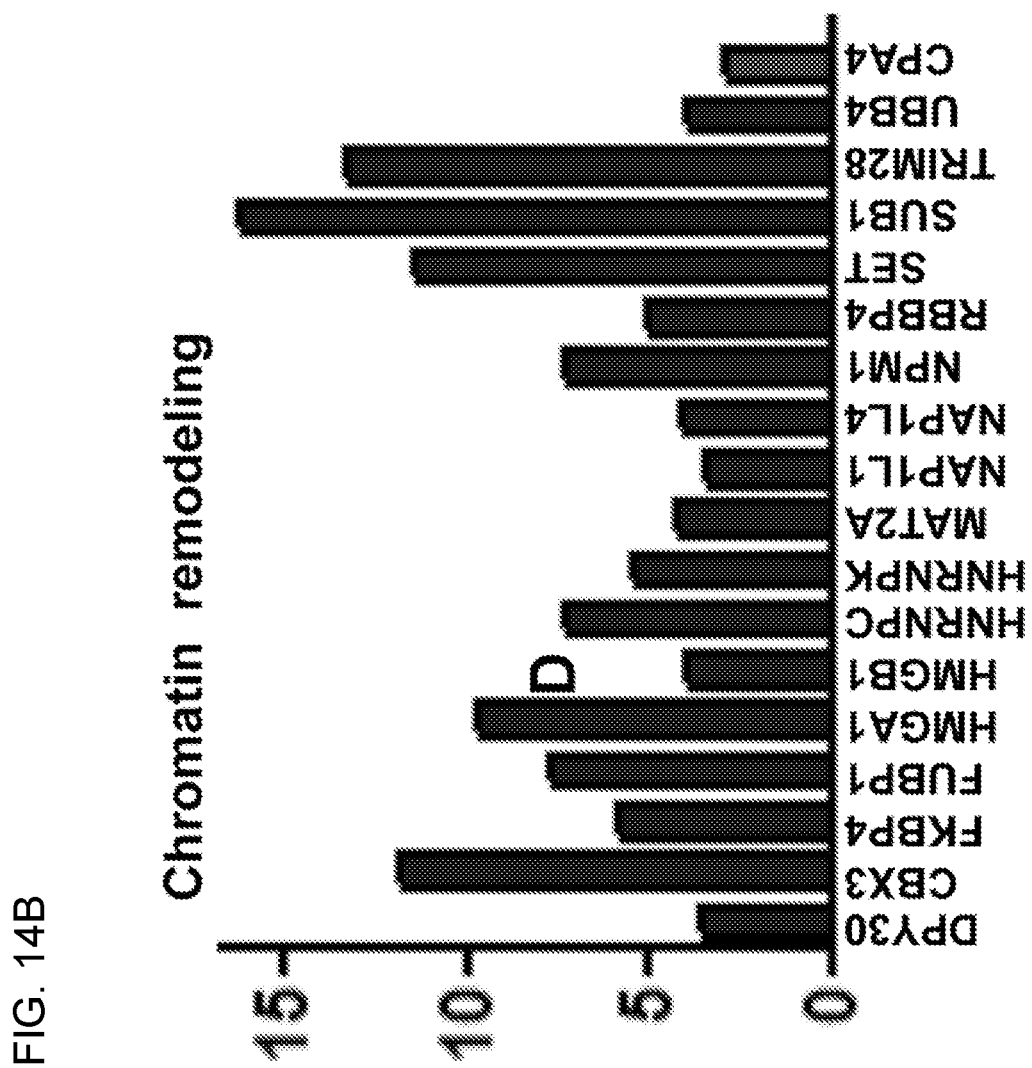
Figure 14E:
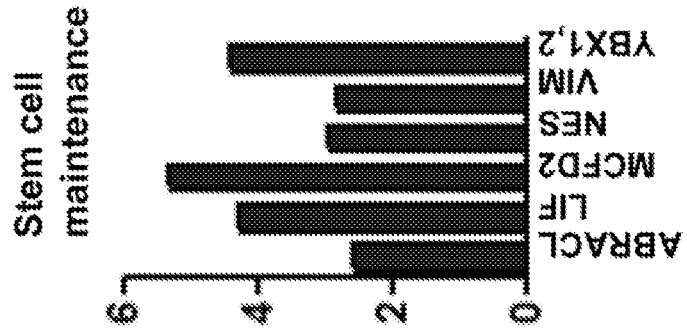
Figure 14D:
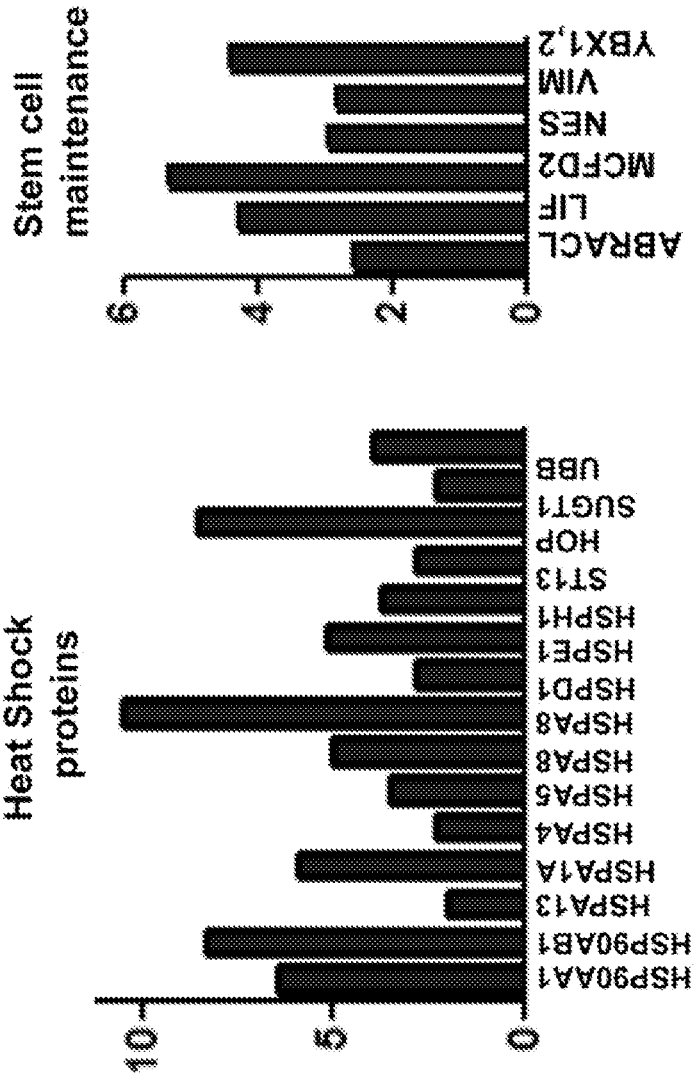
Figure 14C:
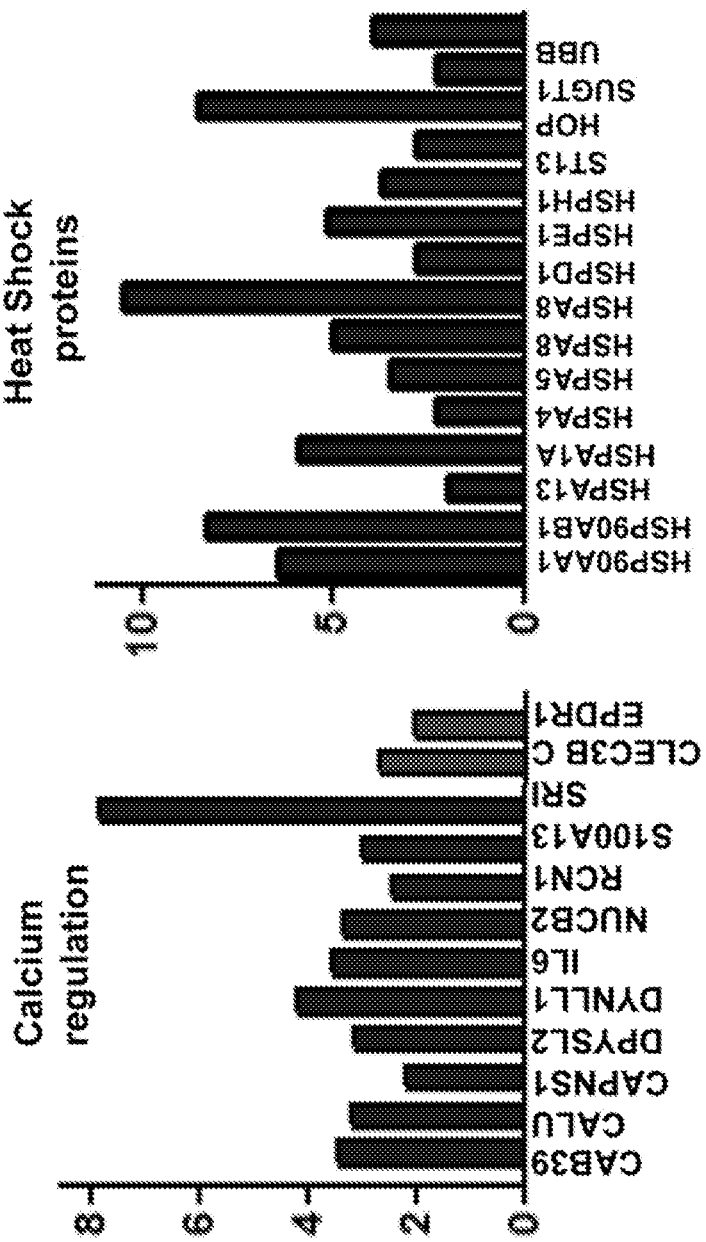
Figure 14F:
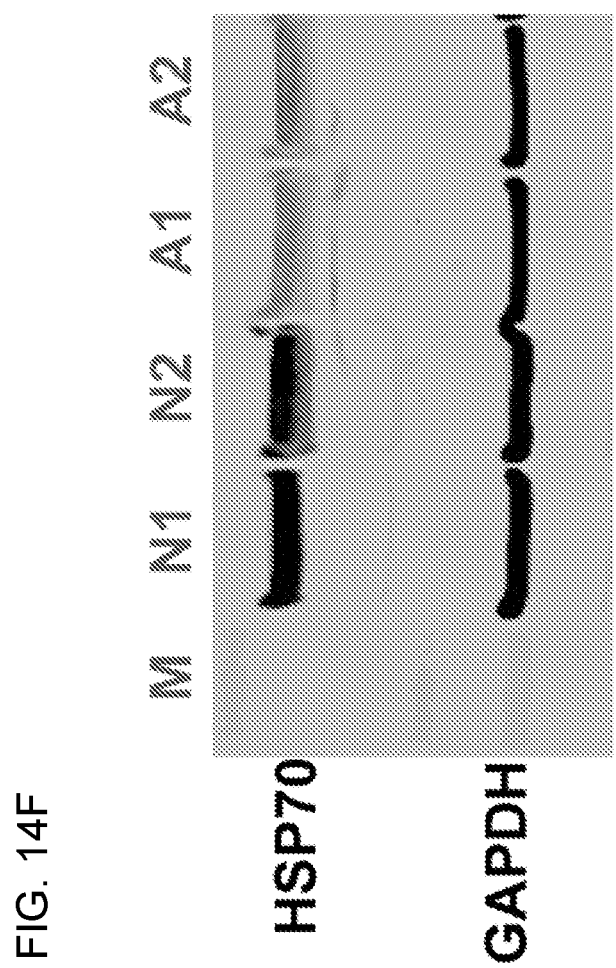

FIGS. 13A-13N. Total Proteome analysis of the aCSC and nCSCs secretome identified by LC-MS/MS. FIG. 13A). Principal component analysis (PCA) of nCSC-CM and aCSC-CM suggested the similarity between nCSC-Cm while great deal of diversity was with the aCSC-CM. FIG. 13B). Venn diagram showed the protein expression from nCSCs-CM and aCSCs-CM. FIG. 13C). GOMF enrichment showed that the majority of proteins in nCSC-CM were nucleotide binding while the majority of proteins in aCSCs-CM were carbohydrate or collagen binding. FIG. 13D). The proteins were classified according to their roles relevant to cardiac development and represented as number of proteins in every identified group from nCSCs-CM and aCSCs-CM. The graph showing proteins identified from nCSCs-CM and aCSCs-CM with angiogenic potential (FIG. 13E), anti-angiogenic potential (FIG. 13F), anti-apoptosis potential (FIG. 13G), apoptotic potential (FIG. 13H), anti-oxidants (FIG. 13I), anti-inflammatory (FIG. 13J), telomere length maintenance (FIG. 13K), anti-senescence (FIG. 13L), senescence (FIG. 13M) and cell cycle inducing or proliferation induction (FIG. 13N).

FIGS. 14A-14E. Total Proteome analysis of the aCSC and nCSCs secretome identified by LC-MS/MS. The graph showing proteins identified from nCSCs-CM and aCSCs-CM with myocardial infarction healing (FIG. 14A), chromatin modeling (FIG. 14B), calcium regulation (FIG. 14C), heat shock proteins (FIG. 14D) and stem cell maintenance. (FIG. 14E) Western blot showing the expression of heat shock protein 70 in nCSC and aCSCs.

FIGS. 15A-15B. Isolation of exosomes from c-kit+ cardiac stem cells. FIG. 15A). Transmission electron microscopy (TEM) image of exosomes isolated form c-kit+ CSCs using FIG. 15B). Exosomes were identified by immunogold staining for CD63 cell surface antigen.

Figure 16A:
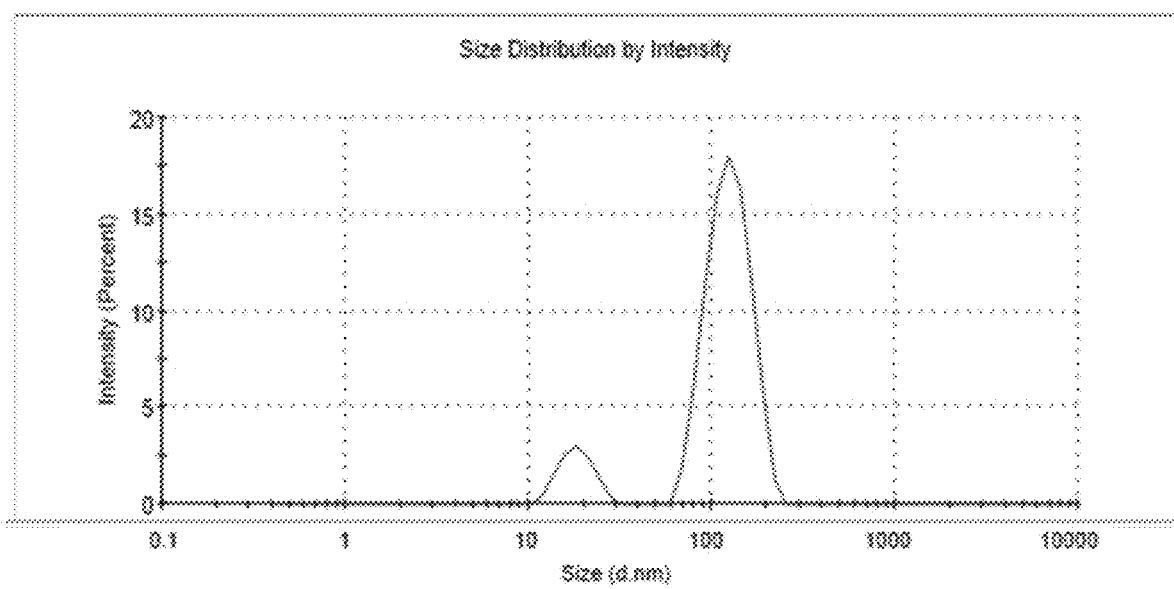
FIGS. 16A and 16B are characterization of exosomes from c-kit+ cardiac stem cells.
Figure 16B:
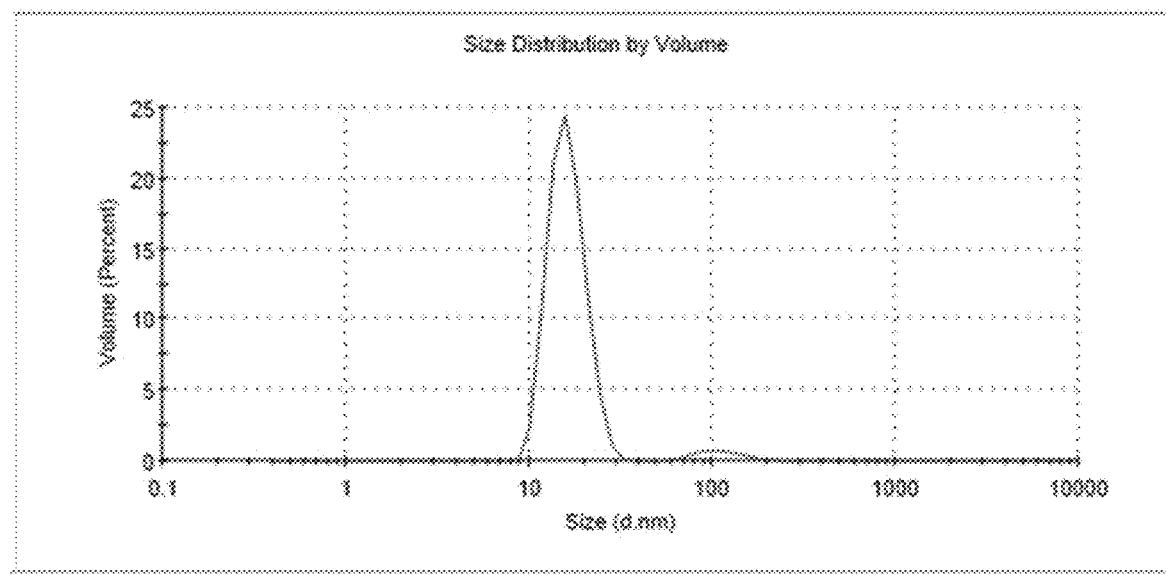

FIGS. 16A-16B. Characterization of exosomes from c-kit+ cardiac stem cells. FIG. 16A). Exosomes were isolated from c-kit+ CSCs and characterized using ZETA-SIZER® for their size distribution. FIG. 16B). The average size of exosomes identified using ZETASIZER® was identified as 30-50 nM.

Figure 17:
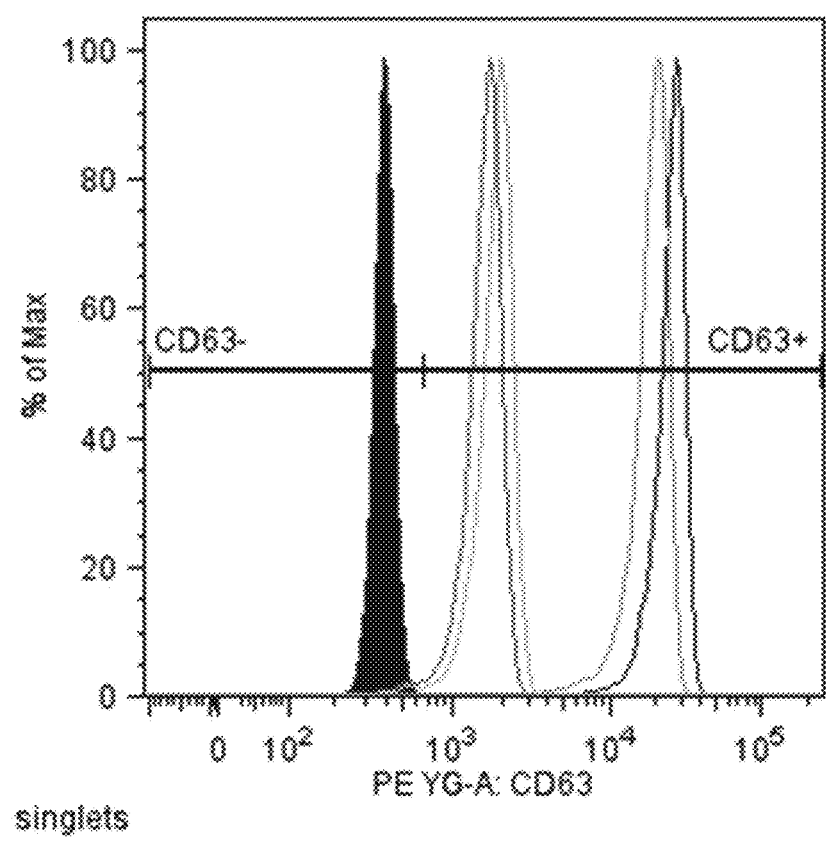
FIG. 17 is a characterization of exosomes isolated from c-kit+ cardiac stem cells.

FIG. 17. Characterization of exosomes isolated from c-kit+ cardiac stem cells. Exosomes were isolated from c-kit+ CSCs and CDCs. FACS analysis of exosomes using CD68 and PE labeled magnetic beads showed that the average size of exosomes isolated from CDCs was found to be bigger than c-kit+ CSCs.

Figure 18A:
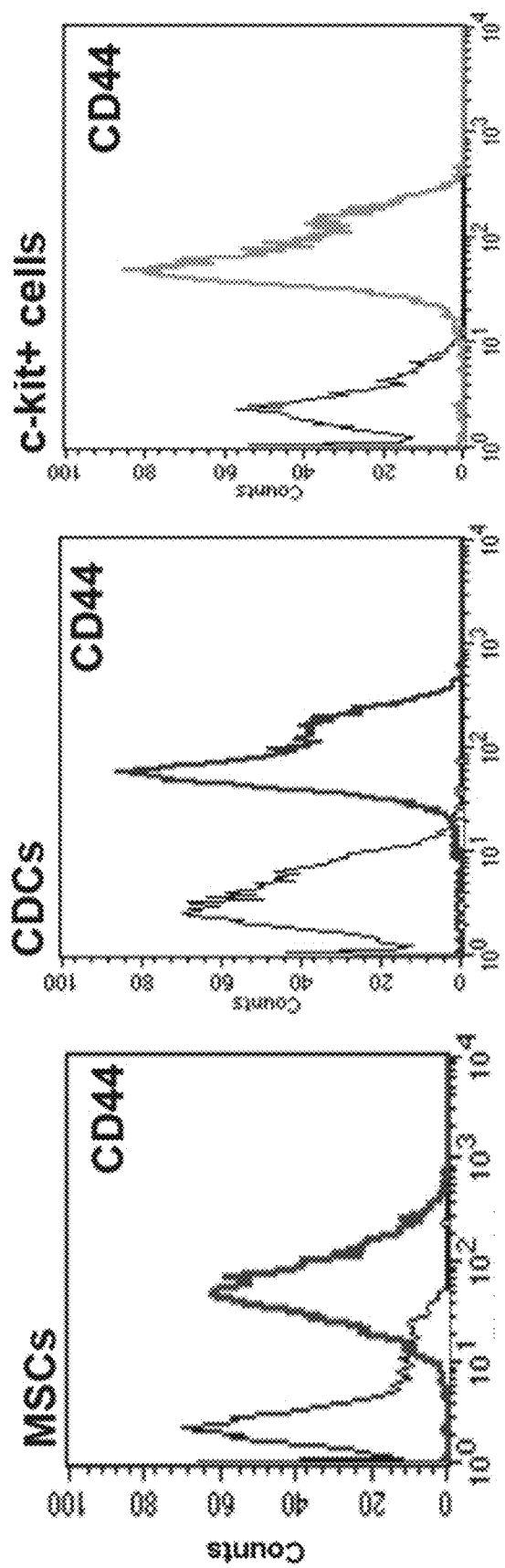
FIGS. 18A, 18B, 18C, 18D, and 18E illustrate flow cytometry analysis of cultured MSCs, CDCs and c-kit+ CSCs.
Figure 18B:
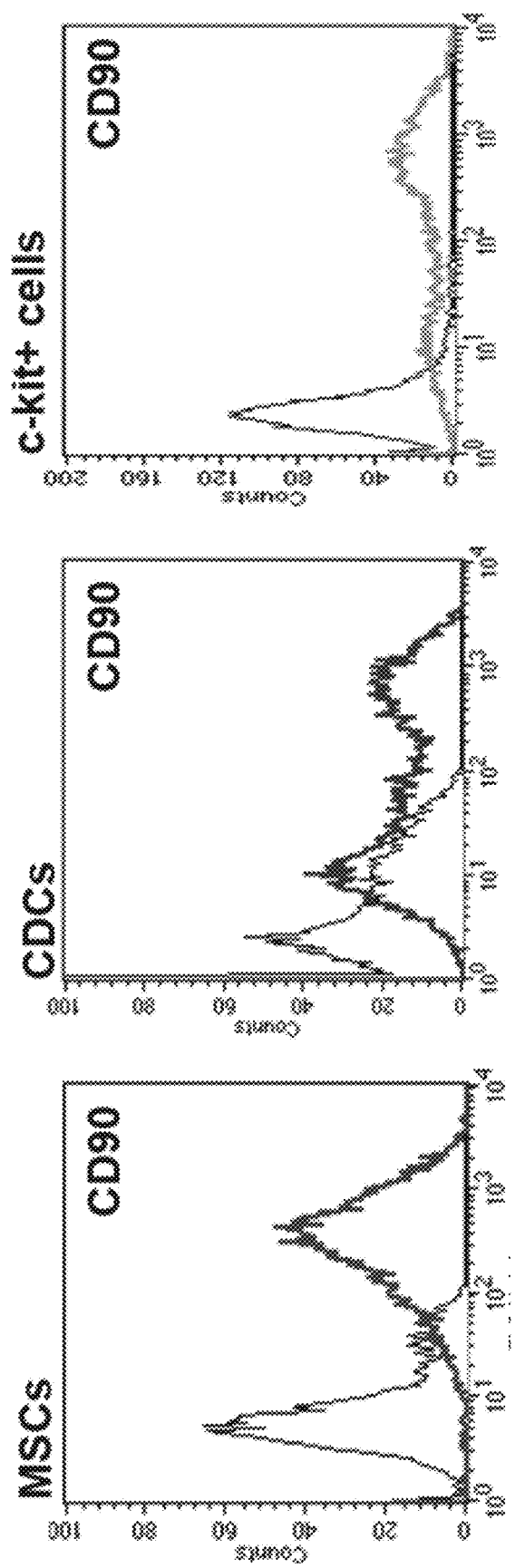
Figure 18C:
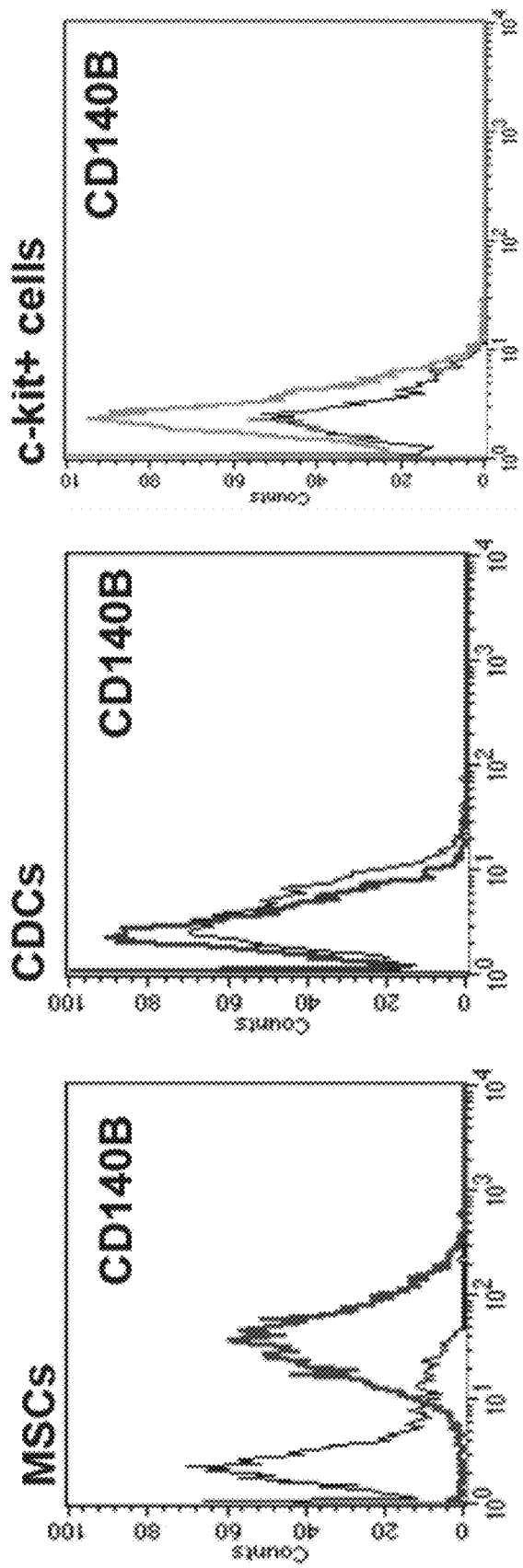
Figure 18D:
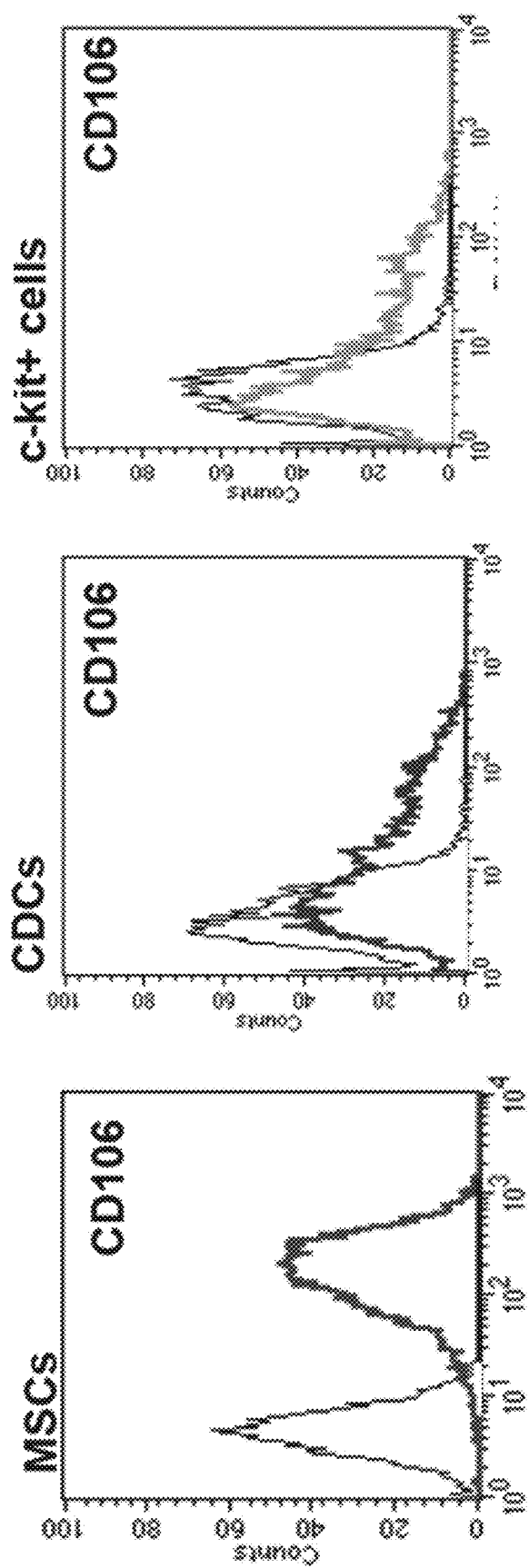
Figure 18E:
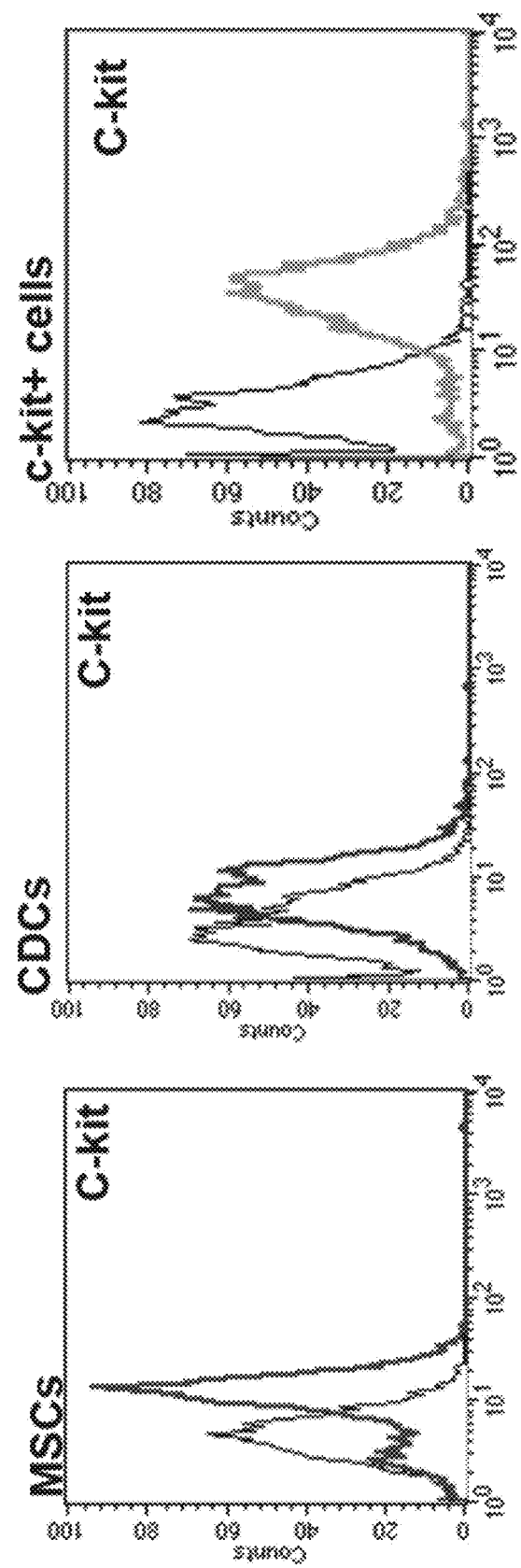

FIGS. 18A-18E. Flow cytometry analysis of cultured MSCs, CDCs and c-kit+ CSCs. FIG. 18A). MSC (red peaks in a colorized version), CDCs (Purple peaks in a colorized version) and c-kit+ CSCs (green peak in a colorized version) express CD44. FIG. 18B). the phenotypic difference between MSCs CDCs and c-kit is shown by the expression of CD90. MSCs express CD90 uniformity on their membrane while CDCs and c-kit CSCs show only a partial expression of CD90. FIG. 18C). C-kit CSCs and CDCs both showed no expression of CD140b while MSCs stain positive for CD140b. FIG. 18D). C-kit CSCs and CDCs both showed weak expression of CD106 while MSCs stain positive for CD106. FIG. 18E). MSCs and CDCs showed lower expression of c-kit antigen while c-kit+ CSCs showed uniform expression of c-kit.

Figure 19:
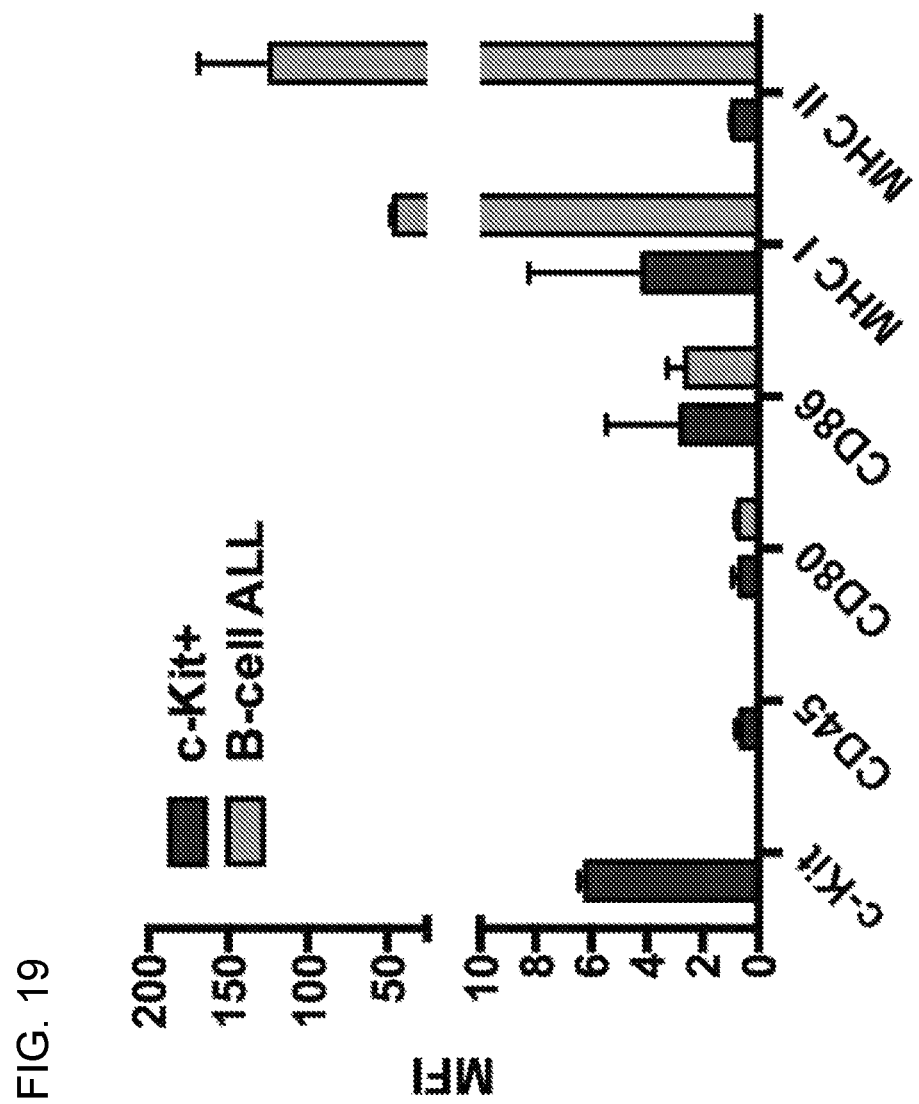
FIG. 19 depicts human cells express intermediate levels of major histocompatibility complex I (MHC I), low levels of MHC II and co-stimulatory molecules (CD80 and CD86). B cell acute lymphocytic leukemia (B-cell ALL) cells were used as positive control.

FIG. 19. Human cells express intermediate levels of major histocompatibility complex I (MHC I), low levels of MHC II and co-stimulatory molecules (CD80 and CD86). B cell acute lymphocytic leukemia (B-cell ALL) cells were used as positive control.

An Example of Isolation of C-Kit+ Stem Cells from Neonatal Patients with Congenital Heart Disease 1. Obtain biopsy tissue from the right atrial appendage (RAA) of human neonates diagnosed with congenital heart disease. Transfer the biopsy tissue to a 100 mm Petri dish filled with saline solution to wash the tissue. This step is repeated twice. Forceps sterilized in Steri 250 (Inotech) are used to remove fibrotic tissue and fat from the cardiac specimen. Samples are transferred to ISTEM® embryonic stem cell culture medium (Stem Cells, Inc.) and minced in 1-2 mm2 slices.

2. The tissue fragments are transferred to a 50 ml tube and allowed to sediment. The supernatant is removed and the sedimented pieces are resuspended in 5-10 ml of Collagenase type II, CSL2 (Worthington #4177). The collagenase is dissolved at a concentration of 2-5 mg/ml in ISTEM® medium. Subsequently, the samples are incubated on a shaker for 30-45 min at 37° C.

3. Following the collagenase treatment, the tube is removed from the shaker, undigested pieces are allowed to sediment and the supernatant containing the released cells is transferred into a 15 ml tube. The cells are centrifuged at 600 g for 10 min at 4° C., resuspended in the growth medium (see below) and plated in Petri dishes containing growth medium enriched with ISTEM® medium. Petri dishes are placed in an incubator at 37° C., under 5% C02.

4. At sub-confluence, the growth medium is removed and cells are detached with 5 ml of ACCUTASE® [Gibco #A11105-05] per dish for 2-3 minutes. When the cells detach, 5 ml of the ISTEM® medium is added and the suspension is transferred to a 15 ml test tube.

5. Cells are then sorted for c-kit with Miltenyi microbeads (CD117 MicroBead Kit human #130-091-332) in accordance with the kit's instructions. Cells are centrifuged for 10 min at 600 g, the supernatant is removed, the pellet is resuspended in 1 ml of cold MACS buffer (0.5% BSA and 2 mM EDTA) and the procedure is repeated. Subsequently, the supernatant is removed and the cell pellet is resuspended in 300 µl of MACS buffer, 100 µl Fc blocking buffer and 100 µl of mouse monoclonal c-kit antibody conjugated with microbeads (CD117 MicroBead Kit human, Miltenyi, cat. #130-091-332). The cells are incubated for 30 minutes at 4° C. on a 3600 swinging rotor. At the end of incubation, 1 ml of MACS buffer is added and the cells are centrifuged for 10 min at 600 g. The supernatant is removed and the cells are resuspended in 500 µl of MACS buffer. The column is activated using 500 µl of MACS buffer under the hood and the cells are transferred to the column. The depleted cell population (c-kitNEG cells) is collected in a 15 ml tube and discarded. The cells are washed 3 times by adding each time 500 µl of MACS buffer in the column. One ml of cold MACS buffer is added to the column and the column is detached from the Magnetic System. Subsequently, the plunger is applied to the column and the sorted c-kit+ cells are flushed into a 15 ml tube. The cells are centrifuged for 10 min at 600 g, resuspended in culture medium and plated in culture dishes.

6. c-kit+ cells are then plated in growth medium for expansion. After 1-2 months, approximately 1 million cells are obtained. The growth medium is changed twice a week for the entire period of cell expansion.

Reagents Used in Example

ISTEM® embryonic stem cell culture medium (Stem Cells, Inc.)
Fetal Bovine Serum (10%): 50 ml (Hyclone SH 30406.02-Lot DPK0185)
Recombinant Human FGF-basic: 50 µl of stock (100 ug/ml) F[10 ng/ml](PeproTech, 100-18B-Lot 1205CY08)
L-Glutathione: 1 ml of stock (100 mM) F[0.2 mM] (Sigma, G6013-Lot 10Ko9131)
Human Erythropoietin: 250 µl of stock (10 U/ml) F[0,005 U/ml] (Sigma E5627-Lot 125K1542)
C-kit antibody BD Pharmingen (#555714, Lot 40065)

Example 2

Neonatal-Derived Stem Cells Mediate Cardioprotection Via Paracrine Signaling Mechanism The findings of a clinical trial (Cardiac stem cells in patients with ischaemic cardiomyopathy, or SCIPIO) and other studies, reported the use of resident cardiac stem cells (c-kit+ hCSCs), to regenerate the infarcted myocardium in adults with ischemic myocardium. However, the studies performed using adult hCSCs cannot be extrapolated to the pediatric cases.

Neonates with heart failure are the most medically and surgically challenging and have the highest congenital mortality rates. The unique ability of neonatal-derived hCSCs to function at multiple levels, including generating myocardium and releasing angiogenic factors, makes these cells ideal to treat pediatrics heart failure patients, in specific embodiments of the disclosure.

The present example provides results about the efficiency of c-kit+ human cardiac stem cells to recover the ischemic myocardium in a rat myocardial infarction model. The results show phenotypic characterization of these cells and comparative study of growth potential and regenerative potential of c-kit+ cardiac stem cells which are dependent on the physiological conditions of the source of these cells. The results also highlight the importance the secretome of these cells that can shed more light on the underlying mechanism of action.

One can characterize c-kit+ hCSCs derived from neonatal and adult human myocardium, such as follows

| | |
|---|---|
| Embryonic Stem Cell markers | SSEA3 and SSEA4 |
| Mesenchymal Stem Cell marker: | CD105 and CD90 |
| Cardiac Stem cell Markers | C-kit |
| Cardiac-specific transcription factors | Nkx2.5, GATA4, ISL1 |
| Hematopoietic markers | CD34 and CD45 |

-continued

| | |
|---|---|
| Endothelial Marker | CD31 |
| Mast Cell Marker | Tryptase |

In specific embodiments, the following table notes specific markers or factors present or not present in the cells:

| | |
|---|---|
| Embryonic Stem Cell Markers | SSEA3-<3% cells positive |
| | SSEA4-<1% cells positive |
| Mesenchymal Stem cell Markers | CD105 >99% cells positive |
| | CD90 >85% cells positive |
| Cardiac Stem Cell marker | C-kit >85% |
| Cardiac-specific transcription factors | Nkx2.5, GATA4, and ISL1 <1% |
| Hematopoietic markers | CD45 and CD34 <1% |
| Mast Cell Marker | Tryptase <1% |
| Proliferative Marker | Ki67-Neonate >34% |
| | Adult >14% |

| Paracrine Factors | Neonate in vitro | Adult in vitro | Neonate in vivo | Adult in vivo | IMDM in vivo |
|---|---|---|---|---|---|
| VEGF-A | +++ | ++ | +++ | +++ | + |
| SDF-1α | +++ | ++ | +++ | Nc | No |
| ANG-1 | +++ | + | +++ | +++ | ++ |
| SCF | +++ | + | +++ | No | No |
| FGF | +++ | + | No | No | No |
| PDGF-b | +++ | + | No | No | No |
| HGF | +++ | ++ | +++ | No | No |

Example 3

Increasing Functional Activity of the Cells

In the present Example, it was considered for at least certain embodiments that a) the age and physiological condition of the source of hCSCs can affect their potential of recovering myocardial infarction after acute myocardial ischemia (AMI); and b) as a very small percentage of the transplanted cells could be detected days after myocardial infarction, the cardioprotective effects can be attributed to the secretome of the hCSCs. Compared herein are the phenotypic and functional properties of human cardiac stem cells (CSCs) isolated from human neonate heart (<1 month) to CSCs isolated from human adult heart (>50 years).

Cell Surface Markers and Clonogenic Capacity of CSCs hCSCs were isolated from the right atrium appendage of 11 neonate specimens (nCSC) and 10 adult hearts specimens (aCSC) using well established protocol. Flow cytometry analysis was performed on the affinity column purified c-kit$^+$ cells for various cell markers like: CD34 and CD45 (hematopoietic markers), CD31 (endothelial marker), tryptase (mast cell marker), Ki67 (proliferative marker), GATA4, ISL1, NKX2.5 (cardiac specific transcription factor), SSEA3 and SSEA4 (embryonic stem cell markers), CD105 and CD90 (mesenchymal stem cell marker) and c-kit at passage 3 for both nCSC and aCSCs.

nCSCs and aCSCs were negative for CD34, CD45, tryptase, CD31, SSEA3, SSEA4 CD105 and CD90 as well as for the cardiomyocytes specific transcription factor GATA4 and ISL1. Both type of cells were found to be positive for Ki67, Nkx2.5 and c-kit suggesting their cardiac origin and quantitatively, the number of ki67-positive in nCSCs was 3.5- fold higher as compared to aCSC. Neonatal derived c-kit+ CSCs showed a higher rate of proliferation as determined by higher expression of ki67 (neonate hCSCs 30.23%+1.8 vs adult hCSCs, 11.03%±0.65 p=0.0286). Thus, increasing age may suggest to adversely affecting the proliferative potential of CSCs. To validate this observation, single c-kit+ cell of nCSC and aCSCs was analyzed for its clonogenic capacity. The potential of a stem cell can be directly linked to the number of daughter cells to which it gives rise. Flow cytometry sorted single nCSC and aCSC were seeded in single well of 96 wells plate. Although nCSC and aCSC both could make a homogenous population of c-kit+ cells, spindle-shaped clones from nCSCs were formed over a period of 1 week from, but same number of clones from aCSC were formed over a month and the cells showed hypertrophy.

c-kit+ hCSCs are reported to express stem cell markers like POU5F1 (OCT3/4), NANOG, KLF4, and SOX2. The expression of these genes is important to maintain the self-renewing and multi-potent state of stem cells. Quantitative PCR was performed on the nCSCs and aCSCs at passage 3 (P-3) and passage 8 (P-8). Although the expression of pluripotency-associated genes was found in both cell types, results show that the expression of c-Kit, OCT3/4 and KLF4 was similar between the two CSCs types at P3, but at P-8 the expression of these genes was significantly decreased in aCSCs as compared to nCSCs. The expression of NANOG and SOX2 was significantly different between nCSCs and aCSCs at P3 as well as at P8. Data was analyzed by non-parametric t-test followed by Mann-Whitney's analysis. P value lesser than 0.05 was considered significant. The high levels of expression of pluripotency genes in nCSCs as compared to aCSC, can partially explain their higher clonogenic potential is dependent on age and may be responsible for its high clonogenic capacity.

Growth Properties of nCSCs and aCSCs

Cardiac stem cells like other stem cells have various unique features like expression of c-kit on cell surface or maintained telomeres length after numerous divisions or the doubling potential. Flow cytometer analysis showed that nCSCs retained their c-kit+ expression (%) with increasing passages (P3-P8), while aCSCs showed a decrease in the expression of c-kit+ with increasing passages. The difference in c-kit expression of hCSCs was significantly different after passage 5 (P5). The c-kit expression was maintained in neonatal hCSCs from P5 to P8 at 87.7%+1.3 while adult hCSCs lost c-kit expression with every increasing passage (P5, n=4, 69.75%±13.3, P6, n=4, 57.75%±11.2, p7, n=4, 52.50%+9.8, P8=40.25%+8.3). Data was analyzed using 2-way ANOVA, *=P<0.001, **=P<0.0001 The fold change in the number of daughter cells from nCSC and aCSCs was further analyzed, nCSCs maintained a high growth potential which remained unaffected by increasing number of passages, while aCSCs gradually lost their potential to give rise to daughter cells. Cardiac stem cells possess elevated levels of telomerase activity, which can be directly related to telomere length. Cells with shortened telomere length are known to have reduced growth potential and can't further give rise to daughter cells resulting in compromised stem cell property. The telomere lengths were analyzed of nCSC and aCSC at P3 and P8 using quantitative fluorescence in situ hybridization. Neonatal derived c-kit+ CSCs showed significantly longer telomere length compared to adult derived c-kit+ CSCs at passage 3 (P3). At passage 8, neonatal derived c-kit+ CSCs retained their telomere length while the telomere length was significantly decreased in adult c-kit+ CSCs at P3 to P8 (Neonate P3, n=4, 8.025 kbps±0.46, Neonate P8, n=4, 8.12 kbps±0.55 Vs adult P3, n=4, 3.3 kbps±0.36, P8, n=4, 0.18 kbps±0.047, *=P=0.0152). At P8, aCSCs became senescent as determined by β-galactosidase activity assay while no β-galactosidase activity was observed in neonatal c-kit+ CSCs at p8 (neonate hCSCs, n=4, 2.5%±1.9, adult hCSCs, n=4, 97.50%±6.0, P=0.0286). These results indicate that age is a major determinant of the biological potential of hCSCs. Four biomarkers were tested for hCSC activity, as progressive loss of c-kit expression, reduced cell divisions, telomeric shortening, and induction of senescence and expression of $p16^{INK4a}$. The removal of reactive oxygen species (ROS), which are produced in an active cell as a result of normal cellular metabolism, is very important for the survival of a cell otherwise the accumulation of oxidative damage may lead to cellular senescence.

Hydrogen peroxide is one such detrimental molecule. CSCs were treated with 50 mM hydrogen peroxide and cell death was estimated by TUNEL staining after 16 hours. Neonatal c-kit+ CSCs were significantly more resistant to hydrogen peroxide (15 minutes treatment at 50 mM hydrogen peroxide) induced cell death when compared to adult c-kit+ CSCs (neonate hCSCs, n=4, 8.5%±3.1, adult hCSCs, n=4, 96.50%±9.7, P=0.0286). Increasing age has adverse effects on the hCSC, suggesting nCSCs are highly active stem cells, which qualifies the canonical definition of stem cells of high proliferative activity and clonogenicity, suggesting that in very young heart, the stem cells efficiently contributes to preserve organ homoeostasis while in old hearts, the functional potential of these cells may be decline and coupled with defects in the recovery of the heart. These results also suggest that c-kit+ hCSCs undergo qualitative changes with age quantitative.

Transplantation of nCSC Improved Cardiac Function and Remodeled Left Ventricular as Compared to aCSC The studies conducted above about the phenotypic characteristic, clonogenic properties, growth potential, cell metabolism, telomere length and senescence suggested that nCSC may have a higher potential to recover the injured myocardium in an acute myocardial infarction model as compared to aCSC. To consider this, a randomized blinded study was performed by transplanting nCSCs or aCSCs at passage 3, as a stem cell therapy in an acute infarcted myocardium model of immunodeficient rat. After the left anterior descending artery ligation, CDCs, cardiac fibroblasts, or Iscove modified Dulbecco medium (IMDM; control) were injected. The consistency of the MI model was verified for each treatment group by performing random echocardiography at baseline and 24 hours after MI. There was no difference in EF between the 3 groups at baseline or 24 hours post-MI that signified all MIs performed were consistently among all three groups. Both stem cell therapies improved the cardiac function and attenuated left ventricular remodeling of MIs. Rats receiving aCSCs therapy did demonstrate an improvement in ejection fraction and fractional shortening relative to F12 basal medium, but these improvements were more pronounced in nCSCs treated MI. Animals receiving nCSC therapy had significantly improved ejection fraction and fractional shortening as early as 1 week post-MI and these improvements were sustained for at least 4 weeks. A Representative M-mode picture from animals of different treated or untreated groups is utilized. Improvements in ejection fraction and FS were significantly greater in nCSC animals versus aCSCs treated animals. Animals in the MI+IMDM group demonstrated a significant increase in end systolic volume (ESV) and End diastolic Volume (EDV) but MI+aCSC or MI+nCSC had decreased post-MI ESV and EDV at all the time points studied. This difference was very significant with nCSCs therapy after 4 weeks. nCSCs treated MIs also showed thickening of posterior cell wall which was otherwise noted to be relatively thin in IMDM or aCSCs treated MIs. Scar formation was quantified by histological evaluation of myocardial sections with Masson trichrome to determine the extent of infarct expansion after LAD ligation. Hearts were harvested, perfused and five rats were randomly selected from each group (MI+IMDM, MI+nCSC and MI+aCSC). A typical Masson trichrome pattern in hearts transplanted with control, cardiac fibroblast, or CDCs is determined. The positive red-stained regions (viable tissue) within the predominately blue-stained regions (fibrous tissue) are the typical pattern seen in all hearts. After 4 weeks post-MI, chronic infarct size was analyzed by measuring the area of fibrosis relative to total stained myocardial area. Animals receiving either aCSCs or nCSCs therapy had significantly smaller infarcted areas relative to IMDM-treated controls but the reduction in myocardial infarction was even significantly smaller in nCSC treated hearts as compared to aCSC.

The human CSCs were tracked using their expression of human nuclear antigen (HNA), to represent a lineage tracing experiment in the rodent myocardial infarct (MI) model to determine their final identity within the myocardium. Using immunofluorescence to detect human nuclei, there was low engraftment of transplanted nCSCs or aCSCs into cardiomyocytes in the peri-infarct zone of infarcted wall of rodent myocardium after 4 weeks. The frequency of cycling cardiomyocytes (co-expressing Ki-67$^+$ and α-sarcomeric actin (per mm2)) was comparatively increased after nCSCs cell therapy as compared to aCSCs therapy and these cells were found only in the peri-infarct region. Both stem cell therapies augmented the preservation/formation of neovessels (isolectin B4) and arterioles (α-SMA), but the formation of neo-vessels and arterioles was significantly higher after nCSCs therapy as compared to aCSCs therapy. Although blood vessels spanned the length of the infarct, the largest significant differences were found in the epicardium of the mid-infarct receiving the transplanted nCSCs while arterioles were found to be significantly higher in anterior and mid-infarct zones after nCSC therapy.

Expression of Paracrine Factors by nCSCs and aCSCs

The results so far have shown that transplanted CSCs were minimally present in the myocardium after 3 days of transplantation. Thus, in specific embodiments a paracrine mechanism is an explanation for the myocardial recovery after CSCs transplantation. To determine the expression of paracrine factors using a candidate based analysis in the cells in vitro, cultured nCSCs and aCSCs were immunostained for paracrine factors, well established for their role in myocardial regeneration: HFG and IGF-1 (cardioprotective; inhibits apoptosis and stimulates growth), SCF and SDF-1α (Stem cell function and proliferation) and ANG-1, VEGF-A, PDGF and FGF (angiogenesis). nCSCs and aCSCs, both type of cells expressed paracrine factors. The quantitative analysis of the conditioned medium (CM) isolated from nCSCs and aCSCs for using ELISA showed the secretion of above-mentioned factors was significantly higher from nCSCs as compared to aCSC (except IGF-1). The environment in the infarcted myocardium is highly inflammatory and ischemic during the transplantation of CSCs, which is a very different from the in vitro conditions where CSCs were cultured. This change in the environment may cause the CSCs to change the expression pattern of their paracrine factors. Thus the expression was analyzed of above mentioned paracrine factors in a time course manner at two time points; a) 24 hours and b) 72 hours post-MI. Hearts receiving nCSCs and aCSCs were immunostained for the paracrine factors using listed specific antibodies. Human mitochondria antigen (Mito) was used to track the human cells in the rat myocardium. There was differential secretion of 5 paracrine factors in the cases of nCSCs and aCSCs. VEGF-A, HGF, SCF, SDF-1α and ANG-1 were secreted by nCSCs while aCSC were found to express VEGF and ANG-1. To analyze the effect of myocardium environment, the hearts were harvested after 72 hour of post-MI receiving CSCs treatment, as a second time point. Immunohistochemical analysis was performed for the 5-paracrine factors, which showed a differential expression pattern at 24 hours. The infarcted area, which received CSCs, showed that nCSCs continued to express all the paracrine factors except SDF-1α whose expression could not be sustained, while aCSCs expressed ANG-1 and VEGFA. Also, a greater number of nCSCs was retained in the peri-infarcted region of rat myocardium after 72 hours of transplantation as compared to aCSCs. These heart sections were co-stained with Ki67 and human mitochondria antigen to identify the proliferative potential of CSCs in vivo. Immunohistochemical analysis showed that nCSCs were significantly more proliferative (6-fold, P<0.05), as compared to aCSC. To determine whether CSCs transplantation has an effect on the inflammation in the infarcted myocardium, macrophage infiltration was measured in the infarcted zone of MI animals treated with IMDM, nCSCs and aCSCs. MI animals receiving nCSCs has significantly (P<0.05) lower inflammation as compared to animals receiving aCSCs. These data indicate that, in certain embodiments, nCSCs secretes more paracrine factors with cardioprotective, chemokine and angiogenic capability, as compared to the paracrine expression by aCSCs. This paracrine secretion and increased proliferative capability ofnCSCs can explain increased neovascularization and decreased inflammation in the infarcted myocardium. These data provide evidence that there is a difference in the cytokine secretion by the nCSCs as compared to aCSCs and implicate highly expressed cytokines as the key secreted cytokines involved in the functional recovery.

CSCs Secrete Pro-Angiogenic, Pro-Proliferative and Anti-Apoptotic Factors, which can Improve Cardiac Function and Attenuate Ventricular Remodeling Similar to CSCs Transplantation in MI Model CSCs are shown to secrete many paracrine factors which has cardio protective potential. As the presence of CSCs is minimal soon after the transplantation, one can consider that functional potential of cardiac stem cell therapy is dependent on the quality and quantity of various proteins in hCSCs' secretome, which can be categorized according to their molecular function. The conditioned medium (CM) was analyzed from CSCs for a) angiogenic potential, b) antioxidant potential and c) proliferative potential. To analyze the angiogenic potential of CM isolated from CSCs, endothelial cell tube-forming assays were performed using human umbilical vein endothelial cells (HUVECs). HuVEC cells cultured with complete endothelial growing media or CM harvested from CSCs, formed tubes within 6 hours of plating on the matrix, while no tube formation (P<0.05) was assessed in the presence of basal medium (IMDM). The anti-oxidant properties of CM were further analyzed on neonatal rat cardiomyocytes (NRCMs). NRCMs were treated with 50 mM hydrogen peroxide in the presence or absence of CM, and the number of apoptotic cells was determined using AnnexinV/PI staining by FACS. Hydrogen peroxide treatment increased the early apoptotic cells and total dead cells NRCMs while CM treatment significantly (P<0.01) ameliorated the effect of hydrogen peroxide on the cells. The effect of CM on non-proliferative NRCM by Brdu incorporation using FACS (BrDu flow kit, BD Biosciences) was analyzed. A significant 2-fold increase (P<0.05) was found in the cells undergoing proliferation after treatment of NRCMs with CM. To determine whether the angiogenic, antioxidant and proliferative potential of CM derived from CSCs can be correlated with improved functional potential, a randomized blinded study was performed to evaluate the effectiveness of CM and CSCs in improving acute infarcted myocardium in an immunodeficient rat model. 1 million yhCSCs or the CM from 1 million yhCSCs corresponding to 0.5 ug protein were injected in the rat myocardium after induction of MI. Echocardiography performed at 7 and 28 days showed CM from CSCs was more effective (7% better ejection fraction) than CSCs proving that CM derived from CSCs is more effective than CSCs transplantation for functional recovery of left ventricle in the rat myocardium in MI model. There was improvement in the EDV, posterior wall thickness and systolic volume. After 4 weeks post-MI, infarct size was analyzed as mentioned above. Animals receiving either CM or CSCs therapy had significantly smaller infarcted areas relative to IMDM-treated controls (P<0.05) but the reduction in myocardial infarction was even significantly smaller in CM treated hearts as compared to CSCs transplantation. The paracrine factors of CSCs are the real agents to bring myocardial recovery and attenuate LV remodeling in the infarcted heart. Thus, the product of CSCs are more important for cardiac regeneration and functional recovery than the physical presence of the CSCs.

The Comparative Analysis of the Secretome of aCSCs and nCSCs

So far, it has been shown that the nCSCs have better regeneration potential than aCSCs and at least in specific embodiments the paracrine secretions of these CSCs are the factors responsible for myocardial regeneration and functional improvement. Thus, one can identify and quantitate the proteins in the secretome of CSCs, which can promote angiogenesis, cardiomyocyte proliferation and endogenous stem cell differentiation while reducing inflammation and cellular apoptosis in the injured myocardium. CM was further characterized by comparing CM from nCSCs and aCSCs for their angiogenic potential using tube assay formation by HuVEC cells. The CM from nCSCs has more angiogenic potential as compared to CM from aCSCs. Moreover the higher concentration of ahCSCs actually hampers the tube formation as shown in the quantification graph. CM from nCSCs and aCSCs was utilized for SDS-PAGE analysis, and there was a different pattern of proteins among aCSCs (A1-A5) and nCSCs (N1-N5). Also no disintegration of the proteins was observed. 50 microgram of the protein from each sample was trypsin digested and analyzed by LC-MS/MS for the identification of the protein. The protein component analysis (PCA) of the proteins showed that the paracrine secretion of neonate samples was very similar among different samples while no such similarity was found among the adult samples, which can be explained due to different way of life of individuals. There was a total of 798 and 331 proteins in yhCSCs and aCSCs, respectively, out of which 298 proteins were found to be expressed in the CM of both cell types. The proteins were further categorized on the basis of >2 fold difference in their expression pattern and volcano plot identified a total of 384 proteins in the CM of nCSCs and 64 proteins in CM from aCSCs. Proteins were categorized as per the GOCC and GOBP enrichment analysis. GOMF enrichment suggested that proteins related to cellular metabolism, DNA and RNA processing were highly enriched in CM from nCSCs while CM from aCSC was enriched in collagen, cytoskeleton and carbohydrate binding proteins.

Example 4

Cardiac Stem Cells with Enhanced Functional Activity for Cardiac Repair

The present example concerns the therapeutic use of cells from dysfunctional myocardium of pediatric end stage failing heart (ESHF) patients.

Methods and Results: ESHF derived human cardiosphere derived cells (hCDCs) had a higher number of cardiac stem cells expressing c-kit+, Islet-1+, and Sca-1+. When transplanted in an infarcted rodent model, ESHF derived hCDCs had a significantly higher preservation of ventricular function, prevented adverse remodeling, and enhanced angiogenesis when compared with congenital heart disease (CHD) derived CDCs. The superior functional recovery of the ESHF derived hCDCs was mediated in part by increased SDF-1α and VEGF-A secretion which recruited more endogenous stem cells and proliferation of cardiomyocytes. The mechanism for the superior secretome is due to the heat shock response (HSR) which is supported by three lines of evidence. First, gain of function studies demonstrated that the HSR induced the low functioning CHD derived CDCs to significantly recover the injured myocardium to the same extent as ESHF derived CDCs. Secondly, loss-of function studies targeting the HSR down regulated the ability of the ESHF derived CDCs to functionally recover the injured myocardium. Finally, the HSR alone increased the number of the c-kit+ CSCs both in vitro and in vivo.

Conclusion: These findings indicate that the HSR enhances the functional activity of ESHF derived CDCs by regulating their secretome.

In accordance with the present Example, CDCs or c-kit+ cardiac stem cells (CSCs) can be treated with celastrol (or other inducers of the heat shock response) to enhance the functional ability of the treated cells to repair damaged myocardium in patients suffering from heart failure. In specific embodiments, cells are obtained from the myocardium of an individual and exposed to one or more heat shock response inducers such that the expression of the cells, the secretion by the cells, or both are altered compared to the cells obtained from the individual and not exposed to one or more heat shock response inducers.

The scope of the present application is not intended to be limited to the particular embodiments of the process, machine, manufacture, composition of matter, means, methods and steps described in the specification.

REFERENCES

Roger V L. Epidemiology of heart failure. *Circ Res.* 2013; 113:646-659.

Go A S, Mozaffarian D, Roger V L, Benjamin E J, Berry J D, Blaha M J, Dai S, Ford E S, Fox C S, Franco S, Fullerton H J, Gillespie C, Hailpern S M, Heit J A, Howard V J, Huffman M D, Judd S E, Kissela B M, Kittner S J, Lackland D T, Lichtman J H, Lisabeth L D, Mackey R H, Magid D J, Marcus G M, Marelli A, Matchar D B, McGuire D K, Mohler E R, 3rd, Moy C S, Mussolino M E, Neumar R W, Nichol G, Pandey D K, Paynter N P, Reeves M J, Sorlie P D, Stein J, Towfighi A, Turan T N, Virani S, Wong N D, Woo D, Turner M B. Heart disease and stroke statistics-2014 update: A report from the american heart association. *Circulation.* 2014; 129: e28-e292.

Rossano J W, Kim J, Decker J A, Price J F, Zafar F, Graves D E, Morales D L, Heinle J S, Bozkurt B, Towbin J A, Denfield S W, Dreyer W J, Jefferies J L. Prevalence, morbidity, and mortality of heart failure-related hospitalizations in children in the united states: A population-based study. *Journal of cardiac failure.* 2012; 18:459-470.

Porrello E R, Mahmoud A I, Simpson E, Hill J A, Richardson J A, Olson E N, Sadek H A. Transient regenerative potential of the neonatal mouse heart. *Science.* 2011; 331:1078-1080.

Messina E, De Angelis L, Frati G, Morrone S, Chimenti S, Fiordaliso F, Salio M, Battaglia M, Latronico M V, Coletta M, Vivarelli E, Frati L, Cossu G, Giacomello A. Isolation and expansion of adult cardiac stem cells from human and murine heart. *Circulation research.* 2004; 95:911-921.

Beltrami A P, Barlucchi L, Torella D, Baker M, Limana F, Chimenti S, Kasahara H, Rota M, Musso E, Urbanek K, Len A, Kajstura J, Nadal-Ginard B, Anversa P. Adult cardiac stem cells are multipotent and support myocardial regeneration. *Cell.* 2003; 114:763-776.

Smith R R, Barile L, Cho H C, Leppo M K, Hare J M, Messina E, Giacomello A, Abraham M R, Marban E. Regenerative potential of cardiosphere-derived cells expanded from percutaneous endomyocardial biopsy specimens. *Circulation.* 2007; 115:896-908.

Matsuura K, Nagai T, Nishigaki N, Oyama T, Nishi J, Wada H, Sano M, Toko H, Akazawa H, Sato T, Nakaya H, Kasanuki H, Komuro I. Adult cardiac sca-1-positive cells differentiate into beating cardiomyocytes. *The Journal of biological chemistry.* 2004; 279:11384-11391.

He J Q, Vu D M, Hunt G, Chugh A, Bhatnagar A, Bolli R. Human cardiac stem cells isolated from atrial appendages stably express c-kit. *PloS one.* 2011; 6: e27719.

Stolzing A, Sethe S, Scutt A M. Stressed stem cells: Temperature response in aged mesenchymal stem cells. *Stem cells and development.* 2006; 15:478-487.

Mishra R, Vijayan K, Colletti E J, Harrington D A, Matthiesen T S, Simpson D, Goh S K, Walker B L, Almeida-Porada G, Wang D, Backer C L, Dudley S C, Jr., Wold L E, Kaushal S. Characterization and functionality of cardiac progenitor cells in congenital heart patients. *Circulation.* 2011; 123:364-373.

Bu L, Jiang X, Martin-Puig S, Caron L, Zhu S, Shao Y, Roberts D J, Huang P L, Domian I J, Chien K R. Human isl1 heart progenitors generate diverse multipotent cardiovascular cell lineages. *Nature.* 2009; 460: 113-117.

Bolli R, Chugh A R, D'Amario D, Loughran J H, Stoddard M F, Ikram S, Beache G M, Wagner S G, Len A, Hosoda T, Sanada F, Elmore J B, Goichberg P, Cappetta D, Solankhi N K, Fahsah I, Rokosh D G, Slaughter M S, Kajstura J, Anversa P. Cardiac stem cells in patients with ischaemic cardiomyopathy (scipio): Initial results of a randomised phase 1 trial. *Lancet.* 2011; 378:1847-1857.

Makkar R R, Smith R R, Cheng K, Malliaras K, Thomson L E, Berman D, Czer L S, Marban L, Mendizabal A, Johnston P V, Russell S D, Schuleri K H, Lardo A C, Gerstenblith G, Marban E. Intracoronary cardiosphere-derived cells for heart regeneration after myocardial infarction (caduceus): A prospective, randomised phase 1 trial. *Lancet.* 2012; 379:895-904.

Simpson D L, Mishra R, Sharma S, Goh S K, Deshmukh S, Kaushal S. A strong regenerative ability of cardiac stem cells derived from neonatal hearts. *Circulation.* 2012; 126: S46-53.

Kajstura J, Len A, Finato N, Di Loreto C, Beltrami C A, Anversa P. Myocyte proliferation in end-stage cardiac failure in humans. Proceedings of the i National Academy of Sciences of the United States of America. 1998; 95:8801-8805.

Anversa P, Kajstura J. Ventricular myocytes are not terminally differentiated in the adult mammalian heart. Circulation research. 1998; 83:1-14.

Rajabi M, Kassiotis C, Razeghi P, Taegtmeyer H. Return to the fetal gene program protects the stressed heart: A strong hypothesis. *Heart failure reviews.* 2007; 12:331-343.

Malliaras K, Makkar R R, Smith R R, Cheng K, Wu E, Bonow R O, Marban L, Mendizabal A, Cingolani E, Johnston P V, Gerstenblith G, Schuleri K H, Lardo A C, Marban E. Intracoronary cardiosphere-derived cells after myocardial infarction: Evidence of therapeutic regeneration in the final 1-year results of the caduceus trial (cardiosphere-derived autologous stem cells to reverse ventricular dysfunction). *Journal of the American College of Cardiology.* 2014; 63:110-122.

Zaruba M M, Soonpaa M, Reuter S, Field L J. Cardiomyogenic potential of c-kit(+)-expressing cells derived from neonatal and adult mouse hearts. *Circulation.* 2010; 121:1992-2000.

Simpson D, Liu H, Fan T H, Nerem R, Dudley S C, Jr. A tissue engineering approach to progenitor cell delivery results in significant cell engraftment and improved myocardial remodeling. *Stem Cells.* 2007; 25:2350-2357.

Chimenti I, Smith R R, Li T S, Gerstenblith G, Messina E, Giacomello A, Marban E. Relative roles of direct regeneration versus paracrine effects of human cardiosphere-derived cells transplanted into infarcted mice. *Circ Res.* 2010; 106:971-980.

Zhang X, Wang X, Zhu H, Kranias E G, Tang Y, Peng T, Chang J, Fan G C. Hsp20 functions as a novel cardiokine in promoting angiogenesis via activation of vegfr2. *PloS one.* 2012; 7: e32765.

Miyata S, Minobe W, Bristow M R, Leinwand L A. Myosin heavy chain isoform expression in the failing and nonfailing human heart. *Circ Res.* 2000; 86:386-390.

Razeghi P, Young M E, Alcorn J L, Moravec C S, Frazier O H, Taegtmeyer H. Metabolic gene expression in fetal and failing human heart. *Circulation*. 2001; 104:2923-2931.

Afanasiev S A, Falaleeva L P, Rebrova T U, Suslova T E, Popov S V, Karpov R S. Effect of stress-proteins on survival of bone marrow mesenchymal stem cells after intramyocardial transplantation against the background of postinfarction heart remodeling. *Bulletin of experimental biology and medicine*. 2008; 146:111-115.

Genth-Zotz S, Bolger A P, Kalra P R, von Haehling S, Doehner W, Coats A J, Volk H D, Anker S D. Heat shock protein 70 in patients with chronic heart failure: Relation to disease severity and survival. *International journal of cardiology*. 2004; 96:397-401.

Wang Y, Chen L, Hagiwara N, Knowlton A A. Regulation of heat shock protein 60 and 72 expression in the failing heart. *Journal of molecular and cellular cardiology*. 2010; 48:360-366.

Reynolds B A, Weiss S. Generation of neurons and astrocytes from isolated cells of the adult mammalian central nervous system. *Science*. 1992; 255:1707-1710.

Rietze R L, Reynolds B A. Neural stem cell isolation and characterization. *Methods in enzymology*. 2006; 419:3-23.

Mirotsou M, Jayawardena T M, Schmeckpeper J, Gnecchi M, Dzau V J. Paracrine mechanisms of stem cell reparative and regenerative actions in the heart. *Journal of molecular and cellular cardiology*. 2011; 50:280-289.

Angelini A, Castellani C, Ravara B, Franzin C, Pozzobon M, Tavano R, Libera L D, Papini E, Vettor R, De Coppi P, Thiene G, Vescovo G. Stem-cell therapy in an experimental model of pulmonary hypertension and right heart failure: Role of paracrine and neurohormonal milieu in the remodeling process. *The Journal of heart and lung transplantation: the official publication of the International Society for Heart Transplantation*. 2011; 30:1281-1293.

McGinley L M, McMahon J, Stocca A, Duffy A, Flynn A, O'Toole D, O'Brien T. Mesenchymal stem cell survival in the infarcted heart is enhanced by lentivirus vector-mediated heat shock protein 27 expression. *Human gene therapy*. 2013; 24:840-851.

Feng Y, Huang W, Meng W, Jegga A G, Wang Y, Cai W, Kim H W, Pasha Z, Wen Z, Rao F, Modi R M, Yu X, Ashraf M. Heat shock improves sca-1+ stem cell survival and directs ischemic cardiomyocytes toward a prosurvival phenotype via exosomal transfer: A critical role for hsfl/mir-34a/hsp70 pathway. *Stem cells*. 2014; 32:462-472.

Cesselli D, Beltrami A P, D'Aurizio F, Marcon P, Bergamin N, Toffoletto B, Pandolfi M, Puppato E, Marino L, Signore S, Livi U, Verardo R, Piazza S, Marchionni L, Fiorini C, Schneider C, Hosoda T, Rota M, Kajstura J, Anversa P, Beltrami C A, Len A. Effects of age and heart failure on human cardiac stem cell function. *The American journal of pathology*. 2011; 179:349-366.

Laflamme M A, Chen K Y, Naumova A V, Muskheli V, Fugate J A, Dupras S K, Reinecke H, Xu C, Hassanipour M, Police S, O'Sullivan C, Collins L, Chen Y, Minami E, Gill E A, Ueno S, Yuan C, Gold J, Murry C E. Cardiomyocytes derived from human embryonic stem cells in pro-survival factors enhance function of infarcted rat hearts. *Nature biotechnology*. 2007; 25:1015-1024.

Kannaiyan R, Shanmugam M K, Sethi G. Molecular targets of celastrol derived from thunder of god vine: Potential role in the treatment of inflammatory disorders and cancer. *Cancer letters*. 2011; 303:9-20.

Salminen A, Lehtonen M, Paimela T, Kaarniranta K. Celastrol: Molecular targets of thunder god vine. *Biochemical and biophysical research communications*. 2010; 394:439-442.

Go A S, Mozaffarian D, Roger V L, Benjamin E J, Berry J D, Blaha M J, et al. Executive summary: heart disease and stroke statistics-2014 update: a report from the american heart association. Circulation. 2014; 129(3): 399-410. Epub Jan. 22, 2014. doi: 10.1161/01.cir.0000442015.53336.12. PubMed PMID: 24446411.

Go A S, Mozaffarian D, Roger V L, Benjamin E J, Berry J D, Blaha M J, et al. Heart disease and stroke statistics-2014 update: a report from the american heart association. Circulation. 2014; 129 (3): e28-e292. Epub Dec. 20, 2013. doi: 10.1161/01.cir.0000441139.02102.80. PubMed PMID: 24352519.

Garbern J C, Lee R T. Cardiac stem cell therapy and the promise of heart regeneration. Cell stem cell. 2013; 12(6):689-98. Epub Jun. 12, 2013. doi: 10.1016/j.stem.2013.05.008. PubMed PMID: 23746978; PubMed Central PMCID: PMC3756309.

Bolli R, Chugh A R, D'Amario D, Loughran J H, Stoddard M F, Ikram S, et al. Cardiac stem cells in patients with ischaemic cardiomyopathy (SCIPIO): initial results of a randomised phase 1 trial. Lancet. 2011; 378(9806):1847-57. Epub Nov. 18, 2011. doi: 10.1016/S0140-6736(11) 61590-0. PubMed PMID: 22088800; PubMed Central PMCID: PMC3614010.

Bolli R, Tang X L, Sanganalmath S K, Rimoldi 0, Mosna F, Abdel-Latif A, et al. Intracoronary delivery of autologous cardiac stem cells improves cardiac function in a porcine model of chronic ischemic cardiomyopathy. Circulation. 2013; 128(2):122-31. Epub Jun. 13, 2013. doi: 10.1161/CIRCULATIONAHA.112.001075. PubMed PMID: 23757309; PubMed Central PMCID: PMC3807652.

Tang X L, Rokosh G, Sanganalmath S K, Yuan F, Sato H, Mu J, et al. Intracoronary administration of cardiac progenitor cells alleviates left ventricular dysfunction in rats with a 30-day-old infarction. Circulation. 2010; 121(2):293-305. Epub Jan. 6, 2010. doi: 10.1161/CIRCULATIONAHA.109.871905. PubMed PMID: 20048209; PubMed Central PMCID: PMC2814341.

Beltrami A P, Barlucchi L, Torella D, Baker M, Limana F, Chimenti S, et al. Adult cardiac stem cells are multipotent and support myocardial regeneration. Cell. 2003; 114(6):763-76. Epub Sep. 9, 2003. PubMed PMID: 14505575.

Chugh A R, Beache G M, Loughran R I, Mewton N, Elmore J B, Kajstura J, et al. Administration of cardiac stem cells in patients with ischemic cardiomyopathy: the SCIPIO trial: surgical aspects and interim analysis of myocardial function and viability by magnetic resonance. Circulation. 2012; 126 (11 Suppl 1): S54-64. Epub Sep. 9, 2012. doi: 10.1161/CIRCULATIONAHA.112.092627. PubMed PMID: 22965994; PubMed Central PMCID: PMC3448934.

Pagani F D, DerSimonian H, Zawadzka A, Wetzel K, Edge A S, Jacoby D B, et al. Autologous skeletal myoblasts transplanted to ischemia-damaged myocardium in humans. Histological analysis of cell survival and differentiation. Journal of the American College of Cardiology. 2003; 41(5): 879-88. Epub Dec. 3, 2003. PubMed PMID: 12628737.

Bergmann 0, Bhardwaj R D, Bernard S, Zdunek S, Barnabe-Heider F, Walsh S, et al. Evidence for cardiomyocyte renewal in humans. *Science*. 2009; 324(5923): 98-102. Epub Apr. 4, 2009. doi: 10.1126/science.1164680. PubMed PMID: 19342590; PubMed Central PMCID: PMC2991140.

Kajstura J, Rota M, Cappetta D, Ogorek B, Arranto C, Bai Y, et al. Cardiomyogenesis in the aging and failing human heart. *Circulation*. 2012; 126(15):1869-81. Epub Sep. 8, 2012. doi: 10.1161/CIRCULATIONAHA.112.118380. PubMed PMID: 22955965; PubMed Central PMCID: PMC3477474.

What is claimed is:

1. A pharmaceutical composition comprising human, neonatal cardiac stem cells and a pharmaceutically acceptable carrier, wherein the human, neonatal cardiac stem cells:
    (a) are positive for protein expression of ckit, SDF-1α, VEGF-A, PDGF-B, IL-6, FGF-2, and Nkx2.5,
    (b) are negative for protein expression of ISL1; and
    (c) are negative for protein expression of CD31, CD106, CD140b, or CD86.

2. The pharmaceutical composition of claim 1, wherein the human, neonatal cardiac stem cells are further negative for protein expression of CD34, CD80, SSEA4, SSEA3, or a combination thereof.

3. The pharmaceutical composition of claim 1, wherein the pharmaceutical composition further comprises an exosome.

4. The pharmaceutical composition of claim 1, wherein the human, neonatal cardiac stem cells are further positive for expression of one or more proteins selected from the group consisting of GDF15, GOT1, GOT2, MANF, PABPN1, PDLIM7, PLIN3, PPIA, PPP1CA, PPP1CB, PPP1CC, PPP2CA, PPP2CB, PPP3CA, SRI, SUMO1, TAGLN2, TMPO, TNFAIP6, TPM3, TPM4, VIM, YAP1, and YWHAG.

5. The pharmaceutical composition of claim 1, wherein the human, neonatal cardiac stem cells are further positive for expression of one or more proteins selected from the group consisting of HSPA13, HSPA1A, HSPA4, HSPA5, HSPA8, HSPD1, HSPE1, HSPH1, ST13, HOP, SUGT1, and UBB.

6. The pharmaceutical composition of claim 1, wherein the human, neonatal cardiac stem cells are further positive for expression of one or more proteins selected from the group consisting of ABRACL, LIF, MCFD2, NES, VIM, YBX1, and YBX2.

7. The pharmaceutical composition of claim 1, wherein the human, neonatal cardiac stem cells are further positive for expression of FKBP4, CXCL3, and PRDX5.

8. The pharmaceutical composition of claim 1, wherein the human, neonatal cardiac stem cells are in a therapeutically effective amount for treating a cardiac medical condition in a subject in need thereof.

9. The pharmaceutical composition of claim 8, wherein the cardiac medical condition is heart failure, cardiomyopathy, or congenital heart disease.

* * * * *